United States Patent
Chinn et al.

(10) Patent No.: US 9,518,121 B2
(45) Date of Patent: Dec. 13, 2016

(54) ANTI-JAGGED1 ANTIBODIES AND METHODS OF USE

(71) Applicant: Genentech, Inc., South San Francisco, CA (US)

(72) Inventors: Yvonne Chinn, Foster City, CA (US); Julie Q. Hang, San Jose, CA (US); Christian W. Siebel, Berkeley, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/619,930

(22) Filed: Feb. 11, 2015

(65) Prior Publication Data

US 2015/0252117 A1 Sep. 10, 2015

Related U.S. Application Data

(60) Provisional application No. 61/939,110, filed on Feb. 12, 2014.

(51) Int. Cl.
*A61K 39/395* (2006.01)
*C07K 16/28* (2006.01)
*A61K 47/48* (2006.01)
*A61K 39/00* (2006.01)

(52) U.S. Cl.
CPC ....... *C07K 16/2896* (2013.01); *A61K 39/3955* (2013.01); *A61K 47/48561* (2013.01); *C07K 16/28* (2013.01); *A61K 2039/505* (2013.01); *A61K 2039/507* (2013.01); *C07K 2317/21* (2013.01); *C07K 2317/33* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,703,489 B1 | 3/2004 | Ish-Horowicz et al. |
| 7,754,206 B2 | 7/2010 | Clarke et al. |
| 2008/0317760 A1 | 12/2008 | Gurney et al. |
| 2009/0081238 A1 | 3/2009 | Siebel et al. |
| 2010/0196385 A1 | 8/2010 | Bedian et al. |
| 2014/0314749 A1 | 10/2014 | French et al. |
| 2015/0232568 A1 | 8/2015 | Siebel et al. |

FOREIGN PATENT DOCUMENTS

| | | |
|---|---|---|
| WO | 2006/135949 | 12/2006 |
| WO | 2008/140826 A1 | 11/2008 |
| WO | 2009/124931 A2 | 10/2009 |
| WO | 2010/005566 | 1/2010 |
| WO | 2010/039832 | 4/2010 |
| WO | 2011/063237 A2 | 5/2011 |
| WO | 2013/052155 A1 | 4/2013 |
| WO | 2013/052155 A9 | 4/2013 |
| WO | 2013/192550 A2 | 12/2013 |
| WO | 2014/028446 A1 | 2/2014 |
| WO | 2014/151866 A1 | 9/2014 |

OTHER PUBLICATIONS

Brown et al (J. Immunol. May 1996; 156(9):3285-3291.*
Vajdos et al (J. Mol. Biol. Jul. 5, 2002;320(2); 415-428).*
Casset et al. (2003) BBRC 307, 198-205.*
Artavanis-Tsakonas et al., "Choosing a cell fate: a view from the Notch locus" Reviews 7(11-12) ( 1991).
Bork, et al., "Go hunting in sequence databases but watch out for the traps" Trends in Genetics 12(10):425-427 (Oct. 1996).
Bork, "Powers and Pitfalls in Sequence Analysis: The 70% hurdle" Genome Research(10):398-400 (2000).
Brenner, "Errors in genome annotation" Trends in Genetics 15(4):132-133 ( 1999).
Boroson, "Mutational analysis of avidity and fine specifity of anit-levan antibodies" J Immunol (added article title info), 163:6694-6701 (Dec. 1999).
Brummell et al., "Probing the combining site of anit-carbohydrate antibody by saturation-mutagensis: role of the heavy-chain CDR3 residues" Biochemistry 32(4):1180-1187 (Feb. 1993).
Burks, E., et al., "In vitro scanning saturation mutagenesis of an antibody binding pocket" P Natl Acad Sci USA 94:412-417 ( 1997).
Cao et al., "Osteopontin as potential biomarker and therapeutic target in gastric and liver cancers" World J. Gastroneterol. 18(30):3923-3930 ( 2012).
Chen et al., "An antibody drug conjugate targeting PMEL17" J. Biol. Chem (Manuscript M112.361485), (May 21, 2012).
Colman, P.M., "Effects of amino acid sequence changes on antibody-antigen interactions" RES Immunol 145:33-36 ( 1994).
Darwiche et al., "Inhibition of Notch signalling affect hepatic oval cell respone in rat mode of 22AF-PH" Dove Press 3:89-98 ( 2011).
Dill et al., "Constitutive Notch 2 Signaling Induces Heaptic Tumors in Mice" Hepatology 57:1607-1619 ( 2013).
Doerks et al., "Protein annotation: detective work for function prediction" Trends in Genentic 14(6):248-250 ( 1998).
Dorothy French, DVM. PhD, DACVP, "Microarray analysis reveals signaling pathways critical for hepatic progenitor cell survival and self-renewal" Slides ASIP Meeting, pp. 53 ( Apr. 8, 2011).
Fan B et al., "Cholangiocarcinomas can orginate from hepatocytes in mice" The Journal of clinical investigation 122(8):2911-2915 ( 2012).
Fiorotto, R. et al., "Progenitor Cell Activation and Liver Repair is Altered in Notch2 and RBP-J kappa-Defective Mice Exposed to Cholestatic Injuries" Journal of Hepatology 52(1):S45 (Apr. 2010).
Gao et al., "Expression of Jagged1 and its association with hepatitis B virus X protein in hepatocellular carcinoma" Biochemical and Biophysical Research Communications 256:341-347 ( 2007).

(Continued)

*Primary Examiner* — Sheela J Huff
(74) *Attorney, Agent, or Firm* — McNeill Baur PLLC

(57) ABSTRACT

The invention provides anti-Jagged1 antibodies and methods of using the same.

38 Claims, 39 Drawing Sheets

(56) References Cited

OTHER PUBLICATIONS

Gao et al., "Notch1 activation contributes to tumor cell growth and proliferation in human hepatocellular carcinoma HepG2 and SMMC7721 cells" International Journal of Oncology 41:1773-1781 (2012).
Geisler et al., "Liver-Specific Inactivation of Notch2, but not Notch1, Compromises Intrahepatic Bile Duct Development in Mice" Live Biology/Pathobiology 48(2):607-616 (Aug. 2008).
Gotoh et al., "Overexpression of osteopontin in hepatocellular carcinoma" Pathology International 52:19-24 (2002).
Groth et al., "Therapeutic Approachs to Modulating Notch Signaling: Current challenges and future prospects" Seminars in Cell & Development Biology 23:465-47 (2012).
Hattori et al., "Expression of the RNA-binding protein Musashi1 in adult liver stem-like cells" Hepatology Research 40:432-437, 2010.
Ho et al., "Advances in Liver Cancer AntibodyTherapies" Biodrugs 25(5):275-284 (2011).
Ho et al., "AKT (v-Akt Murine Thymoma ViralOncogene Homolog 1) and N-Ras (Neuroblastoma Ras Viral Oncogene Homolog) Coactivation in the Mouse Liver Promotes Rapid Carcinogenesis by Way of mTOR (Mammalian Target of Rapamycin Complex 1), FOXM1 (Forkhead Box M1)/SKP2, and c-Myc Pathways" Hepatology 55:833-845 (2012).
International Search Report and Written Opinion for International App. No. PCT/US2014/026588, filed Mar. 13, 2014, pp. 23 (mailed Aug. 20, 2014).
International Search Report and Written Opinion for PCT Application No. PCT/US2015/015456, filed Feb. 11, 2015, pp. 13 (mailed May 7, 2015).
International Search Report for International Patent Application No. PCT/US2013/054664, pp. 5 (mailed Dec. 3, 2013).
Jang et al., "The structural basis for DNA binding by an anti-DNA autoantibody" Mol Immunol. 35(18):1207-17 (Dec. 1998).
Jensen et al., "Transit-amplifying ductal (oval) cells and their hepatocytic progeny are characterized by a novel and distintive expression of delta-like protein/preadipocyte factor 1/fetal antigen 1." Am Journal Physiol 164(4):1347-1359 (2004).
Kobayashi, H., et al., "Tryptophan H33 plays an important role in pyrimidin (6-4) pyrimidone photoproduct binding by a high-affinity antibody" Protein Eng 12(10):879-884 (1999).
Koch et al. "Notch and Cancer: a double-edged sword" Cellular and Molecular Life Sciences 64:2746-2762 (2007).
Louvi et al., "Notch and disease: A growing field" Seminars in Cell & Development Biology 23:473-480 (2012).
Lozier et al., "Notch signaling regulates bile duct morphogenesis in mice" PLoS One 3(3):e1851 (2008).
McCright et al., "A mouse model of Alagille syndrome: Notch2 as a genetic modifier of Jag1 haploinsufficiency" Development 129(4):1075-82 (Feb. 2002).
Mullendore et al., "Ligand-dependent Notch Signaling is Involved in Tumor Initiation and Tumor Maintenance in Pancreatic Cancer" Clinical Cancer Research 15:2291-2301 (Apr. 1, 2009).
Ngo et al., "Computational complexity, protein structure prediction, and the Levinthal paradox" The Protein Folding Problem and Tertiary Structure Prediction pp. 491-495 (1994).
Nijjar et al., "Notch receptor expression in adult humar liver: a possible role in bile duct formation and hepatic neovascularization" Hepatology 34:1184-1192 (2001).
Nishina et al., "Restored expression of the tumor supressor gene RUNX3 reduces cancer stem cells in hepatocellular carcinomas by suppressing Jagged1—Notch signaling" Oncology Reports 26:523-531 (2011).
Oda et al., "Mutations in the human Jagged1 gene responsible for Alagille syndrome" Nat Genet. 16:235-42 (Jul. 1997).
Piccoli et al., "Alagille syndrome and the Jagged1 gene" Semin Liver Dis. 21(4):525-34 (2001).
Pikarsky et al., "NF-kb functions as a tumour promoter in inflammation-associated cancer" Nature 43:461-468 (Sep. 23, 2004).
Qi et al., "Notch1 signalling inhibits growth of human hepatocellular carcinoma through induction of cell cycle arrest and apoptosis" Cancer Research(63):8323-8329 (Dec. 1, 2003).
Ryan et al., "Bile duct proliferation in Jag1/fringe heterozygous mice identifies candidate modifies of the Alagille syndrome hepatic phenotype" Hepatology 48(6):1989-97 (2008).
Sakurai et al., "Loss of hepatic NF-kb activity enhances chemical hepatocarcinogenesis through sustained c-Jun N-terminal kinase 1 activation" PNAS 103(28):10544-10551 (Jul. 11, 2006).
Sekiya et al., "Intrahepatic cholangiocarcinoma can arise from Notch-mediated conversion of hepatocytes" The Journal of Clinical Investigation 122(11):3914-3918 (2012).
Shen et al., "GSI-has a better effect in inhibiting heptocellular carcinoma cell groth than GSI-X, or GSI-XXI" Anticancer Drugs 23:683-690 (2012).
Shin et al., "SPP1 polymorphisms associated with HBV clearance and HCC occurence" Intl. J. Epidemiology 36:1001-1008 (2007).
Skolnick et al., "From genes to protein structure and function: novel applications of computational approaches in the genomic era" Trends in Biotech. 18(1):34-39 (2000).
Smith et al., "The challenges of genome sequence annotation of 'the devil is in the details'" Nature Biotech(15):1222-1223 (1997).
Sparks et al., "Notch signaling regulates formation of the three-dimensional architecture of intrahepatic bile ducts in mice" Hepatology 51(4):1391-400 (2010).
Tanimizu et al., "Notch signalling controls hepatoblat differentiation by altering the expression of liver-enriched transcription factor" J Cell Science 117:3165-3174 (2004).
Tchorz et al., "Notch2 Signaling Promotes Biliary Epithelial Cell Fate Specification and Tubulogenesis During Bile Duct Development in Mice" Hepatology 50(3):871-879 (Sep. 2009).
Tokuriki, et al., "Stability effect of mutations and proten evolvability" Current Opinion in Structural Biology 19:596-604 (2009).
Viatour et al., "Notch signaling inhibits hepatocellular carcinoma following inactivation of the RB pathway" The Journal of Experimental Medicine 208(10):1963-1976 (Aug. 29, 2011).
Villanueva et al., "Notch Signaling is Activated in Human Hepatocellular Carcinoma and Induces Tumor Formation in Mice" Gastroenterology 143:1660-1669 (2012).
Wakabayashi et al., "Regulation of Notch1 Signaling by Nrf2: Implications for Tissue Regeneration" Science Signaling 3(130):1-11 (Jul. 13, 2010).
Wang et al., "Hepatitis B Virus X protein promotes the growth of hepatocellular carcinoma by modulation of the Notch signaling pathway" Oncology Reports 27:1170-1176 (2012).
Wang et al., "Notch1 signaling contributes to the oncogenic effect of HBx on human hepatic cells" Biotechnol. Lett 35:29-37 (2012).
Wang et al., "Notch1 signaling sensitizes tumor necrosis factor-reated apoptosis-inducing ligand-induced apoptosis in human hepatocellualr carcinoma cells by inhibiting Akt/Hdm2-mediated p53 degradation and up-regulation p53-depended DR5 expression"Journal of Biological Chemistry 284(24):16183-16190 (2009).
Wells, "Addivity of Mutational Effects of Proteins" Biochemistry 29:8509-8517 (1990).
Written Opinion for International Patent Application No. PCT/US2013/054664., pp. 5 (mailed Dec. 3, 2013).
Wu et al., "Therpeutic Antibody targeting of individual Notch receptors" Nature 464:1052-1057 (2010).
Wu et al., "Notch Signaling and its role in breast cancer" Frontiers in Bioscience 12:4370-4383 (2007).
Xu et al., "Yes-Associated Protein is an Independent Prognostic Marker in Hepatocellular Carcinoma" Cancer(115):4576-85 (Oct. 1, 2009).
Yuen et al., "Seological markers of liver cancer" Best Practice & Research Clinical Gastroenterology 19(1):91-99 (2005).
Zender et al., "Identification and Validation of Oncogenes in Liver Cancer Using an Integrative Oncogenomic Approach" Cell(125):1253-1267 (Jun. 30, 2006).
Zeuner et al., "The Notch2-Jagged1 interaction mediates sytem cell factor signaling in erythropisis" Cell Death Differ. 18(2):370-80 (2011).

(56) References Cited

OTHER PUBLICATIONS

Zhoe et al., "Downregulation of the Notch signaling pathway inhibits hepatocellular carcinoma cell invasion by inactivation of matrix metalloproteinase-2 and-9 and vascular endothelial growth factor" Oncology reports 28(3):874-882 ( 2012).

Zhou et al., "The Down-Regulation of Notch1 Inhibits the Invasion and Migration of Hepatocellular Carcinoma Cell by Inactiviating the Cyclooxygenase-2/Snail/E-Cadherin Pathway In Vitro" Dig. Dis Sci (2012).

* cited by examiner

HUMAN Jag1 (SEQ ID NO:1)

MRSPRTRGRSGRPLSLLLALLCALRAKVCGASGQFELEILSMQNVNGELQNGNCCGGARN
PGDRKCTRDECDTYFKVCLKEYQSRVTAGGPCSFGSGSTPVIGGNTFNLKASRGNDRNRI
VLPFSFAWPRSYTLLVEAWDSSNDTVQPDSIIEKASHSGMINPSRQWQTLKQNTGVAHFE
YQIRVTCDDYYYGFGCNKFCRPRDDFFGHYACDQNGNKTCMEGWMGPECNRAICRQGCSP
KHGSCKLPGDCRCQYGWQGLYCDKCIPHPGCVHGICNEPWQCLCETNWGGQLCDKDLNYC
GTHQPCLNGGTCSNTGPDKYQCSCPEGYSGPNCEIAEHACLSDPCHNRGSCKETSLGFEC
ECSPGWTGPTCSTNIDDCSPNNCSHGGTCQDLVNGFKCVCPPQWTGKTCQLDANECEAKP
CVNAKSCKNLIASYYCDCLPGWMGQNCDININDCLGQCQNDASCRDLVNGYRCICPPGYA
GDHCERDIDECASNPCLNGGHCQNEINRFQCLCPTGFSGNLCQLDIDYCEPNPCQNGAQC
YNRASDYFCKCPEDYEGKNCSHLKDHCRTTPCEVIDSCTVAMASNDTPEGVRYISSNVCG
PHGKCKSQSGGKFTCDCNKGFTGTYCHENINDCESNPCRNGGTCIDGVNSYKCICSDGWE
GAYCETNINDCSQNPCHNGGTCRDLVNDFYCDCKNGWKGKTCHSRDSQCDEATCNNGGTC
YDEGDAFKCMCPGGWEGTTCNIARNSSCLPNPCHNGGTCVVNGESFTCVCKEGWEGPICA
QNTNDCSPHPCYNSGTCVDGDNWYRCECAPGFAGPDCRININECQSSPCAFGATCVDEIN
GYRCVCPPGHSGAKCQEVSGRPCITMGSVIPDGAKWDDDCNTCQCLNGRIACSKVWCGPR
PCLLHKGHSECPSGQSCIPILDDQCFVHPCTGVGECRSSSLQPVKTKCTSDSYYQDNCAN
ITFTFNKEMMSPGLTTEHICSELRNLNILKNVSAEYSIYIACEPSPSANNEIHVAISAED
IRDDGNPIKEITDKIIDLVSKRDGNSSLIAAVAEVRVQRRPLKNRTDFLVPLLSSVLTVA
WICCLVTAFYWCLRKRRKPGSHTHSASEDNTTNNVREQLNQIKNPIEKHGANTVPIKDYE
NKNSKMSKIRTHNSEVEEDDMDKHQQKARFAKQPAYTLVDREEKPPNGTPTKHPNWTNKQ
DNRDLESAQSLNRMEYIV

MURINE Jag1 (SEQ ID NO:2)

MRSPRTRGRPGRPLSLLLALLCALRAKVCGASGQFELEILSMQNVNGELQNGNCCGGVRN
PGDRKCTRDECDTYFKVCLKEYQSRVTAGGPCSFGSGSTPVIGGNTFNLKASRGNDRNRI
VLPFSFAWPRSYTLLVEAWDSSNDTIQPDSIIEKASHSGMINPSRQWQTLKQNTGIAHFE
YQIRVTCDDHYYGFGCNKFCRPRDDFFGHYACDQNGNKTCMEGWMGPDCNKAICRQGCSP
KHGSCKLPGDCRCQYGWQGLYCDKCIPHPGCVHGTCNEPWQCLCETNWGGQLCDKDLNYC
GTHQPCLNRGTCSNTGPDKYQCSCPEGYSGPNCEIAEHACLSDPCHNRGSCKETSSGFEC
ECSPGWTGPTCSTNIDDCSPNNCSHGGTCQDLVNGFKCVCPPQWTGKTCQLDANECEAKP
CVNARSCKNLIASYYCDCLPGWMGQNCDININDCLGQCQNDASCRDLVNGYRCICPPGYA
GDHCERDIDECASNPCLNGGHCQNEINRFQCLCPTGFSGNLCQLDIDYCEPNPCQNGAQC
YNRASDYFCKCPEDYEGKNCSHLKDHCRTTTCEVIDSCTVAMASNDTPEGVRYISSNVCG
PHGKCKSQSGGKFTCDCNKGFTGTYCHENINDCESNPCKNGGTCIDGVNSYKCICSDGWE
GAHCENNINDCSQNPCHYGGTCRDLVNDFYCDCKNGWKGKTCHSRDSQCDEATCNNGGTC
YDEVDTFKCMCPGGWEGTTCNIARNSSCLPNPCHNGGTCVVNGDSFTCVCKEGWEGPICT
QNTNDCSPHPCYNSGTCVDGDNWYRCECAPGFAGPDCRININECQSSPCAFGATCVDEIN
GYQCICPPGHSGAKCHEVSGRSCITMGRVILDGAKWDDDCNTCQCLNGRVACSKVWCGPR
PCRLHKSHNECPSGQSCIPVLDDQCFVRPCTGVGECRSSSLQPVKTKCTSDSYYQDNCAN
ITFTFNKEMMSPGLTTEHICSELRNLNILKNVSAEYSIYIACEPSLSANNEIHVAISAED
IRDDGNPVKEITDKIIDLVSKRDGNSSLIAAVAEVRVQRRPLKNRTDFLVPLLSSVLTVA
WVCCLVTAFYWCVRKRRKPSSHTHSAPEDNTTNNVREQLNQIKNPIEKHGANTVPIKDYE
NKNSKMSKIRTHNSEVEEDDMDKHQQKVRFAKQPVYTLVDREEKAPSGTPTKHPNWTNKQ
DNRDLESAQSLNRMEYIV

*FIG. 1*

HUMAN Jag2 (SEQ ID NO:3)

MRAQGRGRLPRRLLLLLALWVQAARPMGYFELQLSALRNVNGELLSGACCDGDGRTTRAG
GCGHDECDTYVRVCLKEYQAKVTPGPCSYGHGATPVLGGNSFYLPPAGAAGDRARARAR
AGGGDQDPGLVVIPFQFAWPRSFTLIVEAWDWDNDTTPNEELLIERVSHAGMINPEDRWKS
LHFSGHVAHLELQIRVRCDENYYSATCNKFCRPRNDFFGHYTCDQYGNKACMDGWMGKEC
KEAVCKQGCNLLHGGCTVPGECRCSYGWQGRFCDECVPYPGCVHGSCVEPWQCNCETNWG
GLLCDKDLNYCGSHHPCTNGGTCINAEPDQYRCTCPDGYSGRNCEKAEHACTSNPCANGG
SCHEVPSGFECHCPSGWSGPTCALDIDECASNPCAAGGTCVDQVDGFECICPEQWVGATC
QLDANECEGKPCLNAFSCKNLIGGYYCDCIPGWKGINCHINVNDCRGQCQHGGTCKDLVN
GYQCVCPRGFGGRHCELERDECASSPCHSGGLCEDLADGFHCHCPQGFSGPLCEVDVDLC
EPSPCRNGARCYNLEGDYYCAPDDFGGKNCSVPREPCPGGACRVIDGCGSDAGPGMPGT
AASGVCGPHGRCVSQPGGNFSCICDSGFTGTYCHENIDDCLGQPCRNGGTCIDEVDAFRC
FCPSGWEGELCDTNPNDCLPDPCHSRGRCYDLVNDFYCACDDGWKGKTCHSREFQCDAYT
CSNGGTCYDSGDTFRCACPPGWKGSTCAVAKNSSCLPNPCVNGGTCVSGASFSCICRDG
WEGRTCTHNTNDCNPLPCYNGGICVDGVNWFRCECAPGFAGPDCRINIDECQSSPCAYGA
TCVDEINGYRCSCPPGRAGPRCQEVIGFGRSCWSRGTPFPHGSSWVEDCNSCRCLDGRRD
CSKVWCGWKPCLLAGQPEALSAQCPLGQRCLEKAPGQCLRPPCEAWGECGAEEPPSTPCL
PRSGHLDNNCARLTLHFNRDHVPQGTTVGAICSGIRSLPATRAVARDRLLVLLCDRASSG
ASAVEVAVSFSPARDLPDSSLIQGAAHAIVAAITQRGNSSLLLAVTEVKVETVVTGGSST
GLLVPVLCGAFSVLWLACVVLCVWWTRKRRKERERSRLPREESANNQWAPLNPIRNPIER
PGGHKDVLYQCKNFTPPPRRADEALPGPAGHAAVREDEEDEDLGRGEEDSLEAEKFLSHK
FTKDPGRSPGRPAHWASGPKVDNRAVRSINEARYAGKE

MURINE Jag2 (SEQ ID NO:4)

MRARGWGRLPRRLLLLLVLCVQATRPMGYFELQLSALRNVNGELLSGACCDGDGRTTRAG
GCGRDECDTYVRVCLKEYQAKVTPGPCSYGYGATPVLGGNSFYLPPAGAAGDRARARSR
TGGHQDPGLVVIPFQFAWPRSFTLIVEAWDWDNDTTPDEELLIERVSHAGMINPEDRWKS
LHFSGHVAHLELQIRVRCDENYYSATCNKFCRPRNDFFGHYTCDQYGNKACMDGWMGKEC
KEAVCKQGCNLLHGGCTVPGECRCSYGWQGKFCDECVPYPGCVHGSCVEPWHCDCETNWG
GLLCDKDLNYCGSHHPCVNGGTCINAEPDQYLCACPDGYLGKNCERAEHACASNPCANGG
SCHEVPSGFECHCPSGWSGPTCALDIDECASNPCAAGGTCVDQVDGFECICPEQWVGATC
QLDANECEGKPCLNAFSCKNLIGGYYCDCLPGWKGINCQININDCHGQCQHGGTCKDLVN
GYQCVCPRGFGGRHCELEYDKCASSPCRRGGICEDLVDGFRCHCPRGLSGLHCEVDMDLC
EPSPCLNGARCYNLEGDYYCAPEDFGGKNCSVPRDTCPGGACRVIDGCGFEAGSRARGV
APSGICGPHGHCVSLPGGNFSCICDSGFTGTYCHENIDDCMGQPCRNGGTCIDEVDSFRC
FCPSGWEGELCDINPNDCLPDPCHSRGRCYDLVNDFYCACDDGWKGKTCHSREFQCDAYT
CSNGGTCYDSGDTFRCACPPGWKGSTCTIAKNSSCVPNPCVNGGTCVSGDSFSCICRDG
WEGRTCTHNTNDCNPLPCYNGGICVDGVNWFRCECAPGFAGPDCRINIDECQSSPCAYGA
TCVDEINGYRCSCPPGRSGPRCQEVVIFTRPCWSRGMSFPHGSSWMEDCNSCRCLDGHRD
CSKVWCGWKPCLLSGQPSDPSAQCPPGQQCQEKAVGQCLQPPCENWGECTAEEPLPPSTP
CQPRSSHLDNNCARLTLRFNRDQVPQGTTVGAICSGIRALPATRAAAHDRLLLLLCDRAS
SGASAVEVAMSFSPARDLPDSSLIQSTAHAIVAAITQRGNSSLLLAVTEVKVETVVMGGS
STGLLVPVLCSVFSVLWLACVVICVWWTRKRRKERERSRLPRDESTNNQWAPLNPIRNPI
ERPGGSGLGTGGHKDILYQCKNFTPPPRRAGEALPGPAGHGAGGEDEEDEELSRGDGDSP
EAEKFISHKFTKDPSCSLGRPACWAPGPKVDNRAVRSTKDVRRAGRE

*FIG. 2*

Sequence of expressed protein murine Jag1-DSL-EGF1-4 (mouse Jag1 antigen)

ADLGSQFELEILSMQNVNGELQNGNCCGGVRNPGDRKCTRDECDTYFKVCLKEYQSRVTAGGPC
SFGSGSTPVIGGNTFNLKASRGNDRNRIVLPFSFAWPRSYTLLVEAWDSSNDTIQPDSIIEKAS
HSGMINPSRQWQTLKQNTGIAHFEYQIRVTCDDHYYGFGCNKFCRPRDDFFGHYACDQNGNKTC
MEGWMGPDCNKAICRQGCSPKHGSCKLPGDCRCQYGWQGLYCDKCIPHPGCVHGTCNEPWQCLC
ETNWGGQLCDKDLNYCGTHQPCLNRGTCSNTGPDKYQCSCPEGYSGPNCEIAEHACLSDPCHNR
GSCKETSSGFECECSPGWTGPTCSTNIDDEFGLVPRGSGHHHHHH  (SEQ ID NO. 5)

*FIG. 3A*

Sequence of expressed protein human Jag1-DSL-EGF1-4 (human Jag1 antigen)

QFELEILSMQNVNGELQNGNCCGGARNPGDRKCTRDECDTYFKVCLKEYQSRVTAGGPCSFGSG
STPVIGGNTFNLKASRGNDRNRIVLPFSFAWPRSYTLLVEAWDSSNDTVQPDSIIEKASHSGMI
NPSRQWQTLKQNTGVAHFEYQIRVTCDDYYYGFGCNKFCRPRDDFFGHYACDQNGNKTCMEGWM
GPECNRAICRQGCSPKHGSCKLGDCRCQYGWQGLYCDKCIPHPGCVHGICNEPWQCLCETNWGG
QLCDKDLNYCGTHQPCLNGGTCSNTGPDKYQCSCPEGYSGPNCEIAEHACLSDPCHNRGSCKET
SLGFECECSPGWTGPTCSTNIDD  (SEQ ID NO. 6)

*FIG. 3B*

Sequence of expressed protein murine Jag2-DSL-EGF1-4 (mouse Jag2 antigen)

ADLGSMGYFELQLSALRNVNGELLSGACCDGDGRTTRAGGCGRDECDTYVRVCLKEYQAKVTPT
GPCSYGYGATPVLGGNSFYLPPAGAAGDRARARSRTGGHQDPGLVVIPFQFAWPRSFTLIVEAW
DWDNDTTPDEELLIERVSHAGMINPEDRWKSLHFSGHVAHLELQIRVRCDENYYSATCNKFCRP
RNDFFGHYTCDQYGNKACMDGWMGKECKEAVCKQGCNLLHGGCTVPGECRCSYGWQGKFCDECV
PYPGCVHGSCVEPWHCDCETNWGGLLCDKDLNYCGSHHPCVNGGTCINAEPDQYLCACPDGYLG
KNCERAEHACASNPCANGGSCHEVPSGFECHCPSGWNGPTCALDIDEEFGLVPRGSGHHHHHH
(SEQ ID NO. 7)

*FIG. 3C*

Sequence of expressed protein human Jag2-DSL-EGF1-4 (human Jag2 antigen)

ARPMGYFELQLSALRNVNGELLSGACCDGDGRTTRAGGCGHDECDTYVRVCLKEYQAKVTPTGP
CSYGHGATPVLGGNSFYLPPAGAAGDRARARARAGGDQDPGLVVIPFQFAWPRSFTLIVEAWDW
DNDTTPNEELLIERVSHAGMINPEDRWKSLHFSGHVAHLELQIRVRCDENYYSATCNKFCRPRN
DFFGHYTCDQYGNKACMDGWMGKECKEAVCKQGCNLLHGGCTVPGECRCSYGWQGRFCDECVPY
PGCVHGSCVEPWQCNCETNWGGLLCDKDLNYCGSHHPCTNGGTCINAEPDQYRCTCPDGYSGRN
CEKAEHACTSNPCANGGSCHEVPSGFECHCPSGWSGPTCALDIDEEFGLVPRGSGHHHHHH
(SEQ ID NO. 8)

HVR-H1 Sequences

| Antibody # | Kabat Number | | | | | | | | | | SEQ ID NO |
|---|---|---|---|---|---|---|---|---|---|---|---|
| | 26 | 27 | 28 | 29 | 30 | 31 | 32 | 33 | 34 | 35 | |
| A, A-1, A-2 A-1 (S101T) | G | F | T | F | S | N | Y | G | I | H | 35 (also 11, 19, 27) |

HVR-H2 Sequence

| Antibody # | Kabat Number | | | | | | | | | | | | | | | | | SEQ ID NO |
|---|---|---|---|---|---|---|---|---|---|---|---|---|---|---|---|---|---|---|
| | 50 | 51 | 52 | 52A | 53 | 54 | 55 | 56 | 57 | 58 | 59 | 60 | 61 | 62 | 63 | 64 | 65 | |
| A, A-1, A-1 (S101T) | W | I | T | P | D | G | G | Y | T | D | Y | A | D | S | V | K | G | 36 (also 12, 20) |
| A-2 | W | I | T | G | N | G | G | Y | S | D | Y | A | D | S | V | K | G | 28 |
| Consensus | W | I | T | P/G | D/N | G | G | Y | T/S | D | Y | A | D | S | V | K | G | 71 |

*FIG. 5A*

HVR-H3 Sequence

| Antibody # | Kabat Number | | | | | | | SEQ ID NO |
|---|---|---|---|---|---|---|---|---|
| | 95 | 96 | 97 | 98 | 100k | 101 | 102 | |
| A, A-2 | A | G | S | W | F | A | Y | 13 (also 29) |
| A-1 | A | G | S | L | F | A | Y | 21 |
| A-1 (S101T) | A | G | T | L | F | A | Y | 37 |
| Consensus | A | G | S/T | W/L | F | A | Y | 77 |

FIG. 5B

HVR-L1 Sequences

| Antibody # | Kabat Number | | | | | | | | | | | SEQ ID NO |
|---|---|---|---|---|---|---|---|---|---|---|---|---|
| | 24 | 25 | 26 | 27 | 28 | 29 | 30 | 31 | 32 | 33 | 34 | |
| A, A-1, A-2, A-1 (S101T) | R | A | S | Q | D | V | S | T | A | V | A | 38 (also 14, 22, 30) |

HVR-L2 Sequences

| Antibody # | Kabat Number | | | | | | | SEQ ID NO |
|---|---|---|---|---|---|---|---|---|
| | 50 | 51 | 52 | 53 | 54 | 55 | 56 | |
| A, A-1, A-2, A-1 (S101T) | S | A | S | F | L | Y | S | 39 (also 15, 23, 31) |

HVR-L3 Sequences

| Clone # | Kabat Number | | | | | | | | | | SEQ ID NO |
|---|---|---|---|---|---|---|---|---|---|---|---|
| | 89 | 90 | 91 | 92 | 93 | 94 | 95 | 96 | 97 | | |
| A, A-2 | Q | Q | S | Y | T | T | P | P | T | | 16 (also 32) |
| A-1, A-1 (S101T) | Q | Q | Y | Y | T | T | A | T | T | | 40 (also 24) |
| Consensus | Q | Q | S/Y | Y | T | T | P/A | P/T | T | | 74 |

FIG. 6

Framework Sequences of Antibodies A, A-1, A-2 Light Chain Variable Domain

LC-FR1 $^{1}$Asp Ile Gln Met Thr Gln Ser Pro Ser Ser Leu Ser Ala Ser Val Gly Asp Arg Val Thr Ile Thr Cys$^{23}$ SEQ ID NO: 43

LC-FR2 $^{35}$Trp Tyr Gln Gln Lys Pro Gly Lys Ala Pro Lys Leu Leu Ile Tyr$^{49}$ SEQ ID NO: 44

LC-FR3 $^{57}$Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys$^{88}$ SEQ ID NO: 45

LC-FR4 $^{98}$Phe Gly Gln Gly Thr Lys Val Glu Ile Lys Arg$^{108}$ SEQ ID NO: 46

Framework Sequences of Antibodies A, A-1, A-2 Heavy Chain Variable Domain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ SEQ ID NO: 47

HC-FR2 $^{36}$Trp Val Arg Gln Ala Pro Gly Lys Gly Leu Glu Trp Val Gly$^{49}$ SEQ ID NO: 48

HC-FR3 $^{66}$Arg Phe Thr Ile Ser Ala Asp Thr Ser Lys Asn Thr Ala Tyr Leu Gln Met Asn Ser Leu Arg Ala Glu Asp Thr Ala Val Tyr Tyr Cys Ala Arg$^{94}$ SEQ ID NO: 49

HC-FR4 $^{103}$Trp Gly Gln Gly Thr Leu Val Thr Val Ser Ser$^{113}$ SEQ ID NO: 50

```
  1   EVQLVESGGG LVQPGGSLRL SCAASGFTFS NYGIHWVRQA PGKGLEWVGW ITGNGGYSDY   60
 61   ADSVKGRFTI SADTSKNTAY LQMNSLRAED TAVYYCARAG SWFAYWGQGT LVTVSSASTK  120
121   GPSVFPLAPS SKSTSGGTAA LGCLVKDYFP EPVTVSWNSG ALTSGVHTFP AVLQSSGLYS  180
181   LSSVVTVPSS SLGTQTYICN VNHKPSNTKV DKKVEPKSCD KTHTCPPCPA PELLGGPSVF  240
241   LFPPKPKDTL MISRTPEVTC VVVDVSHEDP EVKFNWYVDG VEVHNAKTKP REEQYNSTYR  300
301   VVSVLTVLHQ DWLNGKEYKC KVSNKALPAP IEKTISKAKG QPREPQVYTL PPSREEMTKN  360
361   QVSLTCLVKG FYPSDIAVEW ESNGQPENNY KTTPPVLDSD GSFFLYSKLT VDKSRWQQGN  420
421   VFSCSVMHEA LHNHYTQKSL SLSPG                                       445
                                                          SEQ ID NO: 108

☐ = CDR
```

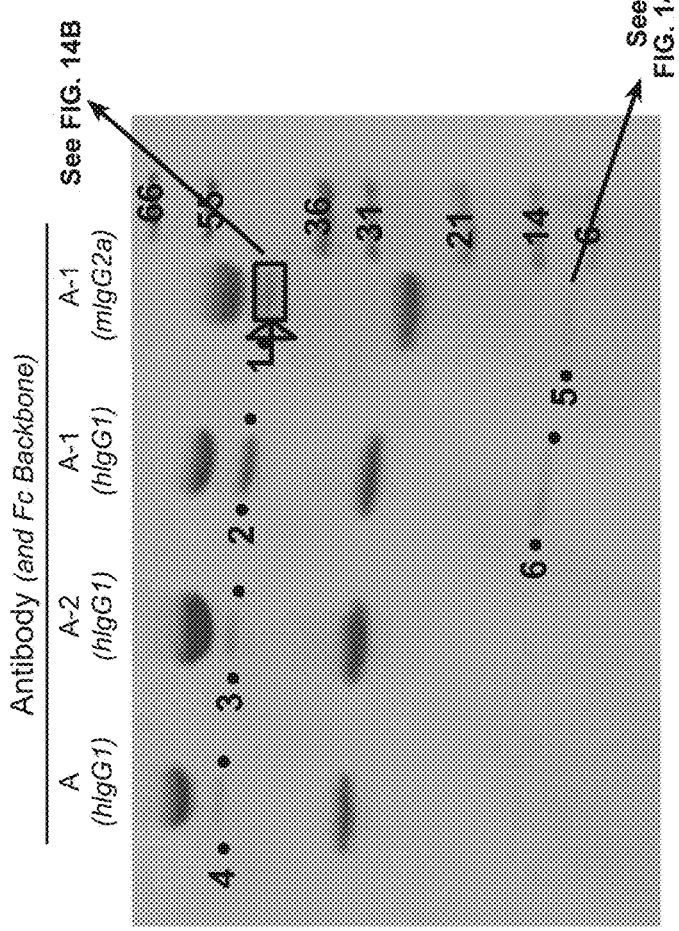

FIG. 14A

Sequence Data Results

| Cycle/Run | 1/3 | 2/4 | 3/5 | 4/6 | 5/7 | 6/8 | 7/9 | 8/10 | 9/11 | 10/12 | 11/13 | 12/14 | 13/15 | 14/16 | 15/17 |
|---|---|---|---|---|---|---|---|---|---|---|---|---|---|---|---|
| Sequence 1 | S 0.527 | L 0.785 | F | A 0.745 | Y 1.177 | - | G 0.166 | Q 0.377 | G 0.206 | T 0.231 | L 0.241 | V 0.231 | (T) 0.162 | V 0.109 | - |

SEQ ID NO: 109 p1.PUR42676

```
  1 MGWSCIILFLVATATGAYAEVQLVESGGGLVQPGGSLRLSCAASGFTFSNYGIHWVRQAPGKGLEWVGWITPDGGYTDYA
 81 DSVKGRFTISADTSKNTAYLQMNSLRAEDTAVYYCARAGSLFAYWGQGTLVTVSSASTKGPSVYPLAPVCGDTTGSSVTL
                                            ----- 120 -----
161 GCLVKGYFPEPVTLTWNSGSLSSGVHTFPAVLQSDLYTLSSSVTVTSSTWPSQSITCNVAHPASSTKVDKKIEPRGPTIK
241 PCPPCKCPAPNLLGGPSVFIFPPKIKDVLMISLSPIVTCVVVDVSEDDPDVQISWFVNNVEVHTAQTQTHREDYNSTLRV
321 VSALPIQHQDWMSGKEFKCKVNNKDLPAPIERTISKPKGSVRAPQVYVLPPPEBEMTKKQVTLTCMVTDFMPEDIYVEWT
401 NNGKTELNYKNTEPVLDSDGSYFMYSKLRVEKKNWVERNSYSCSVVHEGLHNHHTTKSFSRTPGKMGWSCIILFLVATAT
481 GVHSDIQMTQSPSSLSASVGDRVTITCRASQDVSTAVAWYQQKPGKAPKLLIYSASFLYSGVPSRFSGSGSGTDFTLTIS
561 SLQPEDFATYYCQQYYTTATTFGQGTKVEIKRADAAPTVSIFPPSSEQLTSGGASVVCFLNNFYPKDINVKWKIDGSERQ
641 NGVLNSWTDQDSKDSTYSMSSTLTLTKDEYERHNSYTCEATHKTSTSPIVKSFNRNEC
```

SEQ ID NO: 110

*FIG. 14B*

Sequence Data Results

| Cycle/Run | 1/20 | 2/21 | 3/22 | 4/23 | 5/24 | 6/25 | 7/26 | 8/27 | 9/28 | 10/29 | 11/30 | 12/31 | 13/32 | 14/33 | 15/34 |
|---|---|---|---|---|---|---|---|---|---|---|---|---|---|---|---|
| Sequence 1 | E 0.704 | V 0.761 | Q 0.500 | L 0.754 | V 0.579 | E 0.411 | S 0.319 | G 0.473 | G 0.573 | G 0.632 | L 0.380 | V 0.238 | Q 0.265 | P 0.443 | G | p1.PUR42676

```
  1  MGWSCIILFLVATATGAYAEVQLVESGGGLVQPGGSLRLSCAASGFTFSNYGIHWVRQAPGKGLEWVGWITPDGGYTDYA
                          |_____0_____|
 81  DSVKGRFTISADTSKNTAYLQMNSLRAEDTAVYYCARAGSLFAVWGQGTLVTVSSASTKGPSVYPLAPVCGDTTGSSVTL
161  GCLVKGYFPEPVTLTWNSGSLSSGVHTFPAVLQSDLYTLSSSVTVTSSTWPSQSITCNVAHPASSTKVDKKIEPRGPTIK
241  PCPPCKCPAPNLLGGPSVFIFPPKIKDVLMISLSPIVTCVVVDVSEDDPDVQISWFVNNVEVHTAQTQTHREDYNSTLRV
321  VSALPIQHQDWMSGKEFKCKVNNKDLPAPIERTISKPKGSVRAPQVYVLPPPEEEMTKKQVTLLTCMVTDFMPEDIYVEWT
401  NNGKTELNYKNTEPVLDSDGSYFMYSKLRVEKKNWVERNSYSCSVVHEGLHNHHTTKSFSRTPGKMGWSCIILFLVATAT
481  GVHSDIQMTQSPSSLSASVGDRVTITCRASQDVSTAVAWYQQKPGKAPKLLIYSASFLYSGVPSRFSGSGSGTDFTLTIS
561  SLQPEDFATYYCQQYYTTATTFGQGTKVEIKRADAAPTVSIFPPSSEQLTSGGASVVCFLNNFYPKDINVKWKIDGSERQ
641  NGVLNSWTDQDSKDSTYSMSSTLTLTKDEYERHNSYTCEATHKTSTSPIVKSFNRNEC                    SEQ ID NO: 110
```

SEQ ID NO: 111

*FIG. 14C*

CDR Sequences According to Kabat Definition are Underlined

Light Chain Variable Region

| Kabat Number | 1 2 3 4 5 6 7 8 9 10 11 12 13 14 15 16 17 18 19 20 21 22 23 | 24 25 26 27 28 29 30 31 32 33 34 35 36 37 38 39 40 41 42 |
|---|---|---|
| A-1 (S101T) | D I Q M T Q S P S S L S A S V G D R V T I T C | R A S Q D V S T A V A W Y Q Q K P G K |

CDR L1 - Contact: 27-34
CDR L1 - Chothia: 24-34 (approx)
CDR L1 - Kabat: 24-34

| Kabat Number | 43 44 45 46 47 48 49 50 51 52 53 54 55 56 57 58 59 60 61 62 63 64 65 66 67 68 69 70 71 72 73 74 75 76 77 78 79 80 81 82 83 84 |
|---|---|
| A-1 (S101T) | A P K L L I Y S A S F L Y S G V P S R F S G S G S G T D F T L T I S S L Q P E D F A |

CDR L2 - Contact
CDR L2 - Chothia
CDR L2 - Kabat

| Kabat Number | 85 86 87 88 89 90 91 92 93 94 95 96 97 98 99 100 101 102 103 104 105 106 107 |
|---|---|
| A-1 (S101T) | T Y Y C Q Q Y Y T T T F G Q G T K V E I K     SEQ ID NO: 34 |

CDR L3 - Contact
CDR L3 - Chothia
CDR L3 - Kabat

*FIG. 22A*

Heavy Chain Variable Region

| Kabat Number | 1 2 3 4 5 6 7 8 9 10 11 12 13 14 15 16 17 18 19 20 21 22 23 | 24 25 26 27 28 29 30 31 32 33 34 35 36 37 38 39 40 41 42 |
|---|---|---|
| A-1 (S101T) | E V Q L V E S G G G L V Q P G G S L R L S C A A S G | F T F S N Y G I H W V R Q A P G |

CDR H1 - Contact
CDR H1 - Chothia
CDR H1 - Kabat

| Kabat Number | 43 44 45 46 47 48 49 50 51 52 52a 53 54 55 56 57 58 59 60 61 62 63 64 65 66 67 68 69 70 71 72 73 74 75 76 77 78 79 80 81 82 82a |
|---|---|
| A-1 (S101T) | K G L E W V G W I T P D G G Y T D Y A D S V K G R F T I S A D T S K N T A V Y L Q M N |

CDR H2 - Contact
CDR H2 - Chothia
CDR H2 - Kabat

| Kabat Number | 82b 82c 83 84 85 86 87 88 89 90 91 92 93 94 95 96 97 98 99 100 101 102 103 104 105 106 107 108 109 110 111 112 113 |
|---|---|
| A-1 (S101T) | S L R A E D T A V Y Y C A R A G T L F A Y W G Q G T L V T V S S     SEQ ID NO: 33 |

CDR H3 - Contact
CDR H3 - Chothia
CDR H3 - Kabat

*FIG. 22B*

ANTI-JAGGED1 ANTIBODIES AND METHODS OF USE

FIELD OF THE INVENTION

The present invention relates to anti-Jagged antibodies and methods of using the same.

BACKGROUND

The Notch signaling pathway regulates a diverse array of cell functions (Kopan et al., *Cell* 137, 216-233 (2009)). Four Notch receptors have been identified in mammals, i.e., Notch 1-4, that share basic structural elements that include an extracellular domain, a transmembrane domain, and an intracellular domain. Similarly, the canonical ligands of Notch share certain structural similarities but a number of non-canonical ligands of Notch have also been identified (Kopan et al., *Cell* 137, 216-233 (2009)). The five canonical ligands in mammals are Delta-like 1, Delta-like 3, Delta-like 4, Jagged1 and Jagged2. Binding of a Notch ligand to the extracellular domain of a Notch receptor sets a signaling cascade in motion that begins with proteolytic cleavage at the extracellular S2 site by an alpha secretase of the ADAM (a disintegrin and metalloprotease) family. Cleavage at S2 is followed by proteolytic cleavage by a gamma secretase at the intracellular S3 site, which results in release of the intracellular domain and downstream events that ultimately activate Notch-dependent transcription factors such as Hes1 and Hey.

Aberrant Notch expression and signaling has been implicated in a number of diseases, including cancer (Koch et al., *Cell. Mol. Life Sci.* 64, 2746-2762 (2007)). It is clear that there continues to be a need for agents that have clinical attributes that are optimal for development as therapeutic agents. The invention described herein meets this need and provides other benefits.

SUMMARY

The invention provides anti-Jagged1 antibodies and methods of using the same.

The present inventors unexpectedly found that anti-Jagged1 antibody A-1 (see FIG. 4 and PCT Publication No. 2014/028446) is cleaved in the heavy chain following heat treatment and/or freeze-thaw conditions. The poor stability of the antibody potentially reduces its value as a therapeutic. Analysis of the cleavage site revealed no known protease cleavage motifs. It was therefore not known whether changes to the antibody sequence could reduce the observed cleavage. Further, because the cleavage site is in a heavy chain HVR, even if amino acid change(s) would reduce cleavage, it was not known whether such changes could be made without significantly reducing the antibody's affinity for Jagged1. The inventors found, surprisingly, that mutation of the amino acid at position 101 in HVR-H3 reduced cleavage with only a slight loss of affinity.

In some embodiments, an isolated antibody that binds to human Jagged1 is provided, wherein the antibody comprises an HVR-H3 comprising the amino acid sequence of SEQ ID NO: 55 or 59, wherein X is any amino acid other than S. In some embodiments, the antibody comprises at least one, at least two, at least three, at least four, or five HVRs selected from HVR-H1 comprising the amino acid sequence of SEQ ID NO: 35 or 78; HVR-H2 comprising the amino acid sequence of SEQ ID NO: 28 or 36; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16 or 40. In some embodiments, the antibody comprises (a) HVR-H1 comprising the amino acid sequence of SEQ ID NO: 78; HVR-H2 comprising the amino acid sequence of SEQ ID NO: 36; and HVR-H3 comprising the amino acid sequence of SEQ ID NO: 55; or (b) HVR-H1 comprising the amino acid sequence of SEQ ID NO: 78; HVR-H2 comprising the amino acid sequence of SEQ ID NO: 36; and HVR-H3 comprising the amino acid sequence of SEQ ID NO: 59; or (c) HVR-H1 comprising the amino acid sequence of SEQ ID NO: 78; HVR-H2 comprising the amino acid sequence of SEQ ID NO: 28; and HVR-H3 comprising the amino acid sequence of SEQ ID NO: 59. In any of the embodiments described herein, the antibody may comprise (a) HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40; or (b) HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16; or (c) HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

In some embodiments, an isolated antibody that binds to Jagged1 comprises (a) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 55; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40; or (b) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 59; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16; or (c) HVR-H1 comprising the amino acid sequence of SEQ ID NO: 78; HVR-H2 comprising the amino acid sequence of SEQ ID NO: 28; HVR-H3 comprising the amino acid sequence of SEQ ID NO: 59; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

In some embodiments, an isolated antibody that binds to Jagged1 comprises a VH sequence having at least 95% identity to the amino acid sequence of SEQ ID NO: 54, 58, or 62. In some embodiments, an isolated antibody that binds to Jagged1 comprises a VL sequence having at least 95% identity to the amino acid sequence of SEQ ID NO: 10, 26, or 34. In some embodiments, the antibody comprises (a) a VH sequence having at least 95% identity to the amino acid sequence of SEQ ID NO: 54 and a VL sequence having at least 95% identity to the amino acid sequence of SEQ ID NO: 34; or (b) a VH sequence having at least 95% identity to the amino acid sequence of SEQ ID NO: 58 and a VL sequence having at least 95% identity to the amino acid sequence of SEQ ID NO: 10; or (c) a VH sequence having at least 95% identity to the amino acid sequence of SEQ ID NO: 62 and a VL sequence having at least 95% identity to the amino acid sequence of SEQ ID NO: 26.

In some embodiments, an isolated antibody that binds to human Jagged1 comprises (a) a VH sequence of SEQ ID NO: 54, wherein X is any amino acid other than S, and a VL sequence of SEQ ID NO: 34; or (b) a VH sequence of SEQ ID NO: 58, wherein X is any amino acid other than S, and a VL sequence of SEQ ID NO: 10; or (c) a VH sequence of SEQ ID NO: 62, wherein X is any amino acid other than S, and a VL sequence of SEQ ID NO: 26. In some embodiments, the antibody comprises a VH sequence of SEQ ID NO: 54 and a VL sequence of SEQ ID NO: 34. In some embodiments, the heavy chain comprises the amino acid sequence of SEQ ID NO: 56 and the light chain comprises the amino acid sequence of SEQ ID NO: 53. In some embodiments, the heavy chain comprises the amino acid sequence of SEQ ID NO: 57 and the light chain comprises the amino acid sequence of SEQ ID NO: 53.

In any of the embodiments described herein, X may be any amino acid other than S or H. In any of the embodiments described herein, X may be selected from A, D, E, G, I, K, L, N, Q, R T, and V. In any of the embodiments described herein, X may be T.

In some embodiments, an isolated antibody that binds human Jagged1 is provided, comprising (a) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 37; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40; or (b) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 64; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16; or (c) HVR-H1 comprising the amino acid sequence of SEQ ID NO: 78; HVR-H2 comprising the amino acid sequence of SEQ ID NO: 28; HVR-H3 comprising the amino acid sequence of SEQ ID NO: 64; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

In some embodiments, an isolated antibody that binds human Jagged1 is provided, comprising (a) a VH sequence of SEQ ID NO: 33 and a VL sequence of SEQ ID NO: 34; or (b) a VH sequence of SEQ ID NO: 65 and a VL sequence of SEQ ID NO: 10; or (c) a VH sequence of SEQ ID NO: 66 and a VL sequence of SEQ ID NO: 26. In some embodiments, the antibody comprises a VH sequence of SEQ ID NO: 33 and a VL sequence of SEQ ID NO: 34.

In any of the above embodiments described herein, the antibody may be a monoclonal antibody. In certain embodiments, the antibody is a human, humanized, or chimeric antibody. In any of the above embodiments described herein, the antibody may be an antibody fragment.

Any of the above embodiments may be a full-length IgG1 antibody. In some embodiments, the antibody is an IgG1 antibody lacking effector function. In some embodiments, the antibody is an IgG1 antibody comprising an N297G or N297A mutation. In some embodiments, the antibody is an IgG1 antibody comprising an N297G mutation.

In some embodiments, an isolated antibody that binds to Jagged1 is provided, wherein the heavy chain comprises the amino acid sequence of SEQ ID NO: 51 and the light chain comprises the amino acid sequence of SEQ ID NO: 53. In some embodiments, the heavy chain comprises the amino acid sequence of SEQ ID NO: 52 and the light chain comprises the amino acid sequence of SEQ ID NO: 53. In some embodiments, the antibody comprises (a) a heavy chain comprising the amino acid sequence of SEQ ID NO: 69 and a light chain comprising the amino acid sequence of SEQ ID NO: 75; or (b) a heavy chain comprising the amino acid sequence of SEQ ID NO: 70 and a light chain comprising the amino acid sequence of SEQ ID NO: 76; or (c) a heavy chain comprising the amino acid sequence of SEQ ID NO: 79 and a light chain comprising the amino acid sequence of SEQ ID NO: 75; or (d) a heavy chain comprising the amino acid sequence of SEQ ID NO: 80 and a light chain comprising the amino acid sequence of SEQ ID NO: 76.

In any of the embodiments described herein, the antibody may be an antagonist of Jagged1-mediated signaling. In some embodiments, the antibody binds human and murine Jagged1. In some embodiments, the antibody binds human, murine, rat, and cynomolgus monkey Jagged1. In some embodiments, the antibody binds Jagged1 but does not bind Jagged2. In some embodiments, the antibody binds human Jagged1 does not bind human Jagged2. In some embodiments, the antibody binds human and murine Jagged1 but does not bind human or murine Jagged2. In some embodiments, the antibody binds human, murine, rat, and cynomolgus monkey Jagged1 but does not bind human, cynomolgus monkey, or murine Jagged2. In some embodiments, the antibody binds Jagged1 but does not bind Jagged2 or DLL1. In some embodiments, the antibody binds human Jagged1 but does not bind human Jagged2 or human DLL1. In some embodiments, the antibody the antibody binds human and murine Jagged1 but does not bind human or murine Jagged2 or human or murine DLL1. In some embodiments, the antibody the antibody binds human, murine, and cynomolgus monkey Jagged1 but does not bind human, murine, or cynomolgus monkey Jagged2 or human, murine, or cynomolgus monkey DLL1. In some embodiments, the antibody binds Jagged1 but does not bind Jagged2, DLL1, or DLL4. In some embodiments, the antibody binds human Jagged1 but does not bind human Jagged2, human DLL1, or human DLL4. In some embodiments, the antibody binds human and murine Jagged1 but does not bind human or murine Jagged2, human or murine DLL1, or human or murine DLL4. In some embodiments, the antibody binds human, murine, rat, and cynomolgus monkey Jagged1 but does not bind human, murine, or cynomolgus monkey Jagged2, human, murine, or cynomolgus monkey DLL1, or human, murine, or cynomolgus monkey DLL4.

In some embodiments, the antibody binds human Jagged1 with an affinity (Kd) of 2 nM or stronger (i.e., less than 2 nM). In some embodiments, the antibody binds human Jagged1 with an affinity (Kd) of 1.5 nM or stronger, or 1 nM or stronger, or 0.9 nM or stronger, 0.8 nM or stronger, or 0.7 nM or stronger (i.e., less than 1.5 nM, less than 1 nM, less than 0.9 nM, less than 0.8 nM, or less than 0.7 nM). In some embodiments, the antibody binds murine Jagged1 with an affinity (Kd) of 2 nM or stronger (i.e., less than 2 nM). In some embodiments, the antibody binds murine Jagged1 with an affinity (Kd) of 1.5 nM or stronger, or 1 nM or stronger, or 0.9 nM or stronger, 0.8 nM or stronger, 0.7 nM or stronger, or 0.6 nM or stronger, or 0.5 nM or stronger (i.e., less than 1.5 nM, less than 1 nM, less than 0.9 nM, less than 0.8 nM, less than 0.7 nM, less than 0.6 nM, or less than 0.5 nM). In some embodiments, affinity (Kd) is measured using surface plasmon resonance.

In some embodiments, the antibody binds human Jagged1 with an association constant ($k_{on}$) of at least 1.0E+04/Ms, or at least 1.5E+04/Ms, or at least 2.0E+04/Ms. In some embodiments, the antibody binds human Jagged1 with a dissociation constant ($k_{off}$) of less than 10.0E-04/s, or less than 9.0E-04/s, or less than 8.0E-04/s, or less than 7.0E-04/s. In some embodiments, the antibody binds murine Jagged1 with an association constant ($k_{on}$) of at least 1.0E+04/Ms, or at least 1.5E+04/Ms, or at least 2.0E+04/Ms, or at least 3.0E+04/Ms, or at least 4.0E+04/Ms, or at least 5.0E+04/Ms, or at least 6.0E+04/Ms, or at least 7.0E+04/Ms. In some embodiments, the antibody binds murine Jagged1 with a dissociation constant ($k_{off}$) of less than 10.0E-04/s, or less than 9.0E-04/s, or less than 8.0E-04/s, or less than 7.0E-04/s. In some embodiments, association and dissociation constants are measured using surface plasmon resonance.

In some embodiments, the antibody binds native, folded Jagged1, but does not bind denatured Jagged1. In some embodiments, the antibody binds Jagged1 in an enzyme-linked immunosorbent assay (ELISA) but does not bind Jagged1 on a Western blot. In some embodiments, the antibody binds folded Jagged1 in an enzyme-linked immunosorbent assay (ELISA) but does not bind denatured Jagged1 on a Western blot. In some embodiments, the antibody binds folded Jagged1 under physiological conditions but does not bind denatured Jagged1.

In some embodiments, the antibody reduces tumor growth in a mouse xenograft model without causing weight loss. In some embodiments, the mouse xenograft model is a liver cancer xenograft model. In some embodiments, tumor growth is reduced by at least 50, at least 60, at least 70, at least 80, or at least 90 AUC/day TGI %.

In some embodiments, use of the Jagged1 antibody reduces goblet cell metaplasia in lungs in a mouse model of airway hyperresponsiveness. In some embodiments, administration of the antibody reduces the number of goblet cells in the lungs by at least 30%, at least 40%, at least 50%, at least 60%, at least 70%, at least 80%, or at least 90%. In another aspect, the invention provides an isolated antibody that competes with any of the above embodiments for specific binding to Jagged1. In some embodiments, an antibody is that competes for binding to human Jagged1 with an antibody comprising a heavy chain variable region comprising the sequence of SEQ ID NO: 33 and a light chain variable region comprising the sequence of SEQ ID NO: 34, wherein the antibody is not antibody A, antibody A-1, or antibody A-2.

In another aspect, the invention provides an isolated nucleic acid encoding an isolated antibody of the above embodiments. In a further aspect, the invention provides a host cell comprising the isolated nucleic acid encoding the antibody. In a further aspect, the invention provides a method of producing an antibody comprising culturing the host cell so that the antibody is produced.

In another aspect, the invention provides an immunoconjugate comprising an antibody of any of the above embodiments and a cytotoxic agent.

In another aspect, the invention provides a pharmaceutical formulation comprising an antibody of any of the above embodiments and a pharmaceutically acceptable carrier.

In another aspect, an antibody of any of the above embodiments is provided for use as a medicament. In some embodiments, an antibody of any of the above embodiments is provided for use in treating a cancer. In some embodiments, an antibody of any of the above embodiments is provided for use in reducing cancer cell growth.

In another aspect, a method of inhibiting Jagged1-mediated signaling is provided. In one embodiment, a method of inhibiting Jagged1-mediated signaling in vitro is provided. In one embodiment, a method of inhibiting Jagged1-mediated signaling in vivo is provided.

In another aspect, a method of treating an individual having a cancer comprising administering to the individual an effective amount of an antibody of any of the above embodiments. In one embodiment, the cancer is selected from the group consisting of: breast cancer, lung cancer, brain cancer, cervical cancer, colon cancer, liver cancer, bile duct cancer, pancreatic cancer, skin cancer, B-cell malignancies, and T-cell malignancies.

The present inventors discovered that treatment with Jagged1-antibody biases cell fate in the airways away from a secretory cell (including goblet cell) fate and toward a ciliated cell fate. Jagged1 signaling is important for maintaining the secretory cell fate, and inhibition of Jagged1 signaling prevented goblet cell metaplasia. The present inventors also showed that the club cell-to-ciliated cell conversion is direct and did not involve cell division (data not shown). This transdifferentiation of one cell type to another occurred in the adult lung and is distinct from cell fate choices that involve progenitor cell division, such as after damage or during development. Goblet cell metaplasia or excess mucus is a hallmark of several airway diseases, such as asthma, cystic fibrosis, COPD and Barrett's esophagus. These Jagged inhibition results provide the basis for therapeutic applications involving use of Jagged1 or Jagged2 inhibitors for prevention or reversal of goblet cell metaplasia and for treatment of conditions characterized by excess mucus, as in airway diseases (e.g., asthma, COPD, cystic fibrosis) and Barrett's esophagus.

In some embodiments, provided are methods of converting a club cell to a ciliated cell, comprising administering an antagonist antibody that binds to human Jagged1 (including, but not limited to, any of the anti-Jagged1 antibodies described herein) to an individual. In some embodiments, provided are methods of increasing conversion of club cells into ciliated cells, comprising administering an antagonist antibody that binds to human Jagged1 (including, but not limited to, any of the anti-Jagged1 antibodies described herein) to an individual. In some embodiments, the club cell is present in the adult human airway (e.g., lung). In some embodiments, the conversion occurs in the absence of club cell division. In some embodiments, the individual has a disease selected from allergy, asthma, autoimmune disease, diseases associated with goblet cell metaplasia (e.g., in lung) and diseases associated with excess mucus. In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, provided are methods of decreasing the number of goblet cells, comprising administering an antagonist antibody that binds to human Jagged1 (including, but not limited to, any of the anti-Jagged1 antibodies described herein) to an individual. In some embodiments, provided are methods of reducing conversion of club cells into goblet cells, comprising administering an antagonist antibody that binds to human Jagged1 (including, but not limited to, any of the anti-Jagged1 antibodies described herein) to an individual. In some embodiments, the goblet cell(s) is present in the adult human airway (e.g., lung). In some embodiments, the individual has a disease selected from allergy, asthma, autoimmune disease, diseases associated with goblet cell metaplasia (e.g., in lung) and diseases associated with excess mucus. In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, provided are methods of reducing the formation of goblet cells in a subject, comprising administering an antagonist antibody that binds to human Jagged1 (including, but not limited to, any of the anti-Jagged1 antibodies described herein) to an individual. In some embodiments, formation of goblet cells in the adult human airway (e.g., lung) is reduced. In some embodiments, the individual has a disease selected from allergy, asthma, autoimmune disease, diseases associated with goblet cell metaplasia (e.g., in lung) and diseases associated with excess mucus. In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, provided are methods of decreasing mucus, comprising administering an antagonist antibody that binds to human Jagged1 (including, but not limited to, any of the anti-Jagged1 antibodies described herein) to an individual. In some embodiments, the mucus is airway mucus. In some embodiments, the mucus is present in adult human airway (e.g., lung). In some embodiments, the individual has a disease selected from allergy, asthma, autoimmune disease, diseases associated with goblet cell metaplasia (e.g., in lung) and diseases associated with excess mucus. In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, provided are methods of increasing ciliated cell number, comprising administering an antagonist antibody that binds to human Jagged1 (including, but not limited to, any of the anti-Jagged1 antibodies described herein) to an individual. In some embodiments, provided are methods of increasing formation of ciliated cells, comprising administering an antagonist antibody that binds to human Jagged1 (including, but not limited to, any of the anti-Jagged1 antibodies described herein) to an individual. In some embodiments, the ciliated cell is present in the adult human airway (e.g., lung). In some embodiments, the individual has a disease selected from allergy, asthma, autoimmune disease, diseases associated with goblet cell metaplasia (e.g., in lung) and diseases associated with excess mucus. In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein. In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein, wherein the antibody that binds to human Jagged1 increases conversion of club cells to ciliated cells in the adult human airway (e.g., lung). In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein, wherein the antibody that binds to human Jagged1 decreases the number of goblet cells in the adult human airway (e.g., lung). In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein, wherein the antibody that binds to human Jagged1 reduces the formation of goblet cells in the adult human airway (e.g., lung). In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein, wherein the antibody that binds to human Jagged1 decreases mucus in the adult human airway (e.g., lung). In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein, wherein the antibody that binds to human Jagged1 increases ciliated cell number in the adult human airway (e.g., lung). In some embodiments, the disease is associated with goblet cell metaplasia. In some embodiments, the disease is selected from asthma, chronic obstructive pulmonary disease (COPD), cystic fibrosis, and Barrett's esophagus.

In some embodiments, an antibody that binds to human Jagged1 (including, for example, any of the anti-Jagged1 antibodies described herein) is provided for use in treating a disease selected from allergy, asthma, autoimmune disease, diseases associated with goblet cell metaplasia (e.g., in lung) and diseases associated with excess mucus is provided, comprising administering to an individual with cancer an effective amount of an antibody of any of the embodiments described herein, wherein the antibody that binds to human Jagged1 increases formation of ciliated cells in the adult human airway (e.g., lung). In some embodiments, the disease is associated with goblet cell metaplasia. In some embodiments, the disease is selected from asthma, chronic obstructive pulmonary disease (COPD), cystic fibrosis, and Barrett's esophagus.

In another aspect, provided are methods of (a) converting a ciliated cell to a club cell (e.g., wherein the ciliated cell is found in the adult human airway, e.g., lung), (b) increasing mucus (e.g., airway mucus), (c) decreasing ciliated cell number (e.g., human airway ciliated cell), comprising administering an agonist of Jagged signaling to an individual.

In some embodiments, a method of treating a disease selected from allergy, asthma, autoimmune disease, diseases associated with goblet cell metaplasia (e.g., in lung) and diseases associated with excess mucus is provided, comprising administering to an individual with cancer an effective amount of antibody that binds to human Jagged1 (including, for example, any of the antibodies that bind to human Jagged1 described herein). In some embodiments, the disease is associated with goblet cell metaplasia (e.g., in the lung). In some embodiments, the disease is selected from asthma, chronic obstructive pulmonary disease (COPD), cystic fibrosis, and Barrett's esophagus.

In any of the embodiments described herein, wherein the Jagged1 antibody reduces tumor growth in a mouse xenograft model without causing weight loss.

In any of the embodiments described herein, the anti-Jagged1 antibody may be conjugated to a label. In some embodiments, the label is a positron emitter. In some embodiments, the positron emitter is $^{89}$Zr. In some embodiments, a method of detecting human Jagged1 in a biological sample is provided, comprising contacting the biological sample with an antibody described herein under conditions permissive for binding of the antibody to a naturally occurring human Jagged1, and detecting whether a complex is formed between the antibody and a naturally occurring human Jagged1 in the biological sample. In some embodiments, the biological sample is selected from breast cancer, lung cancer, brain cancer, cervical cancer, colon cancer, liver cancer, bile duct cancer, pancreatic cancer, skin cancer, B-cell malignancies, and T-cell malignancies.

BRIEF DESCRIPTION OF THE FIGURES

FIG. 1 shows exemplary amino acid sequences of human and murine Jagged1 protein.

FIG. 2 shows exemplary amino acid sequences of human and murine Jagged2 protein.

FIGS. 3A-D show the amino acid sequences of peptides used for phage antibody library screening and selection. All proteins were expressed as a secreted protein in BEVS cells and their sequences are listed in the N-terminal to C-terminal direction. (A) Amino acid sequence of expressed protein murine Jagged 1-DSL-EGF1-4 (Q34-D377). The bold font at the N-terminus represents a short linker sequence (ADLGS) (SEQ ID NO: 82). The bold font at the C-terminus represents a short linker sequence (EFG), a thrombin cleavage site (LVPRGS) (SEQ ID NO: 83), a G spacer and the 6-His tag. (B) Amino acid sequence of expressed protein human Jag1-DSL-EGF1-4. Only the Jag1 sequence is shown although the antigen also contained a TEV protease cleavage site and 6-His tag at the C-terminus. (C) Amino acid sequence of expressed protein murine Jag2-DSL-EGF1-4 (M27-E388). The bold font at the N-terminus represents a short linker sequence (ADLGS) (SEQ ID NO: 82). The bold font at the C-terminus represents a short linker sequence (EFG), a thrombin cleavage site (LVPRGS) (SEQ ID NO: 83), a G spacer and the 6-His tag. (D) Amino acid sequence of expressed protein human Jag2-DSL-EGF1-4 (R2-E388). The bold font at the C-terminus represents a short linker sequence (EFG), a thrombin cleavage site (LVPRGS) (SEQ ID NO: 83), a G spacer and the 6-His tag.

Figure 4A-1:
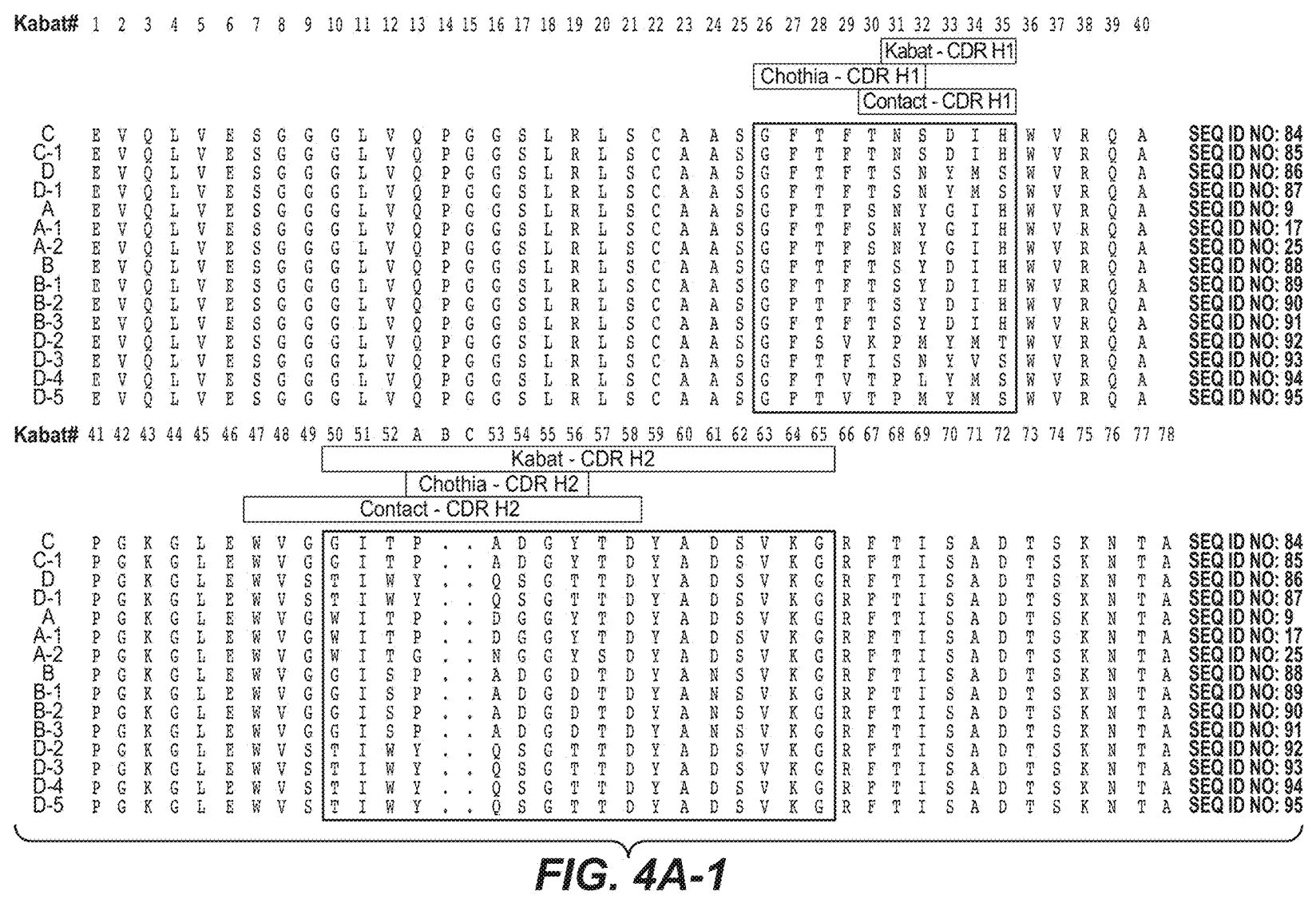
Figure 4A-2:
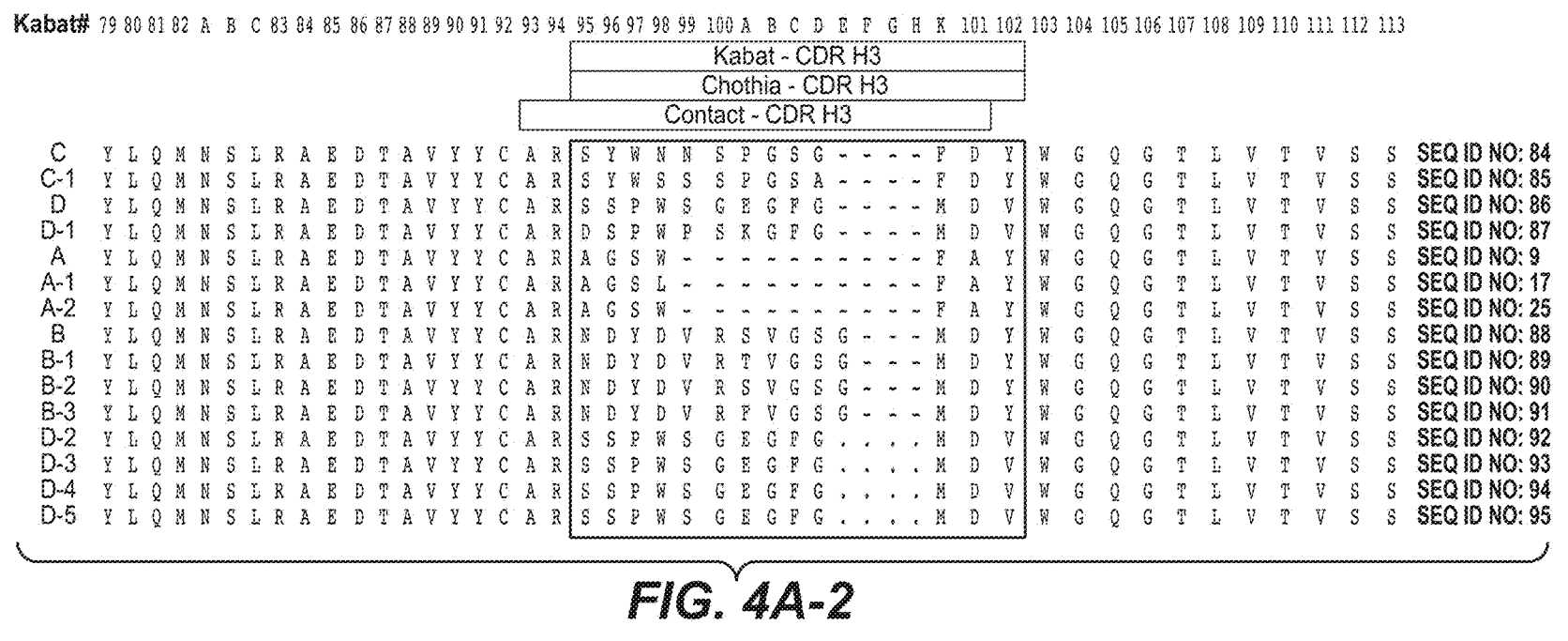
Figure 4B-1:
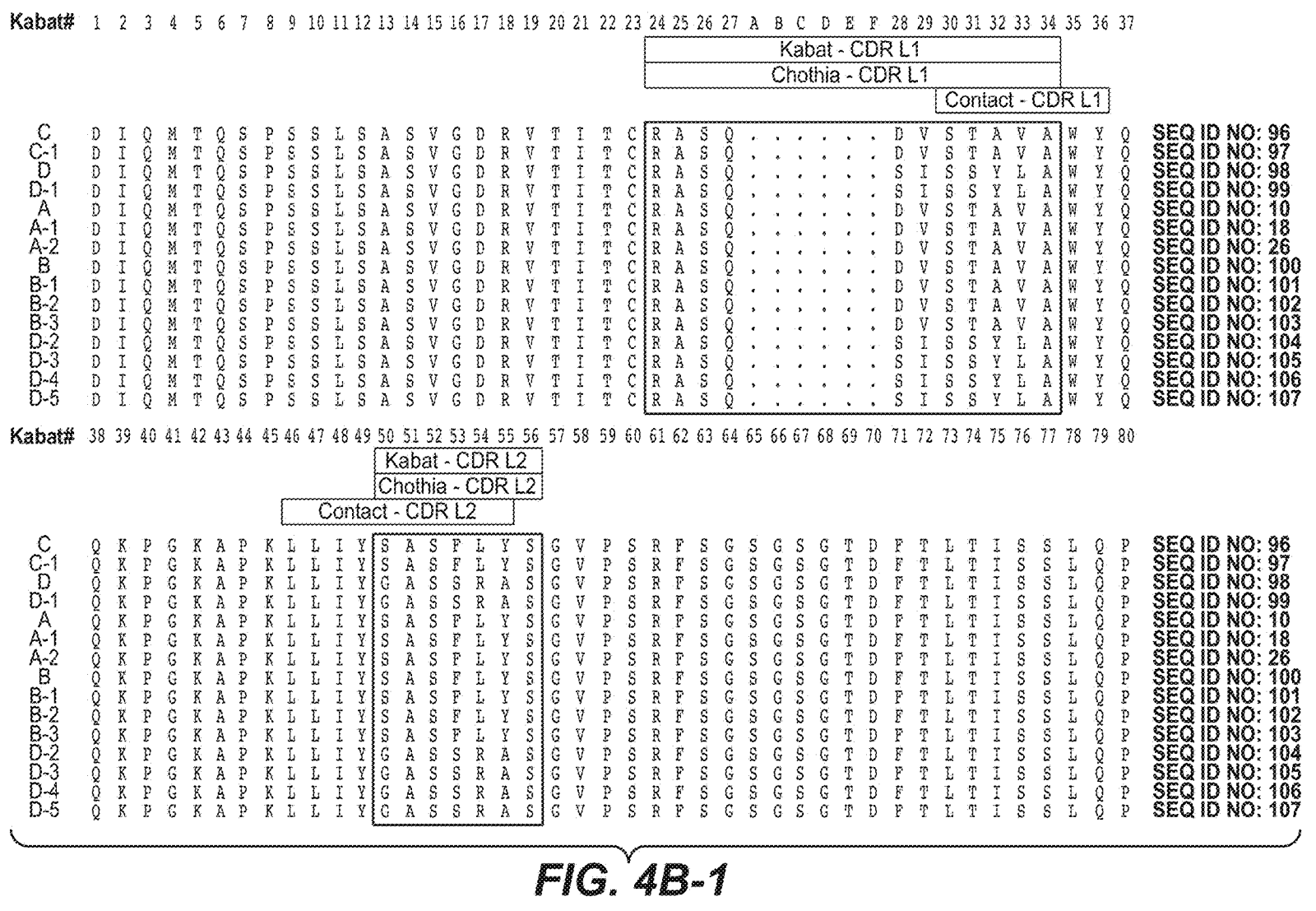
Figure 4B-2:
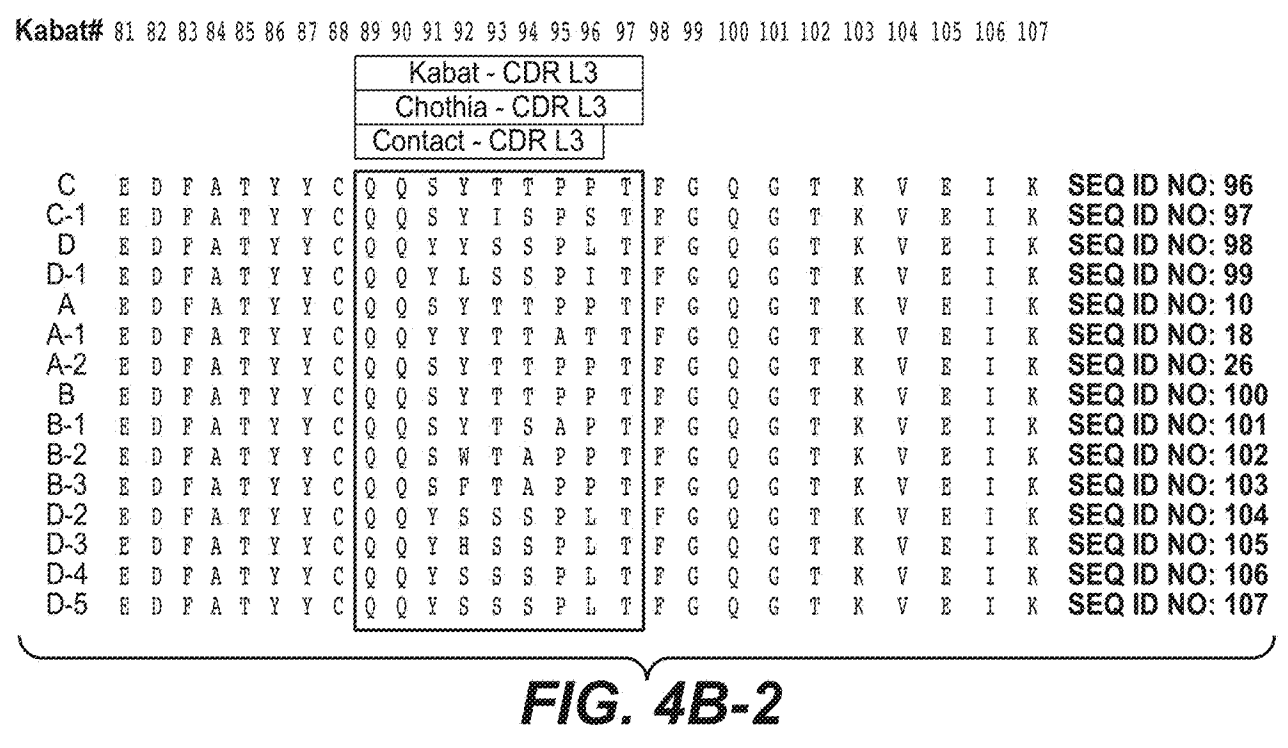

FIGS. 4A-1-B-2 show an alignment of the amino acid sequences for the heavy (FIG. 4A-1 and FIG. 4A-2) and light (FIG. 4B-1 and FIG. 4B-2) chain variable domains of anti-Jagged1 (A, A-1, A-2), anti-Jagged2 (B, B-1, B-2, B-3), and anti-Jagged1/2 antibodies (C, C-1, D, D-1, D-2, D-3, D-4, D-5). Amino acid positions of the complementarity determining regions (CDRs) are indicated.

FIGS. 5A-B show the H1, H2, and H3 heavy chain hypervariable region (HVR) sequences of anti-Jagged1 antibodies, as described in the Examples. Amino acid positions are numbered according to the Kabat numbering system as described herein and elsewhere.

FIG. 6 shows the L1, L2, and L3 light chain HVR sequences of anti-Jagged1 antibodies described in the Examples. Amino acid positions are numbered according to the Kabat numbering system as described below.

FIG. 7 shows light and heavy chain framework sequences of anti-Jagged1 antibodies described in the Examples. Numbers in superscript indicate amino acid positions according to Kabat.

FIGS. 11A-1-B-2 show inhibition of human lung cancer cell growth by an anti-Jagged1 antagonist antibody in vivo. Mice bearing human lung cancer xenografts were injected twice per week intraperitoneally (IP) with 20 mpk anti-gD isotype control antibody (Isotype control Ab) or with anti-Jagged1 antibody A-2 (Anti-Jag1), with the injections starting after average tumor volumes (measured with calipers) reached approximately 180 mm³. Tumor volumes (y-axis) were subsequently measured for 19 days. FIG. 11A-1 and FIG. 11A-2: The average tumor volumes for each group (n=10) were plotted over time (x-axis) using a linear mixed effects model (FIG. 11A-1). Tumor volumes for each mouse in each group are depicted in the two panels in FIG. 11A-2. FIG. 11B-1 and FIG. 11B-2: Total body weight of each mouse was measured and graphed as the percentage change averaged for each group (FIG. 11B-1) or for each mouse in each group (FIG. 11B-2).

FIGS. 13A-C show cleavage of the anti-Jagged1 antibodies in the heavy chain. (A) Antibodies A, A-1 and A-2 were analyzed by standard SDS-PAGE and protein staining methods in the absence (−) or presence (+) of the reducing agent DTT, as indicated. Molecular mass standards (in kD) are also shown. Panel (B) displays a representative scan of a mass spectrometry (MS) analysis (LC-MS/TOF, reducing conditions) of A-1. The positions of the relevant fragments (peaks) are annotated, and the molecular masses are shown above the peaks. This analysis indicated that the cleavage site was between HC amino acids G100 and S101 in CDR3, as diagramed in the HC amino acid sequence in panel (C), with the arrow marking the cleavage position.

FIGS. 14A-C shows N-terminal peptide sequencing of the anti-Jagged1 antibody heavy chain cleavage site. Following the standard methods for SDS-PAGE under reducing conditions and protein staining, the full-length and cleaved fragments of the indicated antibody preparations were separated and identified (A). The C-terminal (B) and N-terminal (C) cleaved peptide fragments were cut out of the gel and sequenced using standard methods for peptide N-terminal sequencing to precisely identify the site of cleavage. The underlined sequences in panels (B) and (C) note the N-terminal sequences of each of the peptides sequenced, with the sequence in panel (B) marking the cleavage site and the sequence in panel (C) marking the N-terminus of the HC.

FIGS. 22A-B show the amino acid sequences for the (A) heavy chain and (B) light chain variable domains of anti-Jagged1 antibody A-1(S101T). Amino acid positions of the complementarity determining regions (CDRs) are indicated.

DETAILED DESCRIPTION OF EMBODIMENTS OF THE INVENTION

I. Definitions

Figure 8:
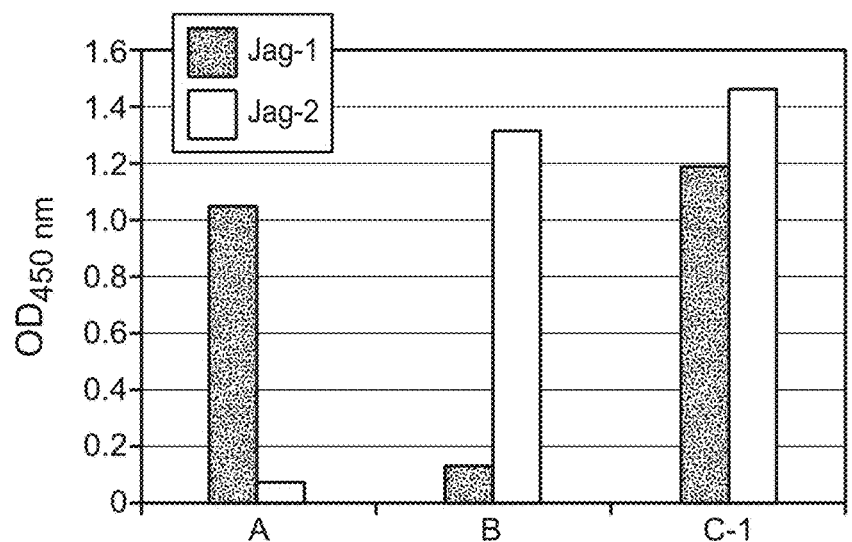
FIG. 8 shows binding specificity of antibodies obtained from the screening. Results of ELISA assays measuring binding specificity of Antibodies A and B, identified during screening using human Jag1-DSL-EGF1-4 (FIG. 3B) for antibody A and murine and human Jag2-DSL-EGF1-4 (FIGS. 3C and D) for antibody B. Black columns=binding to human Jagged1; gray columns=binding to human Jagged2. C-1 is an antibody that binds to both Jagged1 and Jagged2.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Jagged antibody" and "an antibody that binds to Jagged" refer to an antibody that is capable of binding Jagged1, Jagged2, or Jagged1 and 2 (Jagged1/2) with sufficient affinity such that the antibody is useful as a diagnostic and/or therapeutic agent in targeting Jagged. In one embodiment, the extent of binding of an anti-Jagged antibody to an unrelated, non-Jagged protein is less than about 10% of the binding of the antibody to Jagged as measured, e.g., by a radioimmunoassay (RIA). In certain embodiments, an antibody that binds to Jagged has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$ M to $10^{-13}$ M). In certain embodiments, an anti-Jagged antibody binds to an epitope of Jagged that is conserved among Jagged from different species. The terms "anti-Jagged1 antibody" and "an antibody that binds to Jagged1" refer to an antibody that is capable of binding Jagged1 with sufficient affinity such that the antibody is useful as a diagnostic and/or therapeutic agent in targeting Jagged1.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

As used herein, "asthma" refers to a complex disorder characterized by variable and recurring symptoms, reversible airflow obstruction (e.g., by bronchodilator) and bronchial hyperresponsiveness which may or may not be associated with underlying inflammation. Examples of asthma include aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids and other asthmas as mentioned in J Allergy Clin Immunol (2010) 126(5):926-938.

A "blocking" antibody or an "antagonist" antibody is one which significantly inhibits (either partially or completely) a biological activity of the antigen it binds.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Jagged antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Figures 1, 11A:
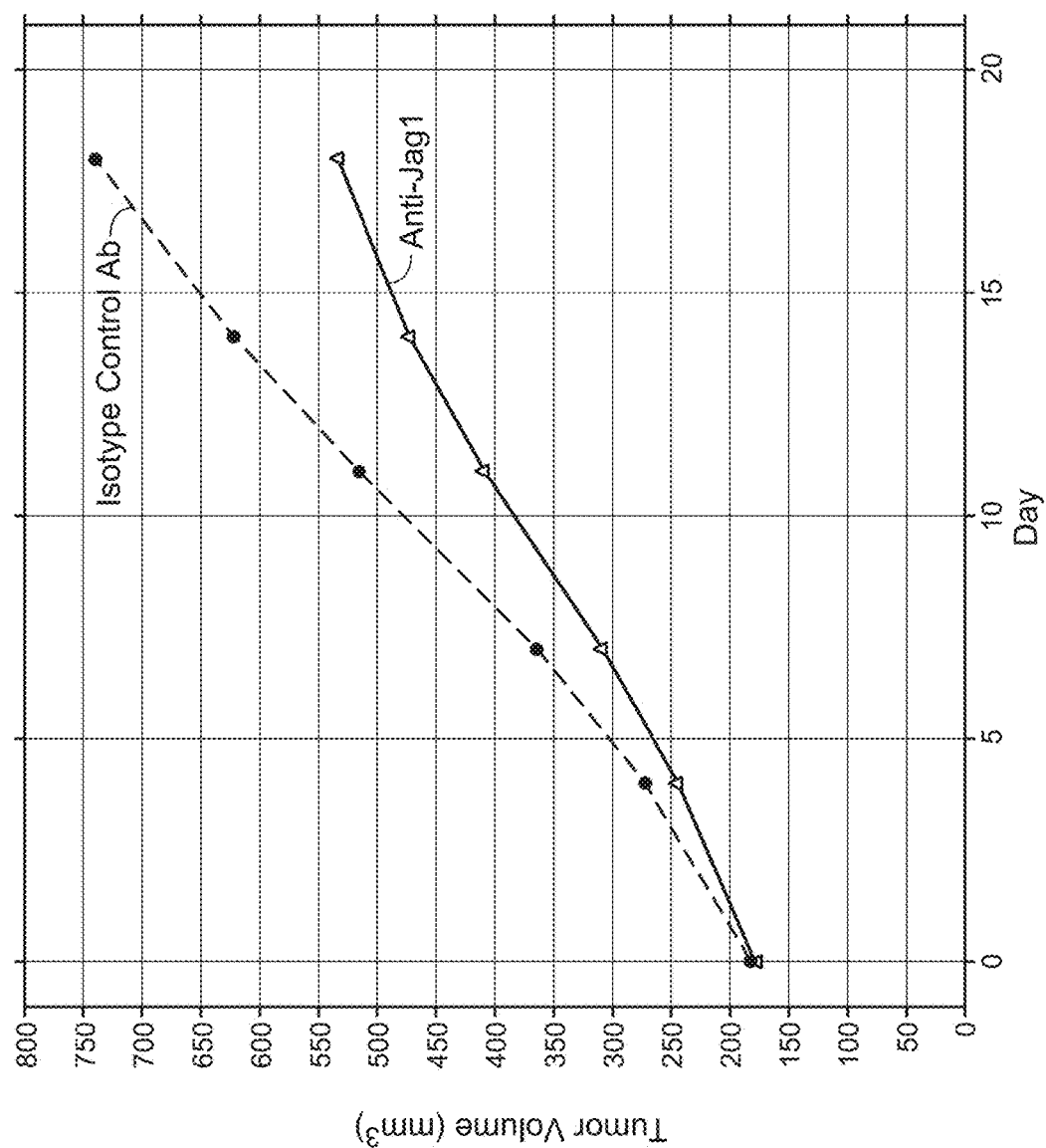
Figures 2, 11A:
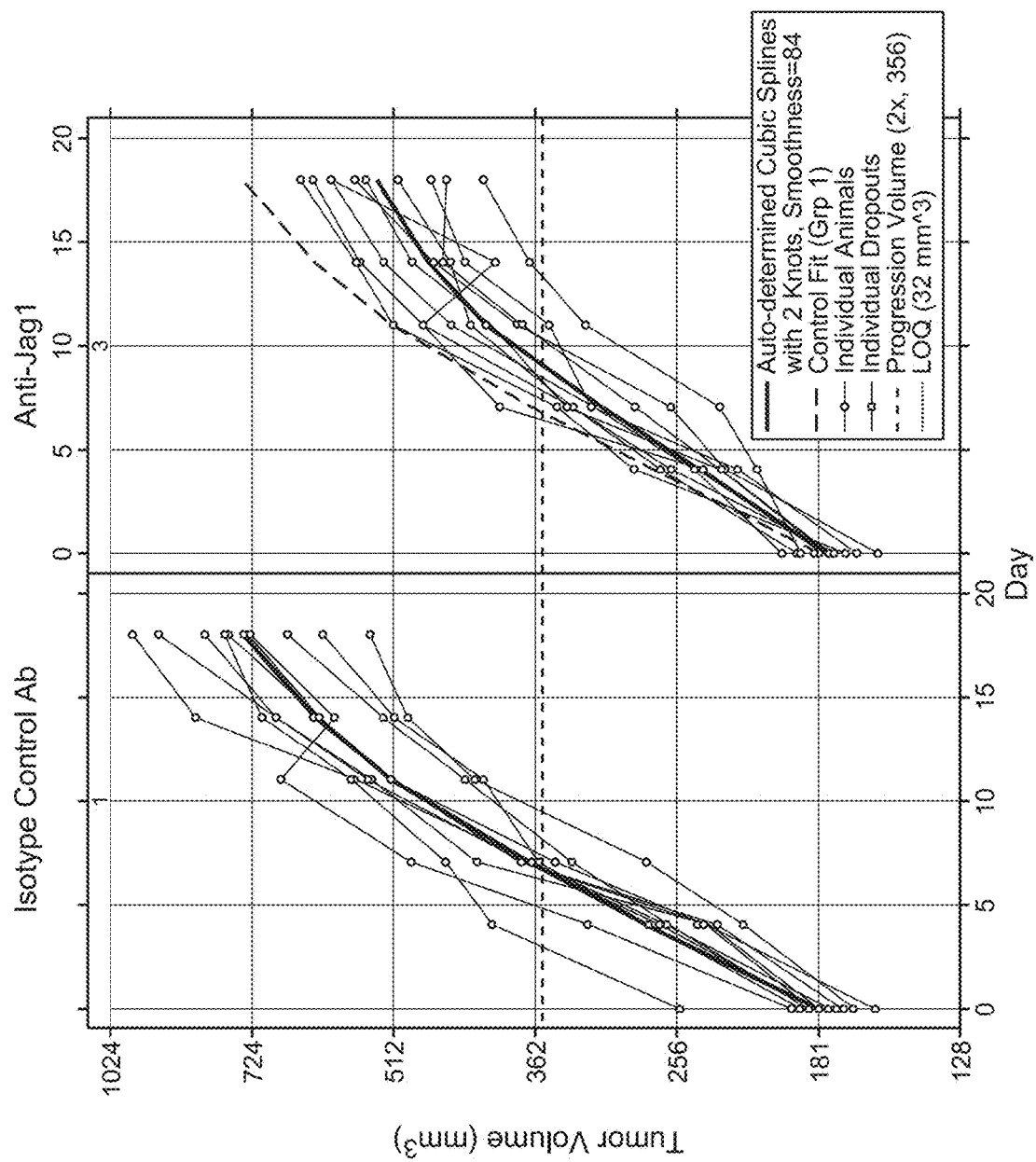

The term "Jagged" or "Jag," as used herein, refers to any native Jagged from any vertebrate source, including mammals such as primates (e.g. humans) and rodents (e.g., mice and rats), unless otherwise indicated. The term encompasses "full-length," unprocessed Jagged as well as any form of Jagged that results from processing in the cell. The term also encompasses naturally occurring variants of Jagged, e.g., splice variants or allelic variants. The amino acid sequence of an exemplary human and murine Jagged1 and Jagged2 is shown in FIGS. 1 and 2 (SEQ ID NOS:1-4), respectively.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the identification of anti-Jagged antibodies and fragments thereof. In certain embodiments, antibodies that bind to at least one Jagged are provided. Antibodies of the invention are useful, e.g., for the diagnosis or treatment of cancer. Accordingly, the invention provides methods, compositions, kits, and articles of manufacture related to anti-Jagged antibodies.

A. Exemplary Anti-Jagged1 Antibodies

In one aspect, the invention provides isolated antibodies that bind to Jagged1. In some embodiments, the antibody is an antagonist of Jagged1-mediated signaling. In some embodiments, the antibody binds human and murine Jagged1. In some embodiments, the antibody binds human, murine, and cynomolgus monkey Jagged1. In some embodiments, the antibody binds Jagged1 but does not bind Jagged2. In some embodiments, the antibody binds human Jagged1 does not bind human Jagged2. In some embodiments, the antibody binds human and murine Jagged1 but does not bind human or murine Jagged2. In some embodiments, the antibody binds human, murine, and cynomolgus monkey Jagged1 but does not bind human, cynomolgus monkey, or murine Jagged2. In some embodiments, the antibody binds Jagged1 but does not bind Jagged2 or DLL1. In some embodiments, the antibody binds human Jagged1 but does not bind human Jagged2 or human DLL1. In some embodiments, the antibody the antibody binds human and murine Jagged1 but does not bind human or murine Jagged2 or human or murine DLL1. In some embodiments, the antibody the antibody binds human, murine, and cynomolgus monkey Jagged1 but does not bind human, murine, or cynomolgus monkey Jagged2 or human, murine, or cynomolgus monkey DLL1. In some embodiments, the antibody binds Jagged1 but does not bind Jagged2, DLL1, or DLL4. In some embodiments, the antibody binds human Jagged1 but does not bind human Jagged2, human DLL1, or human DLL4. In some embodiments, the antibody binds human and murine Jagged1 but does not bind human or murine Jagged2, human or murine DLL1, or human or murine DLL4. In some embodiments, the antibody binds human, murine, and cynomolgus monkey Jagged1 but does not bind human, murine, or cynomolgus monkey Jagged2, human, murine, or cynomolgus monkey DLL1, or human, murine, or cynomolgus monkey DLL4.

In some embodiments, the antibody binds human Jagged1 with an affinity (Kd) of 2 nM or stronger (i.e., less than 2 nM). In some embodiments, the antibody binds human Jagged1 with an affinity (Kd) of 1.5 nM or stronger, or 1 nM or stronger, or 0.9 nM or stronger, 0.8 nM or stronger, or 0.7 nM or stronger (i.e., less than 1.5 nM, less than 1 nM, less than 0.9 nM, less than 0.8 nM, or less than 0.7 nM). In some embodiments, the antibody binds murine Jagged1 with an affinity (Kd) of 2 nM or stronger (i.e., less than 2 nM). In some embodiments, the antibody binds murine Jagged1 with an affinity (Kd) of 1.5 nM or stronger, or 1 nM or stronger, or 0.9 nM or stronger, 0.8 nM or stronger, 0.7 nM or stronger, or 0.6 nM or stronger, or 0.5 nM or stronger (i.e., less than 1.5 nM, less than 1 nM, less than 0.9 nM, less than 0.8 nM, less than 0.7 nM, less than 0.6 nM, or less than 0.5 nM).

In some embodiments, the antibody binds native, folded Jagged1, but does not bind denatured Jagged1. In some embodiments, the antibody binds Jagged1 in an enzyme-linked immunosorbent assay (ELISA) but does not bind Jagged1 on a Western blot. In some embodiments, the antibody binds folded Jagged1 in an enzyme-linked immunosorbent assay (ELISA) but does not bind denatured Jagged1 on a Western blot. In some embodiments, the antibody binds folded Jagged1 under physiological conditions but does not bind denatured Jagged1. "Native, folded" Jagged1 refers to Jagged1 that has undergone protein folding under physiological conditions and has been maintained in a folded state. In some embodiments, Jagged1 has been maintained in a folded state in solution.

In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 28 or 36; (c) HVR-H3 comprising the amino acid sequence of SEQ ID NO: 55 or 59, wherein X is any amino acid other than S; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 16 or 40. In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 36; (c) HVR-H3 comprising the amino acid sequence of SEQ ID NO: 55, wherein X is any amino acid other than S; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 40. In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 28; (c) HVR-H3 comprising the amino acid sequence of SEQ ID NO: 59, wherein X is any amino acid other than S; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 16. In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 36; (c) HVR-H3 comprising the amino acid sequence of SEQ ID NO: 59, wherein X is any amino acid other than S; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 16. In some embodiments, X is any amino acid other than S. In some embodiments, X is any amino acid other than S or H. In some embodiments, X is selected from A, D, E, G, I, K, L, N, Q, R T, and V. In some embodiments, X is T.

In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 40. In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 28; (c) HVR-H3 comprising the amino acid sequence of SEQ ID NO: 64; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 16. In some embodiments, the invention provides an anti-Jagged1 antibody comprising at least one, two, three, four, five, or six HVRs selected from (a) HVR-H1 comprising the amino acid sequence of SEQ ID NO: 35 or 78; (b) HVR-H2 comprising the amino acid sequence of SEQ ID NO: 36; (c) HVR-H3 comprising the amino acid sequence of SEQ ID NO: 64; (d) HVR-L1 comprising the amino acid sequence of SEQ ID NO: 38; (e) HVR-L2 comprising the amino acid sequence of SEQ ID NO: 39; and (f) HVR-L3 comprising the amino acid sequence of SEQ ID NO: 16.

In one aspect, the invention provides an antibody comprising at least one, at least two, or all three VH HVR sequences selected from (a) HVR-H1 comprising the amino acid sequence of SEQ ID NO: 35 or 78; (b) HVR-H2 comprising the amino acid sequence of SEQ ID NO: 28 or 36; and (c) HVR-H3 comprising the amino acid sequence of SEQ ID NO: 55 or 59, wherein X is any amino acid other than S. In one embodiment, the antibody comprises HVR-H3 comprising the amino acid sequence of SEQ ID NO: 55 or 59, wherein X is any amino acid other than S. In another embodiment, the antibody comprises HVR-H3 comprising the amino acid sequence of SEQ ID NO: 55 or 59, wherein X is any amino acid other than S and HVR-L3 comprising the amino acid sequence of SEQ ID NO: 16 or 40. In a further embodiment, the antibody comprises HVR-H3 comprising the amino acid sequence of SEQ ID NO: 55 or 59, wherein X is any amino acid other than S, HVR-L3 comprising the amino acid sequence of SEQ ID NO: 16 or 40, and HVR-H2 comprising the amino acid sequence of SEQ ID NO: 28 or 36. In a further embodiment, the antibody comprises (a) HVR-H1 comprising the amino acid sequence of SEQ ID NO: 35 or 78; (b) HVR-H2 comprising the amino acid sequence of SEQ ID NO: 28 or 36; and (c) HVR-H3 comprising the amino acid sequence of SEQ ID NO: 55 or 59, wherein X is any amino acid other than S. In some embodiments, X is any amino acid other than S. In some embodiments, X is any amino acid other than S or H. In some embodiments, X is selected from A, D, E, G, I, K, L, N, Q, R T, and V. In some embodiments, X is T.

In one aspect, the invention provides an antibody comprising at least one, at least two, or all three VH HVR sequences selected from (a) HVR-H1 comprising the amino acid sequence of SEQ ID NO: 35 or 78; (b) HVR-H2 comprising the amino acid sequence of SEQ ID NO: 36; and (c) HVR-H3 comprising the amino acid sequence of SEQ ID NO: 55, wherein X is any amino acid other than S. In one embodiment, the antibody comprises HVR-H3 comprising the amino acid sequence of SEQ ID NO: 55, wherein X is any amino acid other than S. In another embodiment, the antibody comprises HVR-H3 comprising the amino acid sequence of SEQ ID NO: 55, wherein X is any amino acid other than S and HVR-L3 comprising the amino acid sequence of SEQ ID NO: 40. In a further embodiment, the antibody comprises HVR-H3 comprising the amino acid sequence of SEQ ID NO: 55, wherein X is any amino acid other than S, HVR-L3 comprising the amino acid sequence of SEQ ID NO: 40, and HVR-H2 comprising the amino acid sequence of SEQ ID NO: 36. In a further embodiment, the antibody comprises (a) HVR-H1 comprising the amino acid sequence of SEQ ID NO: 35 or 78; (b) HVR-H2 comprising the amino acid sequence of SEQ ID NO: 36; and (c) HVR-H3 comprising the amino acid sequence of SEQ ID NO: 55, wherein X is any amino acid other than S. In some embodiments, X is any amino acid other than S. In some embodiments, X is any amino acid other than S or H. In some embodiments, X is selected from A, D, E, G, I, K, L, N, Q, R T, and V. In some embodiments, X is T. In a further embodiment, the antibody comprises (a) HVR-H1 comprising the amino acid sequence of SEQ ID NO: 35 or 78; (b) HVR-H2 comprising the amino acid sequence of SEQ ID NO: 36; and (c) HVR-H3 comprising the amino acid sequence of SEQ ID NO: 37.

In one aspect, the invention provides an antibody comprising at least one, at least two, or all three VH HVR sequences selected from (a) HVR-H1 comprising the amino acid sequence of SEQ ID NO: 35 or 78; (b) HVR-H2 comprising the amino acid sequence of SEQ ID NO: 28; and (c) HVR-H3 comprising the amino acid sequence of SEQ ID NO: 59, wherein X is any amino acid other than S. In one embodiment, the antibody comprises HVR-H3 comprising the amino acid sequence of SEQ ID NO: 59, wherein X is any amino acid other than S. In another embodiment, the antibody comprises HVR-H3 comprising the amino acid sequence of SEQ ID NO: 59, wherein X is any amino acid other than S and HVR-L3 comprising the amino acid sequence of SEQ ID NO: 16. In a further embodiment, the antibody comprises HVR-H3 comprising the amino acid sequence of SEQ ID NO: 59, wherein X is any amino acid other than S, HVR-L3 comprising the amino acid sequence of SEQ ID NO: 16, and HVR-H2 comprising the amino acid sequence of SEQ ID NO: 28. In a further embodiment, the antibody comprises (a) HVR-H1 comprising the amino acid sequence of SEQ ID NO: 35 or 78; (b) HVR-H2 comprising the amino acid sequence of SEQ ID NO: 28; and (c) HVR-H3 comprising the amino acid sequence of SEQ ID NO: 59, wherein X is any amino acid other than S. In some embodiments, X is any amino acid other than S. In some embodiments, X is any amino acid other than S or H. In some embodiments, X is selected from A, D, E, G, I, K, L, N, Q, R T, and V. In some embodiments, X is T. In a further embodiment, the antibody comprises (a) HVR-H1 comprising the amino acid sequence of SEQ ID NO: 35 or 78; (b) HVR-H2 comprising the amino acid sequence of SEQ ID NO: 28; and (c) HVR-H3 comprising the amino acid sequence of SEQ ID NO: 64.

In one aspect, the invention provides an antibody comprising at least one, at least two, or all three VH HVR sequences selected from (a) HVR-H1 comprising the amino acid sequence of SEQ ID NO: 35 or 78; (b) HVR-H2 comprising the amino acid sequence of SEQ ID NO: 36; and (c) HVR-H3 comprising the amino acid sequence of SEQ ID NO: 59, wherein X is any amino acid other than S. In one embodiment, the antibody comprises HVR-H3 comprising the amino acid sequence of SEQ ID NO: 59, wherein X is any amino acid other than S. In another embodiment, the antibody comprises HVR-H3 comprising the amino acid sequence of SEQ ID NO: 59, wherein X is any amino acid other than S and HVR-L3 comprising the amino acid sequence of SEQ ID NO: 16. In a further embodiment, the antibody comprises HVR-H3 comprising the amino acid sequence of SEQ ID NO: 59, wherein X is any amino acid other than S, HVR-L3 comprising the amino acid sequence of SEQ ID NO: 16, and HVR-H2 comprising the amino acid sequence of SEQ ID NO: 36. In a further embodiment, the antibody comprises (a) HVR-H1 comprising the amino acid sequence of SEQ ID NO: 35 or 78; (b) HVR-H2 comprising the amino acid sequence of SEQ ID NO: 36; and (c) HVR-H3 comprising the amino acid sequence of SEQ ID NO: 59, wherein X is any amino acid other than S. In some embodiments, X is any amino acid other than S. In some embodiments, X is any amino acid other than S or H. In some embodiments, X is selected from A, D, E, G, I, K, L, N, Q, R T, and V. In some embodiments, X is T. In a further embodiment, the antibody comprises (a) HVR-H1 comprising the amino acid sequence of SEQ ID NO: 35 or 78; (b) HVR-H2 comprising the amino acid sequence of SEQ ID NO: 36; and (c) HVR-H3 comprising the amino acid sequence of SEQ ID NO: 64.

In another aspect, the invention provides an antibody comprising at least one, at least two, or all three VL HVR sequences selected from (a) HVR-L1 comprising the amino acid sequence of SEQ ID NO: 38; (b) HVR-L2 comprising the amino acid sequence of SEQ ID NO: 39; and (c) HVR-L3 comprising the amino acid sequence of SEQ ID NO: 16 or 40. In one embodiment, the antibody comprises (a) HVR-L1 comprising the amino acid sequence of SEQ ID NO: 38; (b) HVR-L2 comprising the amino acid sequence of SEQ ID NO: 39; and (c) HVR-L3 comprising the amino acid sequence of SEQ ID NO: 16 or 40. In one embodiment, the antibody comprises (a) HVR-L1 comprising the amino acid sequence of SEQ ID NO: 38; (b) HVR-L2 comprising the amino acid sequence of SEQ ID NO: 39; and (c) HVR-L3 comprising the amino acid sequence of SEQ ID NO: 16. In one embodiment, the antibody comprises (a) HVR-L1 comprising the amino acid sequence of SEQ ID NO: 38; (b) HVR-L2 comprising the amino acid sequence of SEQ ID NO: 39; and (c) HVR-L3 comprising the amino acid sequence of SEQ ID NO: 40.

In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 28 or 36, and (iii) HVR-H3 comprising an amino acid sequence selected from SEQ ID NO: 55 or 59, wherein X is any amino acid other than S; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16 or 40. In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 55, wherein X is any amino acid other than S; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 40. In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 28, and (iii) HVR-H3 comprising an amino acid sequence selected from SEQ ID NO: 59, wherein X is any amino acid other than S; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16. In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 59, wherein X is any amino acid other than S; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16. In some embodiments, X is any amino acid other than S. In some embodiments, X is any amino acid other than S or H. In some embodiments, X is selected from A, D, E, G, I, K, L, N, Q, R T, and V.

In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 28 or 36, and (iii) HVR-H3 comprising an amino acid sequence selected from SEQ ID NO: 55 or 59, wherein X is any amino acid other than S; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16 or 40. In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 55, wherein X is any amino acid other than S; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 40. In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 28, and (iii) HVR-H3 comprising an amino acid sequence selected from SEQ ID NO: 59, wherein X is any amino acid other than S; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16. In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 59, wherein X is any amino acid other than S; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16. In some embodiments, X is any amino acid other than S. In some embodiments, X is any amino acid other than S or H. In some embodiments, X is selected from A, D, E, G, I, K, L, N, Q, R T, and V.

In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 37; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 40. In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 28, and (iii) HVR-H3 comprising an amino acid sequence selected from SEQ ID NO: 64; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16. In another aspect, an antibody of the invention comprises (a) a VH domain comprising at least one, at least two, or all three VH HVR sequences selected from (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 64; and (b) a VL domain comprising at least one, at least two, or all three VL HVR sequences selected from (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16.

In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 37; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 40. In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 28, and (iii) HVR-H3 comprising an amino acid sequence selected from SEQ ID NO: 64; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16. In another aspect, an antibody of the invention comprises (a) a VH domain comprising (i) HVR-H1 comprising the amino acid sequence of SEQ ID NO: 35 or 78, (ii) HVR-H2 comprising the amino acid sequence of SEQ ID NO: 36, and (iii) HVR-H3 comprising an amino acid sequence selected from SEQ ID NO: 64; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 16.

In some embodiments, an anti-Jagged1 antibody comprises (a) a VH domain comprising (i) HVR-H1 comprising the amino acid sequence of SEQ ID NO: 35 or 78, (ii) HVR-H2 comprising the amino acid sequence of SEQ ID NO: 71, wherein X1 is selected from P and G, X2 is selected from D and N, and X3 is selected from T and S, and (iii) HVR-H3 comprising an amino acid sequence selected from SEQ ID NO: 72, wherein X1 is any amino acid other than S, and X2 is W or L; and (b) a VL domain comprising (i) HVR-L1 comprising the amino acid sequence of SEQ ID NO: 38, (ii) HVR-L2 comprising the amino acid sequence of SEQ ID NO: 39, and (c) HVR-L3 comprising the amino acid sequence of SEQ ID NO: 74, wherein X1 is S or Y, X2 is P or A, and X3 is P or T. In some embodiments, the X1 in SEQ ID NO: 72 is any amino acid other than S or H. In some embodiments, the X1 in SEQ ID NO: 72 is selected from A, D, E, G, I, K, L, N, Q, R T, and V. In some embodiments, the X1 in SEQ ID NO: 72 is T.

In one embodiment, an anti-Jagged1 antibody comprises HVRs as in any of the above embodiments, and further comprises an acceptor human framework, e.g. a human immunoglobulin framework or a human consensus framework. In another embodiment, an anti-Jagged1 antibody comprises HVRs as in any of the above embodiments, and further comprises a VH comprising at least one, two, three, or four FRs selected from an FR1 comprising the amino acid sequence of SEQ ID NO: 47; an FR2 comprising the amino acid sequence of SEQ ID NO: 48; an FR3 comprising the amino acid sequence of SEQ ID NO: 49; and an FR4 comprising the amino acid sequence of SEQ ID NO: 50. In another embodiment, an anti-Jagged1 antibody comprises HVRs as in any of the above embodiments, and further comprises a VL comprising at least one, two, three, or four FRs selected from an FR1 comprising the amino acid sequence of SEQ ID NO: 43; an FR2 comprising the amino acid sequence of SEQ ID NO: 44; an FR3 comprising the amino acid sequence of SEQ ID NO: 45; and an FR4 comprising the amino acid sequence of SEQ ID NO: 46.

In another aspect, an anti-Jagged1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 54, 58, or 62, wherein X is any amino acid other than S. In some such embodiments, the VH sequence comprises an HVR-H3 of SEQ ID NO: 55 or 59, wherein X is any amino acid other than S. In some embodiments, the VH comprises one, two or three HVRs selected from: (a) HVR-H1 comprising the amino acid sequence of SEQ ID NO: 35 or 78, (b) HVR-H2 comprising the amino acid sequence of SEQ ID NO: 55 or 59, wherein X is any amino acid other than S, and (c) HVR-H3 comprising the amino acid sequence of SEQ ID NO: 37 or 64. In some embodiments, X is any amino acid other than S. In some embodiments, X is any amino acid other than S or H. In some embodiments, X is selected from A, D, E, G, I, K, L, N, Q, R T, and V. In some embodiments, X is T. In another aspect, an anti-Jagged1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 33, 65, or 66. In some such embodiments, the VH sequence comprises an HVR-H3 of SEQ ID NO: 37 or 64. In some embodiments, the VH comprises one, two or three HVRs selected from: (a) HVR-H1 comprising the amino acid sequence of SEQ ID NO: 35 or 78, (b) HVR-H2 comprising the amino acid sequence of SEQ ID NO: 28 or 36, and (c) HVR-H3 comprising the amino acid sequence of SEQ ID NO: 37 or 64. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Jagged1 antibody comprising that sequence retains the ability to bind to at least one Jagged1. In certain embodiments, substitutions, insertions, or deletions occur in regions outside the HVRs (i.e., in the FR5). In certain embodiments, an anti-Jagged1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 33. In some such embodiments, the VH sequence comprises an HVR-H3 of SEQ ID NO: 37. In some embodiments, the VH comprises one, two or three HVRs selected from: (a) HVR-H1 comprising the amino acid sequence of SEQ ID NO: 35 or 78, (b) HVR-H2 comprising the amino acid sequence of SEQ ID NO: 36, and (c) HVR-H3 comprising the amino acid sequence of SEQ ID NO: 37. In some embodiments, the anti-Jagged1 antibody comprises the VH sequence in SEQ ID NO: 33, 65, or 66, including post-translational modifications of that sequence. In some embodiments, the anti-Jagged1 antibody comprises the VH sequence in SEQ ID NO: 33, including post-translational modifications of that sequence. In some embodiments, the anti-Jagged1 antibody comprises the VH sequence in SEQ ID NO: 65, including post-translational modifications of that sequence. In some embodiments, the anti-Jagged1 antibody comprises the VH sequence in SEQ ID NO: 66, including post-translational modifications of that sequence.

In another aspect, an anti-Jagged1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10, 26, or 34. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Jagged1 antibody comprising that sequence retains the ability to bind to Jagged1. In certain embodiments, a total of 1 to 10 amino acids have been substituted, inserted and/or deleted in SEQ ID NO: 10, 26, or 34. In certain embodiments, the substitutions, insertions, or deletions occur in regions outside the HVRs (i.e., in the FR5). In some embodiments, the VL comprises one, two or three HVRs selected from (a) HVR-L1 comprising the amino acid sequence of SEQ ID NO: 38; (b) HVR-L2 comprising the amino acid sequence of SEQ ID NO: 39; and (c) HVR-L3 comprising the amino acid sequence of SEQ ID NO: 16 or 40. In some embodiments, the anti-Jagged1 antibody comprises the VL sequence in SEQ ID NO: 10, 26, or 34, including post-translational modifications of that sequence. In some embodiments, the anti-Jagged1 antibody comprises the VL sequence in SEQ ID NO: 34, including post-translational modifications of that sequence. In some embodiments, the anti-Jagged1 antibody comprises the VL sequence in SEQ ID NO: 10, including post-translational modifications of that sequence. In some embodiments, the anti-Jagged1 antibody comprises the VL sequence in SEQ ID NO: 26, including post-translational modifications of that sequence.

In another aspect, an anti-Jagged1 antibody is provided, wherein the antibody comprises a VH as in any of the embodiments provided above, and a VL as in any of the embodiments provided above. In one embodiment, the antibody comprises the VH and VL sequences in SEQ ID NO: 54, wherein X is any amino acid other than S; and SEQ ID NO: 34, respectively, including post-translational modifications of those sequences. In one embodiment, the antibody comprises the VH and VL sequences in SEQ ID NO: 58, wherein X is any amino acid other than S; and SEQ ID NO: 10, respectively, including post-translational modifications of those sequences. In one embodiment, the antibody comprises the VH and VL sequences in SEQ ID NO: 62, wherein X is any amino acid other than S; and SEQ ID NO: 26, respectively, including post-translational modifications of those sequences. In some embodiments, X is any amino acid other than S. In some embodiments, X is any amino acid other than S or H. In some embodiments, X is selected from A, D, E, G, I, K, L, N, Q, R T, and V. In some embodiments, X is T.

In another aspect, an anti-Jagged1 antibody is provided, wherein the antibody comprises a VH as in any of the embodiments provided above, and a VL as in any of the embodiments provided above. In one embodiment, the antibody comprises the VH and VL sequences in SEQ ID NO: 33 and SEQ ID NO: 34, respectively, including post-translational modifications of those sequences. In one embodiment, the antibody comprises the VH and VL sequences in SEQ ID NO: 65 and SEQ ID NO: 10, respectively, including post-translational modifications of those sequences. In one embodiment, the antibody comprises the VH and VL sequences in SEQ ID NO: 66 and SEQ ID NO: 26, respectively, including post-translational modifications of those sequences.

In some embodiments, an anti-Jagged1 antibody comprises a heavy chain comprising the sequence of SEQ ID NO: 57, wherein X is any amino acid other than S, and a light chain comprising the sequence of SEQ ID NO: 53. In some embodiments, an anti-Jagged1 antibody comprises a heavy chain comprising the sequence of SEQ ID NO: 67, wherein X is any amino acid other than S, and a light chain comprising the sequence of SEQ ID NO: 75. In some embodiments, an anti-Jagged1 antibody comprises a heavy chain comprising the sequence of SEQ ID NO: 68, wherein X is any amino acid other than S, and a light chain comprising the sequence of SEQ ID NO: 76. In some embodiments, X is any amino acid other than S. In some embodiments, X is any amino acid other than S or H. In some embodiments, X is selected from A, D, E, G, I, K, L, N, Q, R T, and V. In some embodiments, X is T. In some embodiments, an anti-Jagged1 antibody comprises a heavy chain comprising the sequence of SEQ ID NO: 51, and a light chain comprising the sequence of SEQ ID NO: 53. In some embodiments, an anti-Jagged1 antibody comprises a heavy chain comprising the sequence of SEQ ID NO: 52, and a light chain comprising the sequence of SEQ ID NO: 53. In some embodiments, an anti-Jagged1 antibody comprises a heavy chain comprising the sequence of SEQ ID NO: 69, and a light chain comprising the sequence of SEQ ID NO: 75. In some embodiments, an anti-Jagged1 antibody comprises a heavy chain comprising the sequence of SEQ ID NO: 70, and a light chain comprising the sequence of SEQ ID NO: 76.

In a further aspect, the invention provides an antibody that binds to the same epitope as an anti-Jagged1 antibody provided herein. For example, in certain embodiments, an antibody is provided that binds to the same epitope as an anti-Jagged1 antibody comprising a VH sequence of SEQ ID NO: 33 and a VL sequence of SEQ ID NO: 34.

In a further aspect, the invention provides an antibody that competes for binding with any of the antibodies provided herein.

In a further aspect of the invention, an anti-Jagged1 antibody according to any of the above embodiments is a monoclonal antibody, including a chimeric, humanized or human antibody. In one embodiment, an anti-Jagged1 antibody is an antibody fragment, e.g., a Fv, Fab, Fab', scFv, diabody, or F(ab')$_2$ fragment. In another embodiment, the antibody is a full length antibody, e.g., an intact human IgG1 antibody or other antibody class or isotype as defined herein.

In a further aspect, an anti-Jagged1 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci.*

USA 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175

(Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Jagged1 and the other is for any other antigen. In certain embodiments, bispecific antibodies may bind to two different epitopes of Jagged1. Bispecific antibodies may also be used to localize cytotoxic agents to cells which express Jagged1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Jagged1 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). In some embodiments, an IgG1 constant region comprising an N297G or N297A mutation substantially lacks effector function. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6- fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Jagged1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Jagged1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Jagged1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-Jagged1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with antibody A, A-1, A-2, or A-1(S101T) for binding to human or murine Jagged1. In certain embodiments, such a competing antibody binds to the same epitope (e.g., a linear or a conformational epitope) that is bound by A, A-1, A-2, or A-1(S101T).

Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Jagged1 is incubated in a solution comprising a first labeled antibody that binds to Jagged1 (e.g., A, A-1, A-2, or A-1(S101T)) and a second unlabeled antibody that is being tested for its ability to compete with the first antibody for binding to Jagged1. The second antibody may be present in a hybridoma supernatant. As a control, immobilized Jagged1 is incubated in a solution comprising the first labeled antibody but not the second unlabeled antibody. After incubation under conditions permissive for binding of the first antibody to Jagged1, excess unbound antibody is removed, and the amount of label associated with immobilized Jagged1 is measured. If the amount of label associated with immobilized Jagged1 is substantially reduced in the test sample relative to the control sample, then that indicates that the second antibody is competing with the first antibody for binding to Jagged1. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-Jagged1 antibodies thereof having biological activity. Biological activity may include, e.g., inhibition of Jagged1-induced signaling through Notch1. In certain other embodiments, an antibody of the invention is tested for its ability to inhibit expression of a reporter gene that is responsive to Jagged1-induced Notch signaling. Nonlimiting exemplary assays are provided in the Examples. In certain embodiments, an antibody of the invention is tested for such biological activity. Antibodies having such biological activity in vivo and/or in vitro are also provided.

D. Immunoconjugates

The invention also provides immunoconjugates comprising an anti-Jagged antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, Phytolaca americana proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-Jagged1 antibodies provided herein is useful for detecting the presence of Jagged1 in a biological sample. The term "detecting" as used herein encompasses quantitative or qualitative detection. In certain embodiments, a biological sample comprises a cell or tissue, such as cancerous tissues.

In one embodiment, an anti-Jagged1 antibody for use in a method of diagnosis or detection is provided. In a further aspect, a method of detecting the presence of Jagged1 in a biological sample is provided. In certain embodiments, the method comprises contacting the biological sample with an anti-Jagged1 antibody as described herein under conditions permissive for binding of the anti-Jagged1 antibody to Jagged1, and detecting whether a complex is formed between the anti-Jagged1 antibody and Jagged1. Such method may be an in vitro or in vivo method. In one embodiment, an anti-Jagged1 antibody is used to select subjects eligible for therapy with an anti-Jagged1 antibody, e.g. where Jagged1 is a biomarker for selection of patients.

Exemplary disorders that may be diagnosed using an antibody of the invention include cancer, e.g., breast cancer, lung cancer, brain cancer, cervical cancer, colon cancer, liver cancer, bile duct cancer, pancreatic cancer, skin cancer, B-cell malignancies, and T-cell malignancies.

In certain embodiments, labeled anti-Jagged1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-Jagged1 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a cytotoxic agent, e.g., a chemotherapeutic agent. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-Jagged1 antibodies provided herein may be used in therapeutic methods.

In one aspect, an anti-Jagged1 antibody for use as a medicament is provided. In further aspects, an anti-Jagged1 antibody for use in treating a disease or disorder associated with aberrant Notch signaling, e.g. a cancer, is provided. In certain embodiments, an anti-Jagged1 antibody for use in a method of treatment is provided. In certain embodiments, the invention provides an anti-Jagged1 antibody for use in a method of treating an individual having a cancer comprising administering to the individual an effective amount of the anti-Jagged1 antibody. In one such embodiment, the method further comprises administering to the individual an effective amount of at least one additional therapeutic agent, e.g., as described below. In one such embodiment, the method further comprises administering to the individual an effective amount of at least one additional therapeutic agent, e.g., as described below.

In further embodiments, the invention provides an anti-Jagged1 antibody for use in inhibiting lung cancer growth. In certain embodiments, the invention provides an anti-Jagged1 antibody for use in a method of reducing lung cancer growth in an individual comprising administering to the individual an effective of the anti-Jagged1 antibody to reducing lung cancer growth. In certain embodiments, the invention provides an anti-Jagged1 antibody for use in a method of reducing breast cancer growth in an individual comprising administering to the individual an effective of the anti-Jagged1 antibody to reducing breast cancer growth. An "individual" according to any of the above embodiments is preferably a human.

In some embodiments, an anti-Jagged1 antibody is provided for treating allergy, asthma, autoimmune disease, diseases associated with goblet cell metaplasia (e.g., in lung) and/or excess mucus. Other allergic diseases that may be treated with the anti-Jagged1 antibodies provided herein include, but are not limited to, allergic rhinitis, atopic dermatitis, food hypersensitivity and urticaria; immune-mediated skin diseases include bullous skin diseases, erythema multiform and contact dermatitis; autoimmune disease include psoriasis, rheumatoid arthritis, juvenile chronic arthritis; inflammatory bowel disease (i.e., ulcerative colitis, Crohn's disease); idiopathic interstitial pneumonia, diseases associated with goblet cell metaplasia (such as asthma, COPD, cystic fibrosis and Barrett's esophagus), lung diseases such as cystic fibrosis, gluten-sensitive enteropathy, and Whipple's disease; immunologic diseases of the lung such as eosinophilic pneumonia, idiopathic pulmonary fibrosis and hypersensitivity pneumonitis; chronic obstructive pulmonary disease, RSV infection, uveitis, scleroderma, osteoporosis, and Hodgkin's lymphoma.

In a further aspect, the invention provides for the use of an anti-Jagged1 antibody in the manufacture or preparation of a medicament. In one embodiment, the medicament is for treatment of a disease or disorder associated with aberrant Notch signaling. In one embodiment, the medicament is for treatment of a cancer. In a further embodiment, the medicament is for use in a method of treating a cancer comprising administering to an individual having a cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a disease or disorder associated with aberrant Notch signaling. In one embodiment, the method comprises administering to an individual having such disease or disorder an effective amount of an anti-Jagged1 antibody. In one embodiment, the method comprises administering to an individual having a cancer an effective amount of an anti-Jagged1 antibody. In one such embodiment, the method further comprises administering to the individual an effective amount of at least one additional therapeutic agent, as described below. In one such embodiment, the method further comprises administering to the individual an effective amount of at least one additional therapeutic agent, as described below. An "individual" according to any of the above embodiments may be a human.

In a further aspect, the invention provides a method for inhibiting cancer cell growth in an individual. In one embodiment, the method comprises administering to the individual an effective amount of an anti-Jagged1 antibody to inhibit cancer cell growth. In one embodiment, an "individual" is a human.

In some embodiments, the invention provides methods for treating allergy, asthma, autoimmune disease, diseases associated with goblet cell metaplasia (e.g., in lung) and/or excess mucus in an individual. In some embodiments, the invention provides methods for treating allergic rhinitis, atopic dermatitis, food hypersensitivity and urticaria; immune-mediated skin diseases include bullous skin diseases, erythema multiform and contact dermatitis; autoimmune disease include psoriasis, rheumatoid arthritis, juvenile chronic arthritis; inflammatory bowel disease (i.e., ulcerative colitis, Crohn's disease); idiopathic interstitial pneumonia, diseases associated with goblet cell metaplasia (such as asthma, COPD, cystic fibrosis and Barrett's esophagus), lung diseases such as cystic fibrosis, gluten-sensitive enteropathy, and Whipple's disease; immunologic diseases of the lung such as eosinophilic pneumonia, idiopathic pulmonary fibrosis and hypersensitivity pneumonitis; chronic obstructive pulmonary disease, RSV infection, uveitis, scleroderma, osteoporosis, and/or Hodgkin's lymphoma in an individual. In some embodiments, the method comprises administering to the individual an effective amount of an anti-Jagged1 antibody provided herein. In some embodiments, an "individual" is a human.

In a further aspect, the invention provides pharmaceutical formulations comprising any of the anti-Jagged1 antibodies provided herein, e.g., for use in any of the above therapeutic methods. In one embodiment, a pharmaceutical formulation comprises any of the anti-Jagged1 antibodies provided herein and a pharmaceutically acceptable carrier. In another embodiment, a pharmaceutical formulation comprises any of the anti-Jagged1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a cytotoxic agent. In certain embodiments, an additional therapeutic agent is an antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-Jagged1 antibody and administration of an additional therapeutic agent occur within about one month, or within about one, two or three weeks, or within about one, two, three, four, five, or six days, of each other. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-Jagged1 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Jagged1 antibody.

III. Examples

The following are examples of methods and compositions of the invention. It is understood that various other embodiments may be practiced, given the general description provided above.

Example 1

Generation of Anti-Jagged Antibodies a. Library Sorting and Screening to Identify Anti-Jagged1 Antibodies Human phage antibody libraries with synthetic diversities in the selected complementarity determining regions, mimicking the natural diversity of human IgG repertoire, were used for panning Fab fragments displayed on the surface of M13 bacteriophage particles. Human Jag1-DSL-EGF1-4 (SEQ ID NO:6) or human Jag2-DSL-EGF1-4 (SEQ ID NO:8) was used as antigen for library sorting. Nunc 96 well Maxisorp immunoplates were coated overnight at 4° C. with target antigen (10 m/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., J. Immunol. Meth. 284:119-132 (2004)) and VH/VL (see Liang et al., JMB. 366: 815-829 (2007)) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phages were amplified in *E. coli* XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to human Jagged1 or Jagged2. The variable regions of these clones were PCR sequenced to identify unique sequence clones. The affinities of phage antibodies were ranked using spot competition ELISA. The phage antibody IC50 values were further determined using competitive phage-binding ELISA. Unique phage antibodies that bind specifically to human Jagged1 (and not Jagged2), Jagged2 (and not Jagged1), or to both Jagged1 and Jagged2 were chosen and reformatted to full-length IgGs for evaluation in in vitro cell assays.

Clones of interest were reformatted into IgGs by cloning $V_L$ and $V_H$ regions of individual clones into a pRK mammalian cell expression vector (pRK.LPG3.HumanKappa) containing the human kappa constant domain, and expression vector (pRK.LPG4.HumanHC) encoding the full-length human IgG1 constant domain, respectively (Shields et al., *J Biol Chem* 2000; 276: 6591-6604). The antibodies were then transiently expressed in mammalian CHO cells, and purified with a protein A column.

b. Construction of Libraries for Affinity Improvement of Clones Derived from the $V_H$ or $V_H V_L$ Libraries Phagemid pW0703, derived from phagemid pV0350-2b (Lee et al., *J. Mol. Biol* 340, 1073-1093 (2004), containing stop codon (TAA) in all CDR-L3 positions and displaying monovalent Fab on the surface of M13 bacteriophage) served as the library templates for grafting heavy chain variable domains ($V_H$) of clones of interest from the $V_H$ library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol* 340, 1073-1093 (2004)). To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *Journal of Medicinal Chemistry* 37:1233-1251 (1994)). For soft randomization, residues at positions 91-96 of CDR-L3, 30-33, 35 of CDR-H1, 50, 52, 53-54, and 56 of CDR-H2, 95-98 of CDR-H3 were targeted; and three different combinations of CDR loops, H1/L3, H2/L3, and H3/L3, were selected for randomization.

For clones originated from $V_H V_L$ library, phagemids containing 4 stop codons (TAA) in each CDR and displaying monovalent Fab on the surface of M13 bacteriophage were generated individually, and served as the templates for kunkel mutagenesis for the construction of affinity maturation libraries. Only soft randomization strategy was used for clones derived from $V_H V_L$ library, as diversity of CDR-L3 was built into the naïve library. To achieve the soft randomization conditions, residues at positions 28-31 of CDR-L1, 50, 53-55 of CDR-L2, 91-96 of CDR-L3, 30-35 of CDR-H1, 50-56 of CDR-H2, 95-100 of CDR-H3 were targeted; and four different combinations of CDR loops, H1/L3*, H2/L3*, and H3/L3* and L1/L2/L3* (where * denotes the position of stop codons on the template), were selected for randomization.

c. Phage Sorting Strategy to Generate Affinity Improvement

For affinity improvement selection, Jag1 or Jag2 antigens were first biotinylated under limiting reagent condition. Phage libraries were subjected to one round of plate sorting and five rounds of solution sorting with increasing stringency. For the first round of plate sorting, 10 ug/ml antigen was first coated on Maxisorp plate and preblocked with blocking buffer (1% BSA and 0.05% Tween20 in PBS). 3 O.D./ml in blocking buffer of phage input were incubated to antigen plates for 3 hours. The wells were washed with PBS-0.05% Tween20 ten times. Bound phage was eluted with 150 μl/well 50 mM HCl, 500 mM KCl for 30 minutes, and subsequently neutralized by 50 μl/well of 1M Tris pH8, titered, and propagated for the next round. For subsequent rounds, panning of the phage libraries was done in solution phase, where phage library was incubated with 100 nM biotinylated target protein (the concentration is based on parental clone phage IC50 value) in 100 μl buffer containing 1% Superblock (Pierce Biotechnology) and 0.05% Tween20 for 2 hours at room temperature. The mixture was further diluted 10× with 1% Superblock, and 100 μl/well was applied to neutravidin-coated wells (10 μg/ml) for 30 minutes at room temperature with gentle shaking To determine background binding, control wells containing phage were captured on neutravidin-coated plates. Bound phage was then washed, eluted and propagated as described for first round. Five more rounds of solution sorting were carried out together with increasing selection stringency. The first couple rounds of which is for on-rate selection by decreasing biotinylated target protein concentration from 100 nM to 0.1 nM, and the last two rounds of which is for off-rate selection by adding excess amounts of non-biotinylated target protein (300 to 1000 fold more) to compete off weaker binders at room temperature.

d. High Throughput Affinity Screening ELISA (Single Spot Competition)

Colonies were picked from the sixth round of screening. Colonies were grown overnight at 37° C. in 150 μl/well of 2YT media with 50 μg/ml carbenicillin and $1 \times 10^{10}$/ml M13KO7 in 96-well plate (Falcon). From the same plate, a colony of XL-1 infected parental phage was picked as control. 96-well Nunc Maxisorp plates were coated with 100 μl/well of either Jag1 or Jag2 (0.5 m/ml) in PBS at 4° C. overnight. The plates were blocked with 150 μl of 1% BSA and 0.05% Tween20 in PBS 20 for 1 hour.

35 μl of the phage supernatant was diluted with to 75 μl of in ELISA (enzyme linked immunosorbent assay) buffer (PBS with 0.5% BSA, 0.05% Tween20) with or without 5 nM Jag1 or Jag2 and let incubate for 1 hour at room temperature in an F plate (NUNC). 95 μl of mixture was transferred side by side to the antigen coated plates. The plate was gently shaken for 15 min and was washed ten times with PBS-0.05% Tween 20. The binding was quantified by adding horseradish peroxidase (HRP)-conjugated anti-M13 antibody in ELISA buffer (1:2500) and incubated for 30 minutes at room temperature. The plates were washed with PBS-0.05% Tween 20 ten times. Next, 100 μl/well of Peroxidase substrate was added to the well and incubated for 5 minutes at room temperature. The reaction was stopped by adding 100 μl 0.1M Phosphoric Acid ($H_3PO_4$) to each well and allowed to incubate for 5 minutes at room temperature. The O.D. (optical density) of the yellow color in each well was determined using a standard ELISA plate reader at 450 nm. In comparison to the $OD_{450nm}$ reduction (%) of the well of parental phage (100%), clones that had the $OD_{450nm}$ reduction (%) lower than 50% were picked for sequence analysis. Unique clones were selected for phage preparation to determine binding affinity (phage IC50) against either Jag1 or Jag2 by comparison to respective parental clones. Then the most affinity-improved clones were reformatted into human IgG1 for antibody production and further BIAcore binding kinetic analysis and other in vitro or in vivo assay.

Further screening rounds identified antibodies specific for only one of the Jagged family members, as determined by ELISA. Antibody A bound human and murine Jagged1, but not Jagged2 (FIG. 8; heavy chain variable region sequence shown in SEQ ID NO: 9, light chain variable region sequence shown in SEQ ID NO: 10). Conversely, antibody B (the parental antibody of antibody B-3) bound human and murine Jagged2, but not Jagged1 (FIG. 8). C-1 binds to both Jagged1 and Jagged2, and served as a control. The heavy chain and light chain variable region sequences for antibody C-1 are shown in FIG. 4.

Example 2

Antibody Binding Affinities and Epitope Mapping

Binding affinities of anti-Jagged1 phage antibodies were measured by Surface Plasmon Resonance (SRP) using a BIAcore™-3000 instrument. Anti-Jagged1/2 phage human IgGs were captured by mouse anti-human IgG coated on the CM5 sensor chip to achieve approximately 150 response units (RU). For kinetics measurements, two-fold serial dilutions of human or mouse Jag1/2 DSL EGF1-4 (1.95 nM to 250 nM) were injected in PBT buffer (PBS with 0.05% Tween 20) at 25° C. with a flow rate of 30 ml/min. Association rates ($k_{on}$) and dissociation rates ($k_{off}$) were calculated using a simple one-to-one Langmuir binding model (BIAcore Evaluation Software version 3.2). The equilibrium dissociation constant ($k_d$) was calculated as the ratio $k_{off}/k_{on}$.

Table 2 summarizes the binding constants for antibodies A, A-1, A-2, B, and B-3 binding to purified human Jagged1, human Jagged2, and mouse Jagged2. Parent antibody A specifically bound to human and murine Jagged1. The affinity matured antibodies A-1 and A-2 bound both human and murine Jagged1 with high affinity. Antibodies A, A-1 and A-2 did not bind human or murine Jagged2. Conversely, antibodies B and B-3 did not bind human or murine Jagged1. B-3 specifically bound to human and mouse Jagged2.

TABLE 2

Biacore summary table

| Ab | Human Jag1 | | | Human Jag2 | | | Mouse Jag2 | | |
|---|---|---|---|---|---|---|---|---|---|
|  | kon (1/Ms) | koff (1/s) | Kd (M) | kon (1/Ms) | koff (1/s) | Kd (M) | kon (1/Ms) | koff (1/s) | Kd (M) |
| A | 2.3E+04 | 2.1E−03 | 9.4E−08 | No binding up to 0.5 µM | | | | | |
| A-1 | 8.3E+04 | 5.9E−05 | 7.1E−10 | | | | | | |
| A-2 | 2.3E+05 | 7.1E−05 | 3.0E−10 | | | | | | |
| B | No binding up to 0.5 µM | | | 2.5E+06 | 2.6E−03 | 1.0E−09 | 2.5E+06 | 2.6E−03 | 1.0E−09 |
| B-3 | | | | | | | 5.8E+05 | 1.75E−04 | 3.0E−10 |

The heavy chain and light chain variable region sequences for antibody A are shown in SEQ ID NOs: 9 and 10, respectively. The heavy chain and light chain variable region sequences for antibody A-1 are shown in SEQ ID NOs: 17 and 18, respectively. The heavy chain and light chain variable region sequences for antibody A-2 are shown in SEQ ID NOs: 25 and 26, respectively. The heavy chain and light chain variable region sequences for antibody B-3 are shown in SEQ ID NOs: 41 and 42, respectively. The heavy chain and light chain variable region sequences for antibody B are shown in FIG. 4.

Example 3

Anti-Jagged Antagonist Antibodies Inhibit Jagged1-Induced Signaling In Vitro To determine whether anti-Jagged antibodies can act as antagonists of Jagged-induced Notch signaling, co-culture experiments were performed essentially as described by Wu et al., *Nature* 464, 1052-1057 (15 Apr. 2010). NIH-3T3 cells engineered to express Jagged1, as the Notch ligand, were co-cultured with NIH 3T3 cells that stably express Notch1 and that were transiently transfected to express a Notch-responsive TP-1 (12×CSL) firefly luciferase reporter and a constitutively expressed Renilla luciferase reporter (pRL-CMV, Promega). Strong Notch reporter signal (Firefly luciferase) was observed in the co-culture (FIG. 12, J1 induced-Positive Control). Reporter expression was reduced to background levels when a γ-secretase inhibitor was added to the co-culture, demonstrating Notch-dependent expression of the reporter construct. Data not shown.

Figure 9A:
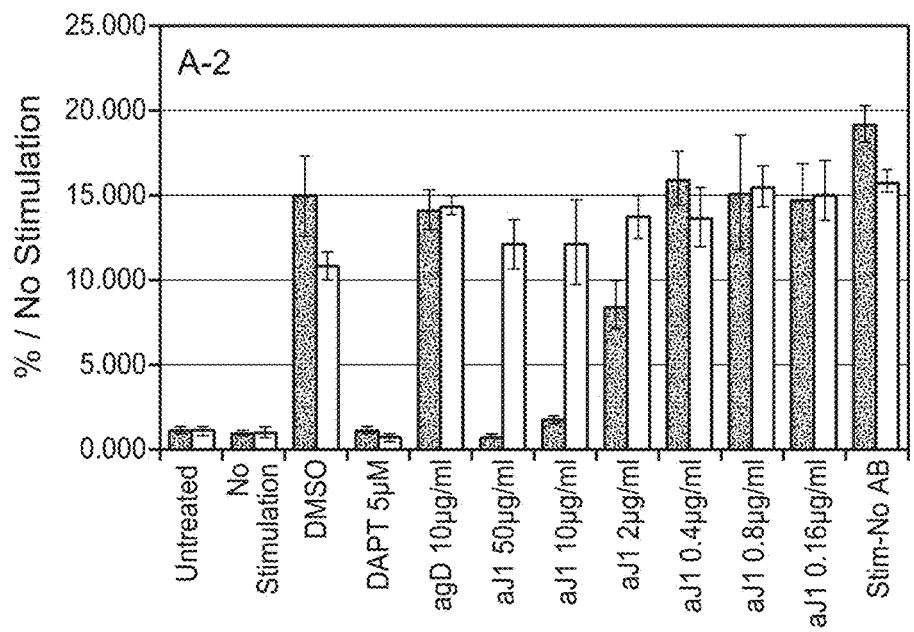
FIGS. 9A-B show inhibition of Notch signaling by affinity matured anti-Jagged antibodies. Co-culture assays were performed as described in Example 3. Phage antibodies at the indicated concentration are indicated on the x-axis. DAPT at the indicated concentrations served as positive control for inhibition of Notch signaling; DMSO served as vehicle control. Signaling was induced by Jagged1 (dark gray columns) or by Jagged2 (light gray columns). Untreated=cultures that were not stimulated with ligand and not treated with antibody; No Stimulation=cultures not stimulated with ligand; agD=isotype control antibody; Stim/no AB=cultures stimulated with ligand but not treated with antibody; gamma-secretase inhibitor DAPT or the DAPT vehicle control of DMSO.
Figure 9B:
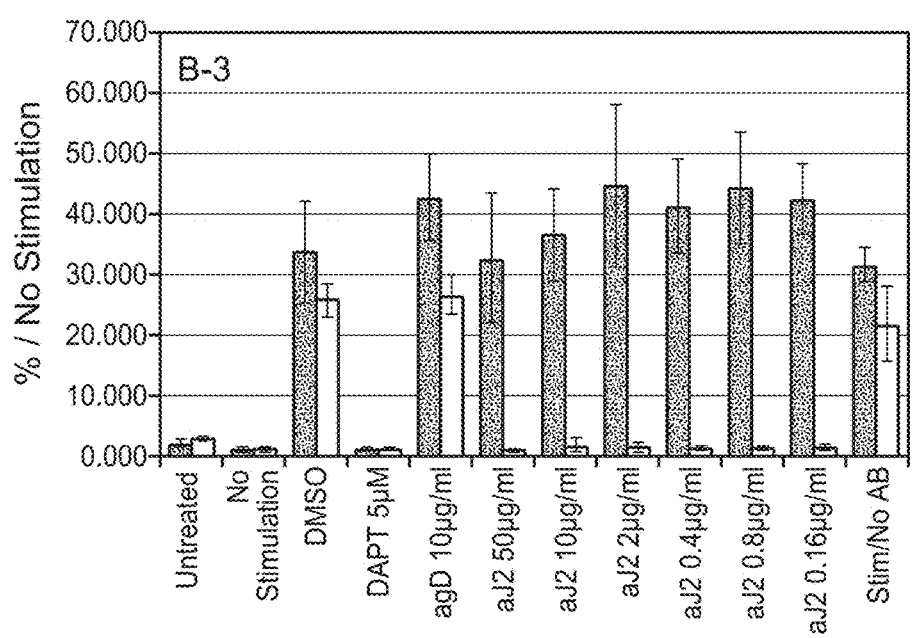

Addition of increasing amounts (0.016-50 µg/ml) of anti-Jagged antibody A-2 (heavy chain and light chain variable region sequences of SEQ ID NOs: 25 and 26, respectively) or B-3 (heavy chain and light chain variable region sequences of SEQ ID NOs: 41 and 42, respectively) resulted in dose-dependent inhibition of reporter expression (FIG. 9). Signaling was induced by Jagged1 (FIG. 9A, dark gray columns) or by Jagged2 (FIG. 9B, light gray columns) and inhibition was determined as described above. Controls included cultures that were not stimulated with ligand and not treated with antibody (FIGS. 9A and B, Untreated), not stimulated with ligand (FIGS. 9A and B, No Stimulation), treated with 5-10 µg/ml isotype control antibody (FIGS. 9A and B, agD), stimulated with ligand but not treated with antibody (FIGS. 9A and B, Stim/no AB), treated with 5 µM of the gamma-secretase inhibitor DAPT or the DAPT vehicle control of DMSO.

Antibody A-2 inhibited Jagged1-induced signaling, but not Jagged2-induced signaling, in a dose-dependent manner (FIG. 9A). The $IC_{50}$ for A-2 was between 2 and 10 µg/ml for Jagged1 inhibition whereas little or no Jagged2 inhibition was observed even at the highest concentration of 50 µg/ml. The results demonstrate that antibody A-2 is a Jagged1-selective antagonist, i.e., antibody A-2 inhibits Jagged1-mediated signaling, but not Jagged2-mediated signaling. In contrast, antibody B-3 potently inhibited Jagged2-induced signaling at the lowest concentration tested but did not inhibit Jagged1-induced signaling at the highest concentration tested, thus establishing B-3 as a Jagged1-selective antagonist (FIG. 9B).

Example 4

Effect of Anti-Jagged Antibody Treatment on Body Weight

Figure 10A:
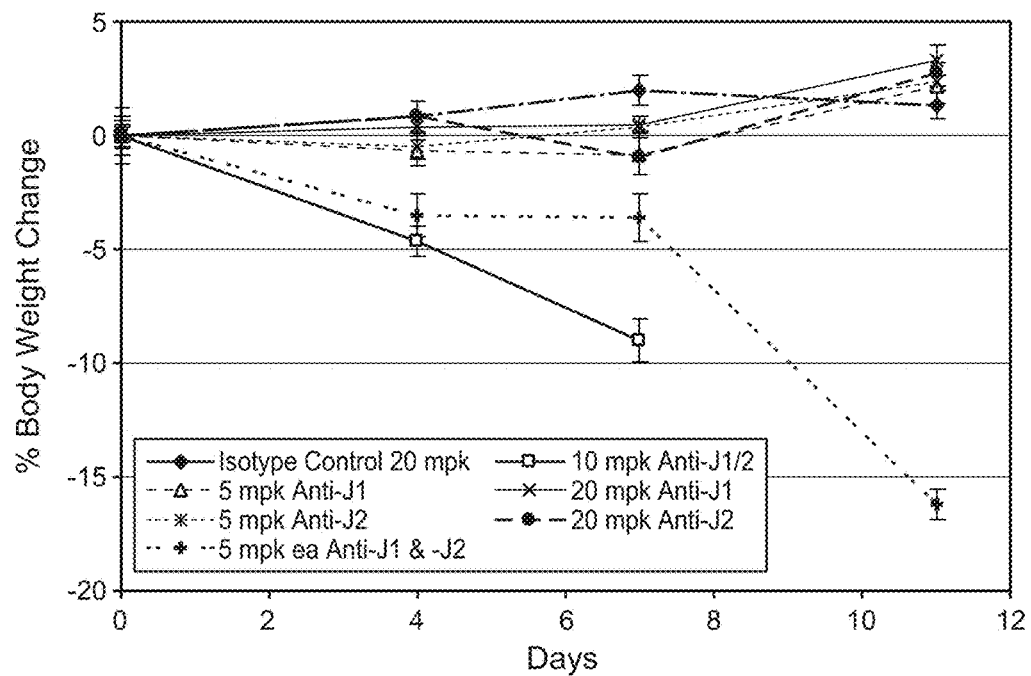
FIGS. 10A-B show that combined inhibition of Jagged1 and Jagged2 causes rapid weight loss. (A) Mice were dosed twice per week with the anti-Jagged1/2 antibody C-1 (anti-J1/2; 5-10 mpk), the anti-Jagged1 antibody A-2 (anti-J1; 5-20 mpk), the anti-Jagged2 antibody B-3 (anti-J2; 5-20 mpk), the antibody A-2 and B-3 together (anti-J1 & -2; 5 mpk each) or an isotype control antibody (20 mpk). Total antibody concentration of each dosing was brought up to 20 mpk with the isotype control antibody, where necessary. The average body weight changes (y-axis) are graphed as a percentage of starting body weight over time (x-axis). (B) Balb/c mice (ten per group, individually housed) were injected IP twice per week with either 30 mpk of anti-gD isotype control antibody or with a combination of 15 mpk antibody A-2 plus 15 mpk antibody B-3 for eight days. Food intake was assessed by daily weighing of the food delivered and remaining in each cage. Error bars represent standard deviations (n=10).
Figure 10B:
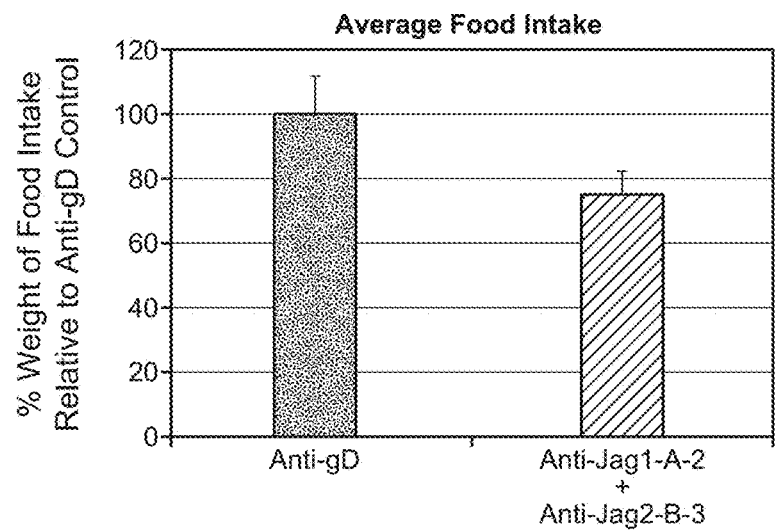

As described above, gamma-secretase inhibitors, and other inhibitors of multiple Notch receptors, cause weight loss and intestinal goblet cell metaplasia, which is undesirable for clinical administration. To determine how the antibodies described herein affect body weight and intestinal health, mice were dosed twice per week with the anti-Jagged1 antibody A-2 (5-20 mpk; heavy chain and light chain variable region sequences of SEQ ID NOs: 25 and 26, respectively), the anti-Jagged2 antibody B-3 (5-20 mpk;

heavy chain and light chain variable region sequences of SEQ ID NOs: 41 and 42, respectively), the antibody A-2 and B-3 together (5 mpk each), an anti-Jagged1/2 antibody that binds to both Jagged 1 and Jagged 2 (C-1; 5-10 mg antibody per kg mouse body weight (mpk); heavy and light chain variable regions sequence shown in FIG. 4), or the isotype control anti-gD antibody (20 mpk). The isotype control antibody was also used to bring the total antibody concentration of each dosing to 20 mpk. Total body weight of each mouse was determined prior to first administration of antibodies and monitored until day 12 of the study. The average body weight changes are depicted in FIG. 10, graphed as a percentage of starting body weight. Dual inhibition of Jagged1 and Jagged2, using either the anti-Jagged1/2 antibody C-1 or a combination of the Jagged1-specific antibody A-2 and the Jagged2-specific antibody B-3 together, caused rapid and substantial weight loss (FIG. 10A). By day 4, some mice that received the anti-Jagged1/2 antibody C-1 had lost over 5% of their bodyweight, which progressed to nearly 8-10% loss in body weight by day 7 (FIG. 10A). Mice that received both A-2 and B-3 also lost weight rapidly, in some cases up to 17% by day 11 (FIG. 10A). In contrast, none of the Jagged1-specific or Jagged2-specific antibodies alone caused weight loss over the course of the study at either 5 or 20 mpk (FIG. 10A). Treatment with the combination of anti-Jagged1 plus anti-Jagged2 antibodies resulted in decreased food intake (FIG. 10B), which correlated with the observed decrease in body weight (FIG. 10A) and suggested that decreased food intake could partly or entirely account for the correlated body weight decreases.

Example 5

Anti-Jagged1 Antagonist Antibodies Inhibit Human Lung Cancer Cell Growth In Vivo Harlan athymic nude mice were inoculated subcutaneously with Calu-6 cells, a human non-small cell lung cancer line. After tumor volume reached approximately 200 cubic mm, mice were injected intraperitoneally (IP) twice per week (days 0, 4, 7, 11, 14 and 18) with 20 mpk of either anti-gD isotype control antibody (n=10) or with anti-Jagged1 antibody A-2 (n=10; heavy chain and light chain variable region sequences of SEQ ID NOs: 25 and 26, respectively). Tumor volume in each mouse was measured with calipers for another 19 days. Total body weight of each mouse was monitored over the course of the study.

Figures 1, 11B:
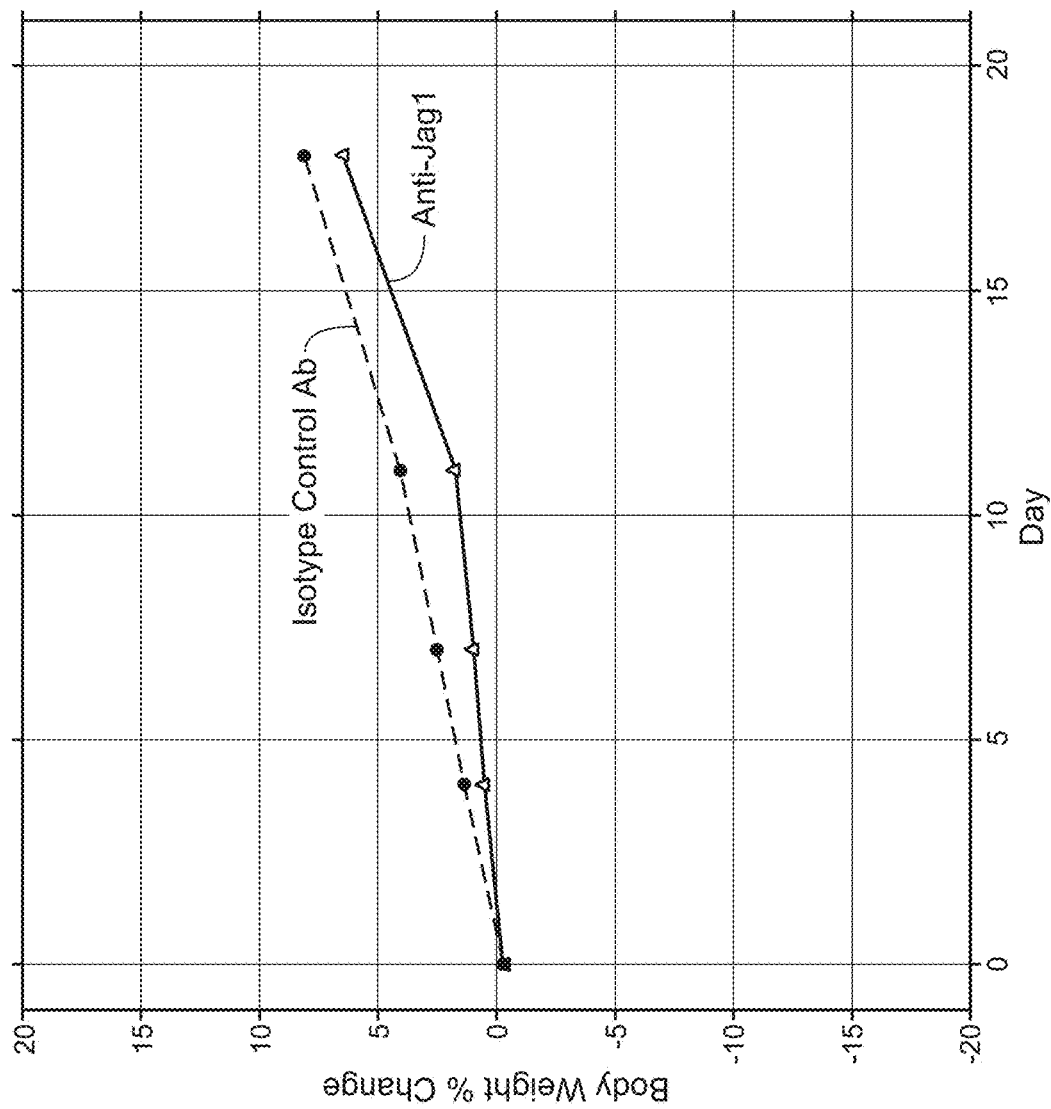
Figures 2, 11B:
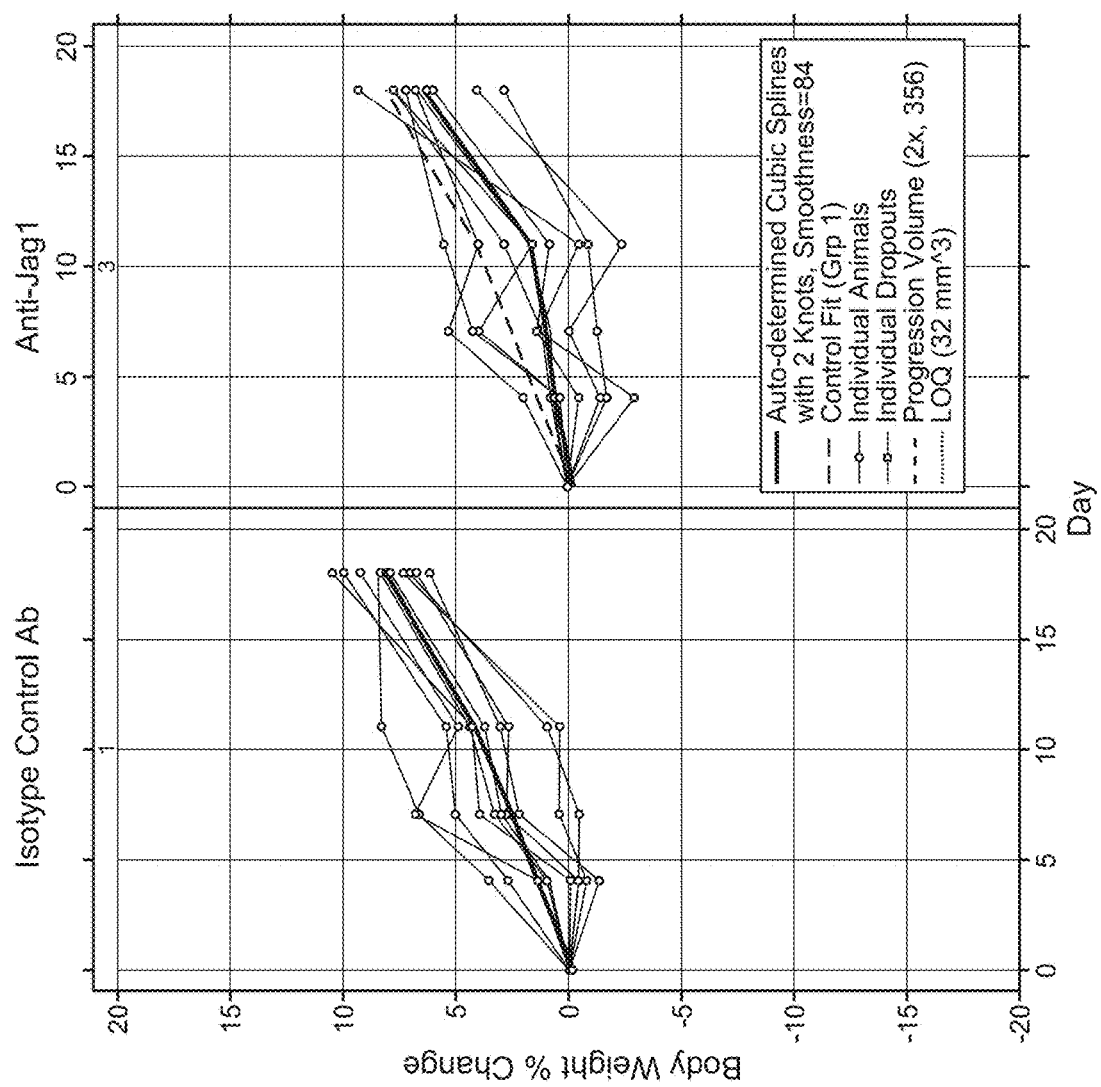

Tumors in mice treated with anti-Jagged1 showed a significant decrease in tumor volume relative to tumors in the control group (FIG. 11A). The effect of the anti-Jagged1 antibody treatment could be detected as early as day seven after treatment (FIG. 11A). At day 18, the average tumor volume in mice that received the anti-Jagged1 antibody reached approximately 500 mm$^3$, while average tumor volume in control animals reached approximately 750 mm$^3$ at day 18. No significant change in body weight between the treatment and control group could be observed (FIG. 11B).

Example 6

Figure 12A:
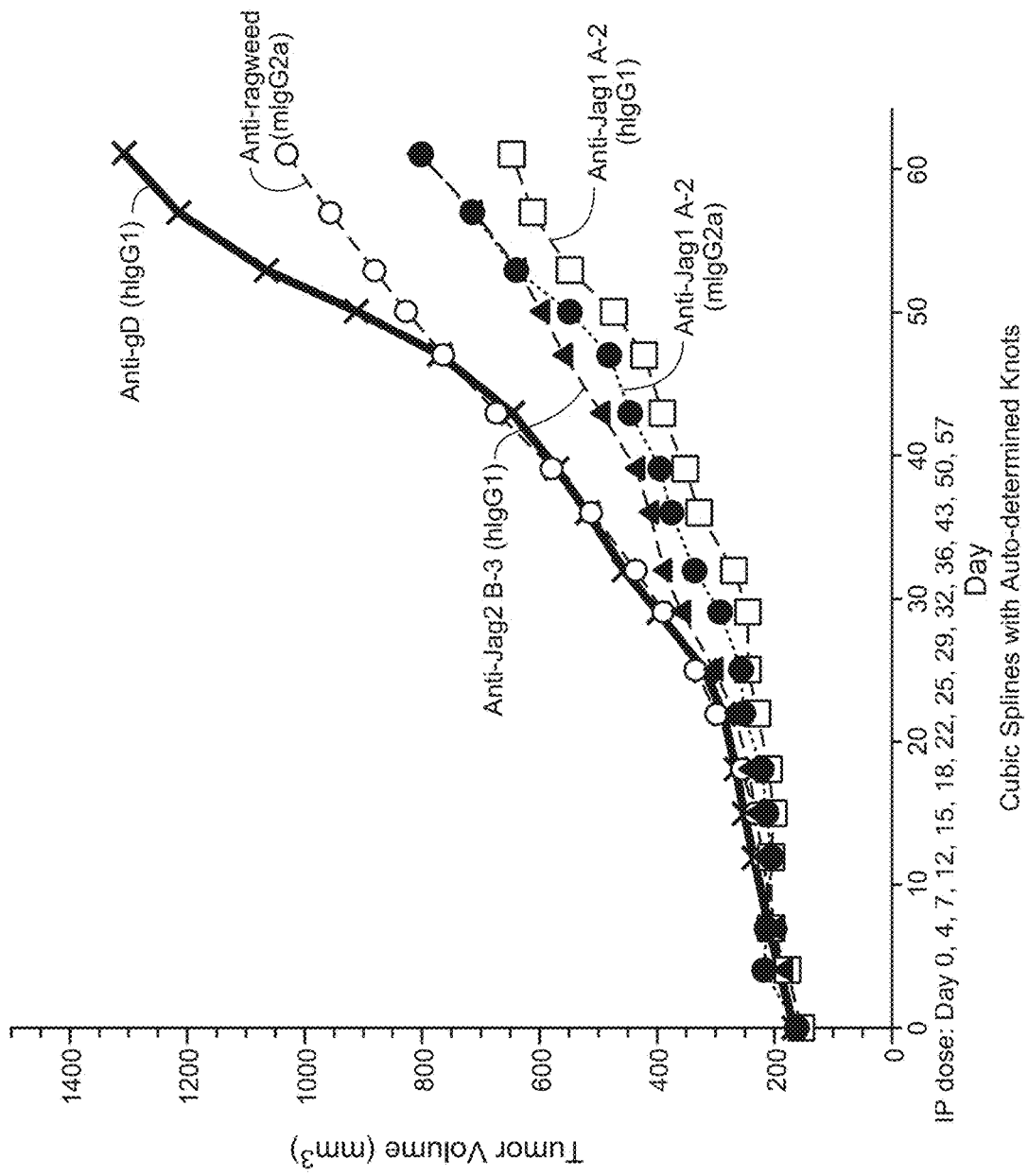
FIGS. 12A-B show inhibition of human breast cancer cell growth by anti-Jagged1 and anti-Jagged2 antagonist antibodies in vivo. C.B-17 SCID.bg mice with human breast cancer xenografts were injected on days 0, 4, 7, 12, 15, 18, 22, 25, 29, 32, 36, 43, 50, and 57 with anti-gD isotype control antibody (Anti-gD), anti-ragweed isotype control antibody (anti-ragweed), anti-Jagged1 antibody A-2 in the human IgG1 backbone (anti-Jag1 A-2 (hIgG1)), anti-Jagged1 antibody A-2 in the murine IgG2a backbone (anti-Jag1 A-2 (mIgG2a)), or anti-Jagged2 antibody B-3 in the human IgG1 backbone (anti-Jag2 B-3 (hIgG1)). Tumor volumes (y-axis) of treatment groups (A) or individual animals (B) were plotted using a linear mixed effects model over time (x-axis).
Figure 12B:
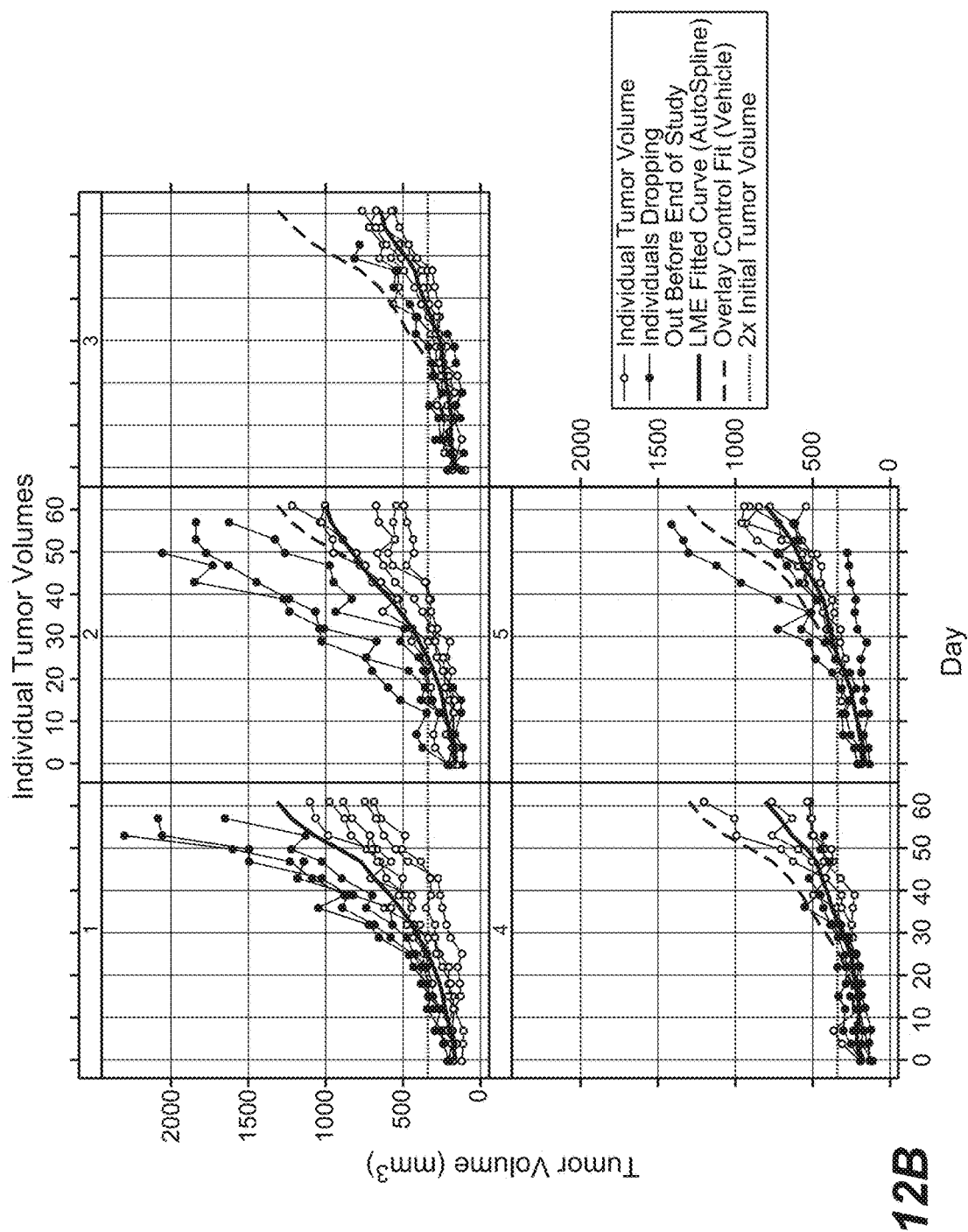

Anti-Jagged1 and Anti-Jagged2 Antibodies Inhibit Human Breast Cancer Cell Growth In Vivo C.B-17 SCID.bg mice were inoculated in the mammary fat pad with MDA-MD-468 cells, a human basal breast cancer line. After tumor volume reached approximately 200 cubic mm, mice were dosed IP with 30 mpk of either anti-gD isotype control antibody (human IgG1 isotype), anti-ragweed isotype control antibody (murine IgG2a isotype), anti-Jagged1 antibody A-2 (heavy chain and light chain variable region sequences of SEQ ID NOs: 25 and 26, respectively) in the human IgG1 backbone, anti-Jagged1 antibody A-2 in the murine IgG2a backbone or anti-Jagged2 antibody B-3 (heavy chain and light chain variable region sequences of SEQ ID NOs: 41 and 42, respectively) in the human IgG1 backbone on days 0, 4, 7, 12, 15, 18, 22, 25, 29, 32, 36, 43, 50, and 57. Tumor volume (y-axis) was measured with calipers for 60 days after the first injection. The tumor volumes for each group (n=9 per group) were plotted using a linear mixed effects model (FIG. 12A). Tumor volumes for each mouse in each group are depicted in FIG. 12B.

Example 7

Anti-Jagged1 Antibodies are Cleaved in the Heavy Chain

Antibodies A (heavy chain and light chain variable region sequences of SEQ ID NOs: 9 and 10, respectively), A-1 (heavy chain and light chain variable region sequences of SEQ ID NOs: 17 and 18, respectively), and A-2 (heavy chain and light chain variable region sequences of SEQ ID NOs: 25 and 26, respectively) were analyzed by SDS-PAGE and mass spectrometry for integrity of the heavy and light chains. For SDS-PAGE analysis, each antibody sample was mixed in a 1:1 v/v ratio with 2× Tris-Glycine SDS Sample Buffer (Novex LC2676), in the absence and presence of 10 mM DTT. Samples were heated at 95° C. for 5 minutes, and 2 µg of each sample was loaded onto a Novex 4-20% SDS-PAGE, 1.0 mm gel (Novex EC6025). 10 µL of Mark 12 molecular weight standard (Invitrogen 100006637) was also loaded onto the gel. Electrophoresis was run in 1× Tris-Glycine SDS Running Buffer (Invitrogen LC2675-5) at a constant 250V until the tracking dye reached the bottom of the gel. The gel was then stained with a Coommassie-based stain (Expedeon InstantBlue #ISB1L).

For mass spectrometry analysis, each antibody was diluted to a final concentration of 1 mg/mL in PBS. The pH of the antibody was increased to 8.0 with addition of 1:10 v/v of 1.0M Tris, pH 8.0. DTT to a final concentration of 10 mM in solution was added to reduce the antibody. The sample was then heated at 37° C. for 15 minutes. Samples were then injected onto a PLRP-S 1000 Å, 8 µm, 2.1×50 mm column (Agilent, PL1912-1802) heated to 80° C. using an Agilent 1200 HPLC system, followed by electrospray ionization on an Agilent 6210 TOF LC/MS system.

Figure 13A:
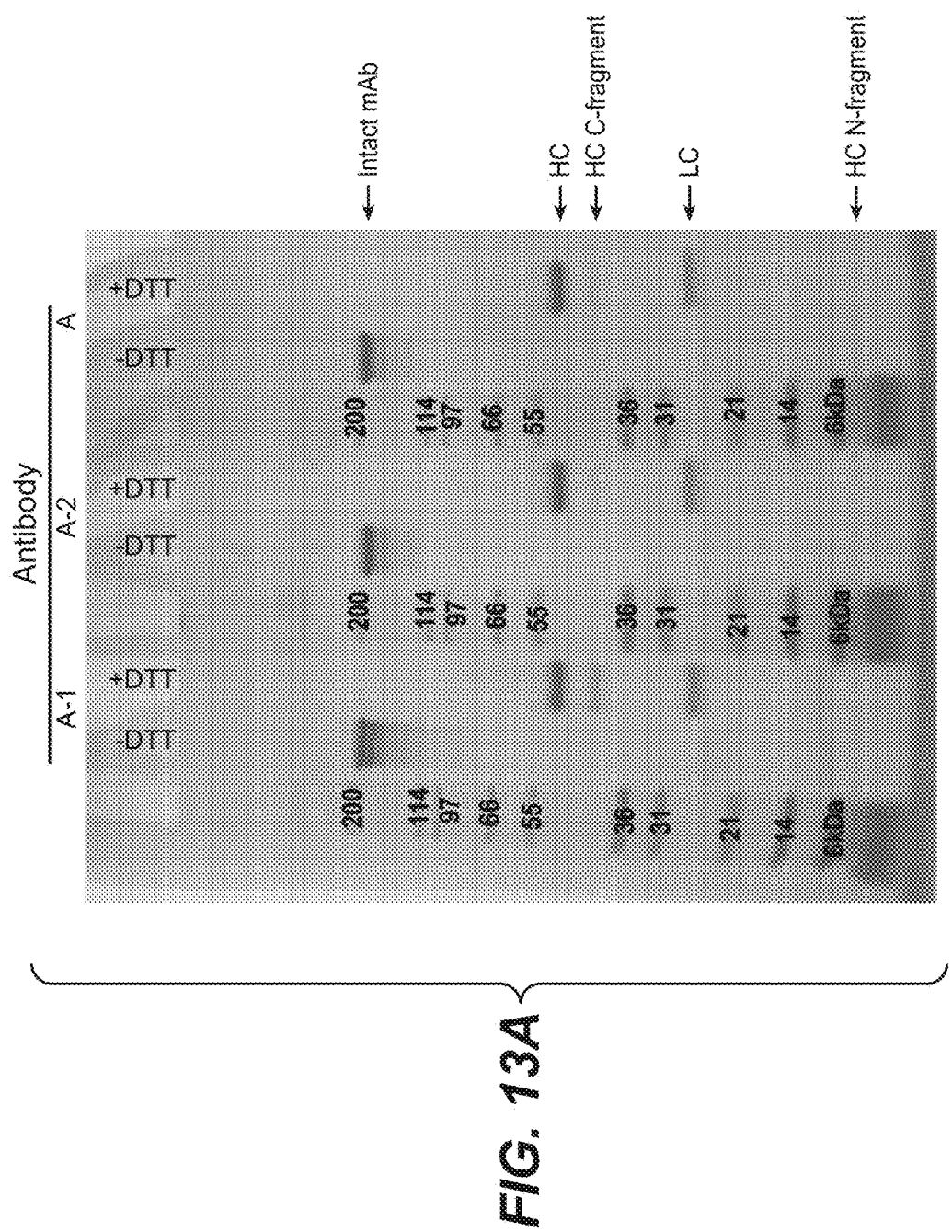
Figure 13B:
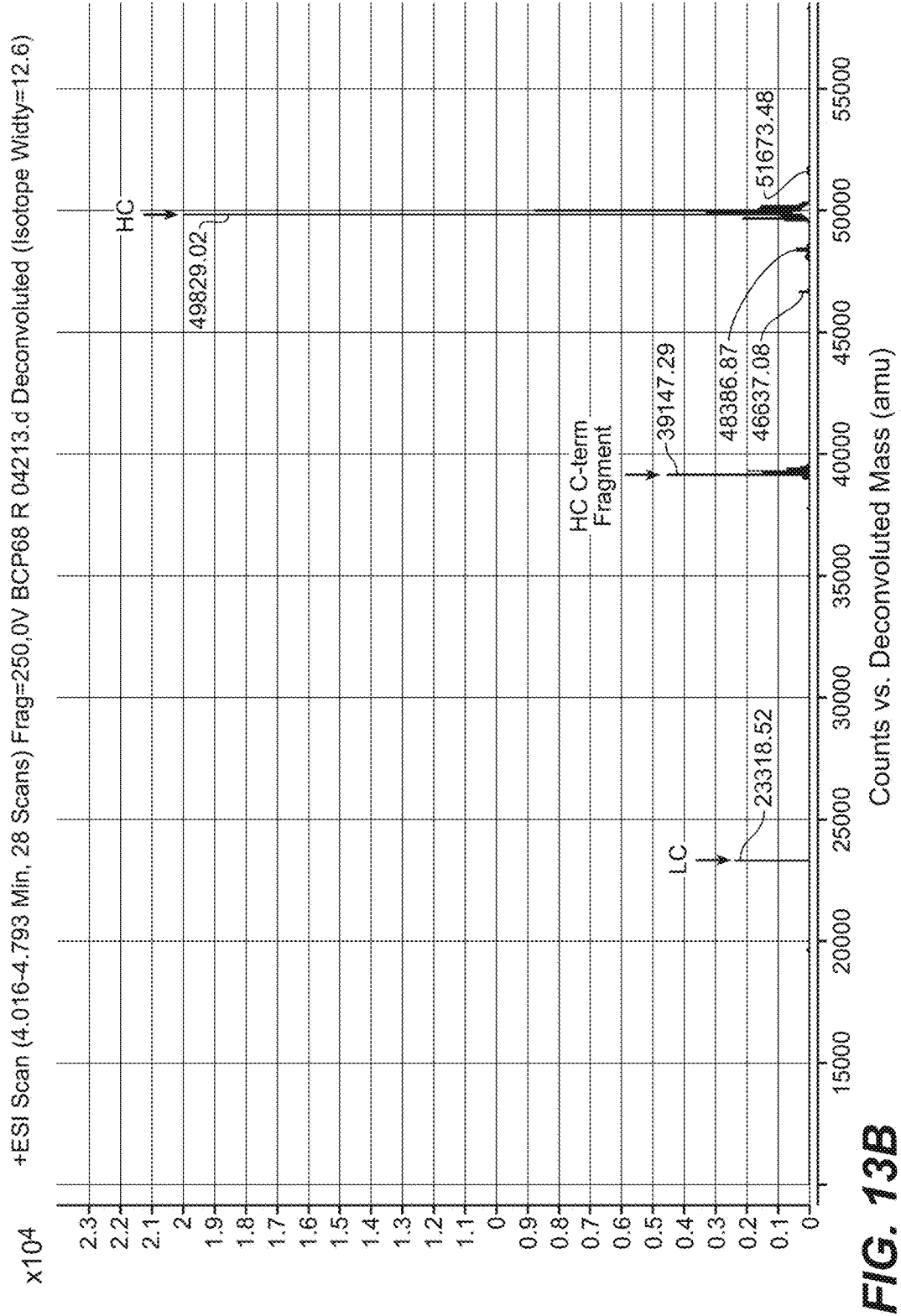

The results of those analyses are shown in FIG. 13. The SDS-PAGE analysis (FIG. 13A) revealed that a fraction of the heavy chain (HC) is cleaved in each of the antibodies. The bands corresponding to the intact HC and light chain (LC), as well as the carboxy (C)-terminal and amino (N)-terminal cleaved fragments of the HC, are marked to the right of the gel. A representative mass spectrometry analysis, for antibody A-1, is shown in FIG. 13B. This analysis indicated that the cleavage site was between HC amino acids G100 and S101 (sequential numbering, corresponding to G96 and S97 according to Kabat numbering) in CDR3, as diagramed in the HC amino acid sequence in FIG. 13C, with the arrow marking the cleavage position. Similar analyses revealed that the HC cleavage occurred in all tested preparations of these antibodies (including following expression in two different cell types, CHO and 293) and that cleavage occurred independent of the type of antibody Fc region (human IgG1 or murine IgG2a).

An SDS-PAGE gel of the anti-Jagged1 antibodies was run substantially as described above. Rather than staining with Coommassie-based stain, antibody was transferred onto PVDF membrane (Invitrogen LC2002) using XCell Blot Module (Invitrogen EI9051) at constant 0.35 A. The membrane was stained with Coomassie Blue R-250. The samples on membrane were subjected to N-terminal sequence analysis using the Applied Biosystems Procise Sequencer 494 according to the sequencing principle described in Niall, 1973, Meth. Enzymol. 27: 942-1010.

The results of the sequencing analysis are shown in FIG. 14. This method confirmed that the cleavage site was the same one predicted from the mass spectrometry results, which is between G100 and S101 (sequential numbering, corresponding to G96 and S97 according to Kabat numbering) of the HC sequence.

The heavy chain cleavage of anti-Jagged1 antibodies A, A-1, And A-2 was unexpected. An analysis of the amino acid sequence surrounding the cleavage site identified no known protease cleavage sites. The mechanism of the cleavage is unclear, and is not readily apparent from the sequences of the antibodies.

Example 8

Figure 15:
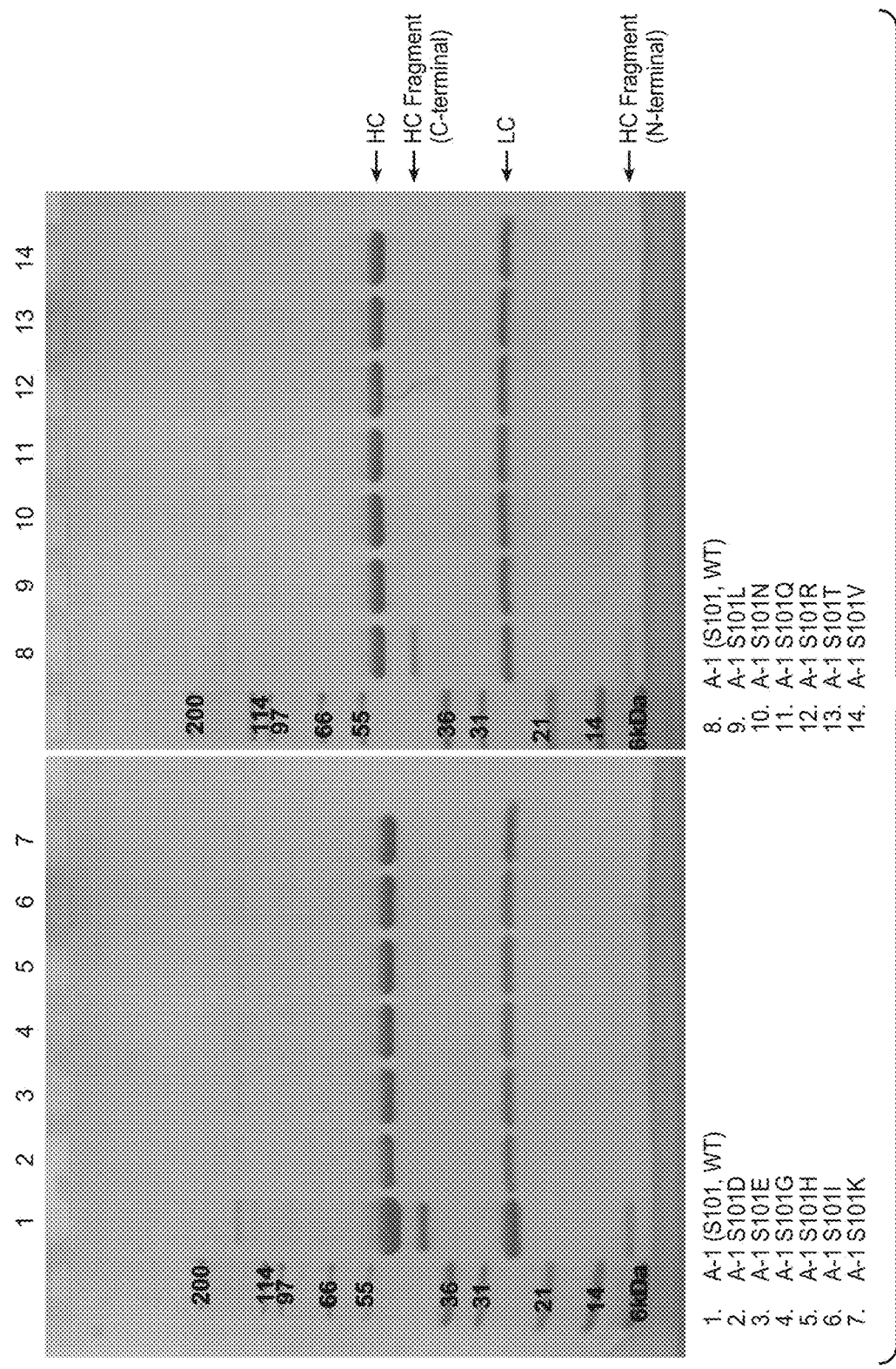
FIG. 15 shows the effect of amino acid changes at heavy chain S101 of the anti-Jagged1 antibodies on heavy chain cleavage.

Mutation of Heavy Chain S101 Reduces Cleavage of Anti-Jagged1 Antibody Heavy Chain Since the observed cleavage of the anti-Jagged1 antibodies was unexpected and the mechanism unclear, it was not known whether changes to the antibody sequence could prevent the cleavage, while retaining the affinity and efficacy of the antibody. In addition, it was not known what position(s) in the antibody sequence should be changed to prevent cleavage. To determine whether antibody cleavage could be prevented by changing the heavy chain sequence, a series of amino acid changes were made at heavy chain position S101 (sequential numbering of the heavy chain variable region sequence of SEQ ID NO: 17, corresponding to S97 according to Kabat numbering). The antibodies were expressed in mammalian cells and purified according to standard procedures. Cleavage was analyzed by SDS-PAGE as described in Example 7. The results are shown in FIG. 15. The amino acid changes at position S101 significantly reduced or eliminated HC cleavage, although some cleavage was detected with the S101H mutation (FIG. 15, lane 5). These results were confirmed by mass spectrometry, performed as described in Example 7.

To determine the effects of the changes on binding to a purified Jag1 extracellular domain protein fragment, mutant A-1 antibody binding affinities were measured using BIAcore. Table 3 shows a summary of the fragmentation and Jagged1 binding affinities for each of the mutant A-1 antibodies.

TABLE 3

Fragmentation and Jagged1 binding affinities of mutant A-1 antibodies

| mAb Variants | HC Fragmentation Detected? | | Jag 1 Binding (BIAcore) | | |
| --- | --- | --- | --- | --- | --- |
| | Mass Spec | SDS-PAGE | $k_a$ (1/Ms) | $k_d$ (1/s) | KD (M) |
| A-1 G100, S101 (WT) | yes | yes | 1.80E+05 | 1.44E−04 | 7.99E−10 |
| A-1 G100A, S101 | yes | yes | | | |
| A-1 G100, S101A | no | no | 1.46E+05 | 6.75E−04 | 4.62E−09 |
| A-1 G100, S101D | no | no | 1.02E+05 | 5.56E−04 | 5.47E−09 |
| A-1 G100, S101E | no | no | 1.67E+05 | 1.15E−03 | 6.88E−09 |
| A-1 G100, S101G | no | no | 1.54E+05 | 8.72E−04 | 5.67E−09 |
| A-1 G100, S101H | yes | yes | 1.27E+05 | 5.62E−04 | 4.43E−09 |
| A-1 G100, S101I | no | no | 9.88E+04 | 5.90E−04 | 5.97E−09 |
| A-1 G100, S101K | no | no | 1.18E+05 | 8.43E−04 | 7.16E−09 |
| A-1 G100, S101L | no | no | 8.34E+04 | 6.49E−04 | 7.79E−09 |
| A-1 G100, S101N | no | no | 1.36E+05 | 7.97E−04 | 5.87E−09 |
| A-1 G100, S101Q | no | no | 1.03E+05 | 5.82E−04 | 5.64E−09 |
| A-1 G100, S101R | no | no | 1.02E+05 | 6.90E−04 | 6.75E−09 |
| A-1 G100, S101T | no | no | 1.31E+05 | 3.41E−04 | 2.61E−09 |
| A-1 G100, S101V | no | no | 1.20E+05 | 5.80E−04 | 4.84E−09 |

As shown in Table 3, the changes to the amino acid residue at position 101 reduced cleavage to undetectable levels, except for S101H. In addition, since the mechanism of cleavage was unknown, a change to position 100, G100A, was also tested. The G100A mutant was still cleaved. See Table 3. Surprisingly, given that the mutations were made in HVR-H3, the S101 mutant antibodies retained the ability to bind Jagged1.

Example 9

Figure 16A:
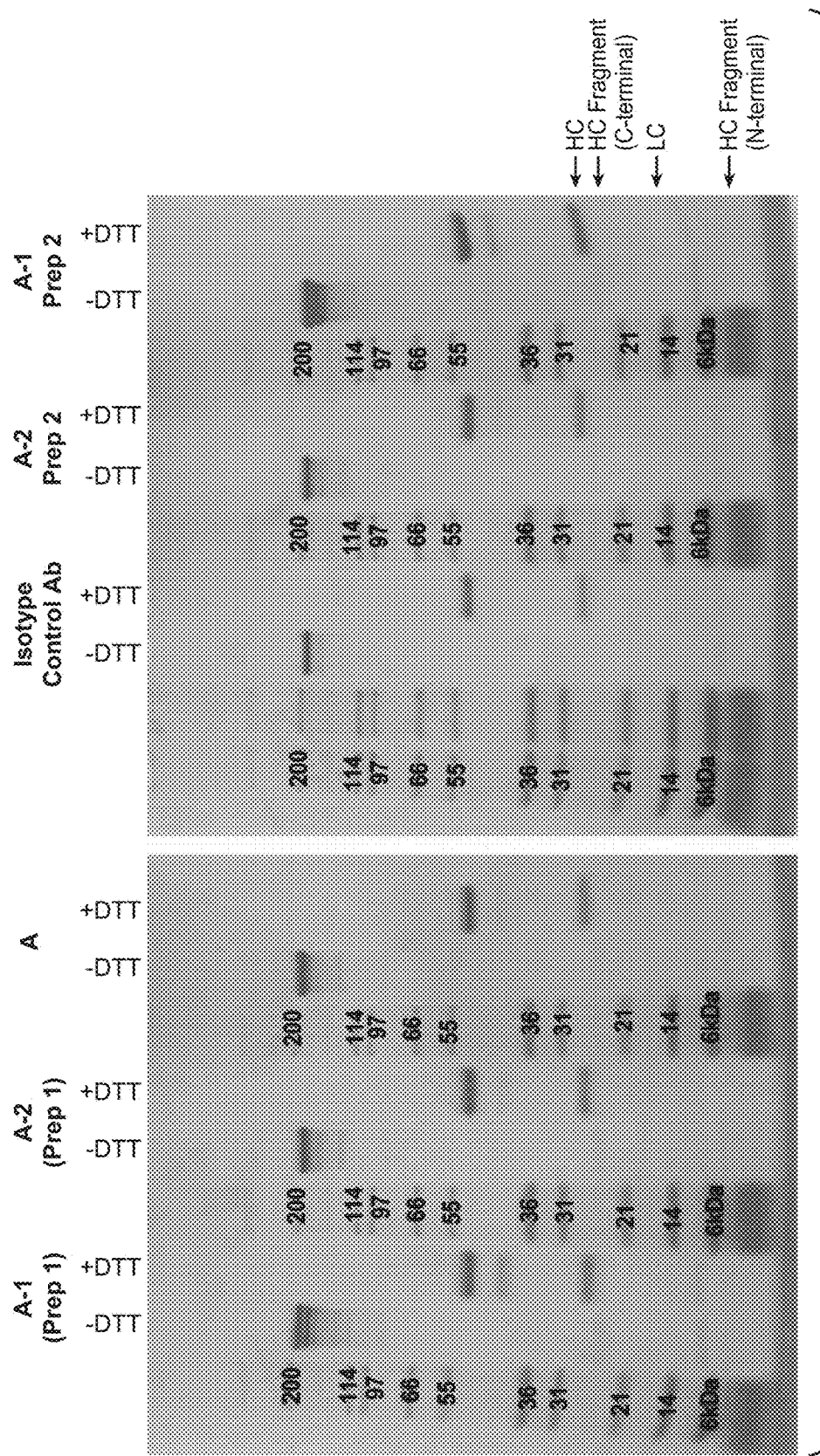
FIGS. 16A-B show (A) SDS-PAGE analysis of cleavage of anti-Jagged1 antibodies incubated at 70° C.; and (B) a summary of the percent heavy chain cleavage observed for each antibody preparation at 70° C. and at 95° C.
Figures 16B, 17A, 17B:
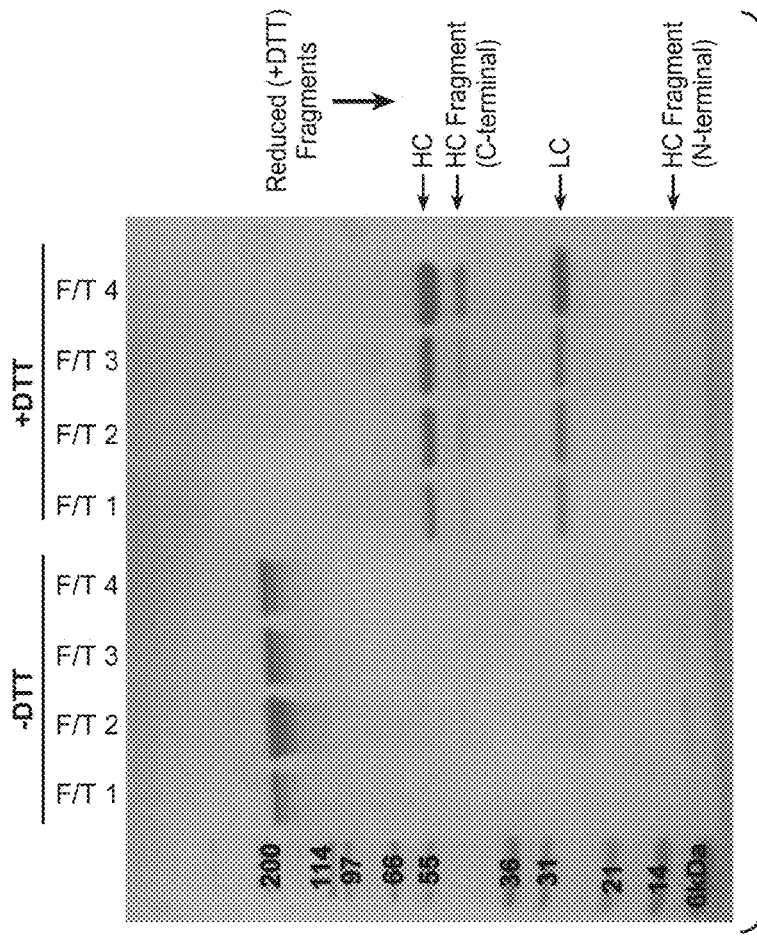
FIGS. 17A-B show (A) SDS-PAGE analysis of cleavage of anti-Jagged1 antibody A-1 after varying numbers of freeze-thaw cycles, and (B) the percent heavy chain cleavage observed under each condition.
Figure 16A:
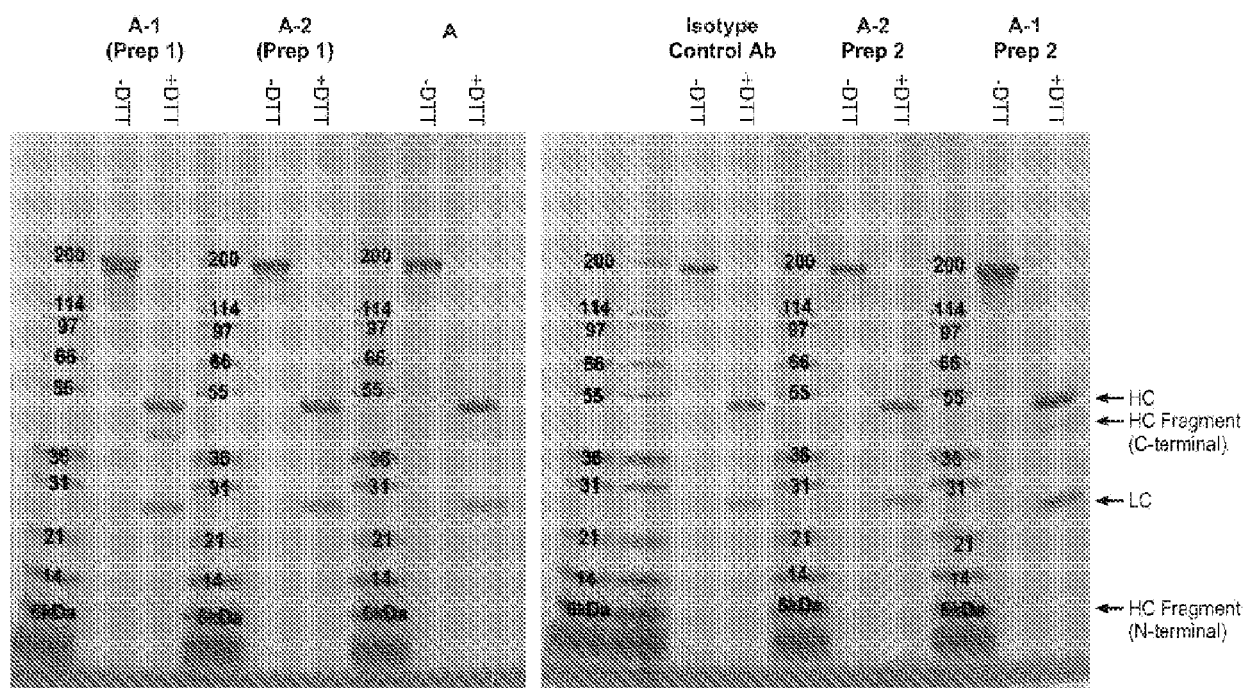
Figure 24:
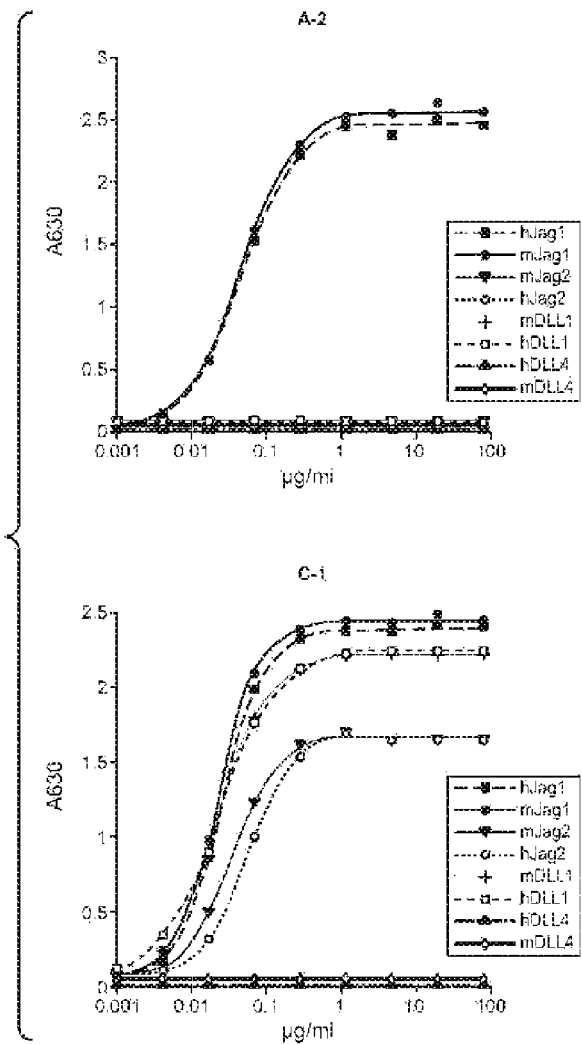

Effect of Temperature and Freeze-Thaw Cycling on Cleavage of Anti-Jagged1 Antibody Heavy Chain To assess whether anti-Jagged1 antibody cleavage is increased by incubation at increasing temperatures, various independent preparations of anti-Jagged1 antibodies A-1 (heavy chain and light chain variable region sequences of SEQ ID NOs: 17 and 18, respectively) and A-2 (heavy chain and light chain variable region sequences of SEQ ID NOs: 25 and 26, respectively), as well as an isotype control antibody (not anti-Jagged1), were incubated for 10 min at 70° C. or 95° C. The extent of cleavage was assessed using standard SDS-PAGE and protein staining. The results are shown in FIG. 16. Each of the anti-Jagged1 antibody preparations was cleaved at 70° C., while the control antibody was not (FIG. 16A). As summarized in the table (FIG. 16B), the extent of anti-Jagged1 cleavage was not significantly or consistently altered by incubation at 95° C. versus 70° C.

To assess whether cleavage resulted from freeze-thaw cycling of anti-Jagged1 antibody preparations, antibody A-1 (heavy chain and light chain variable region sequences of SEQ ID NOs: 17 and 18, respectively) was subjected to multiple rounds of freezing at −80° C. followed by thawing. 2 μg of each sample was then analyzed by SDS-PAGE and protein staining under non-reducing (−DTT) or reducing (+DTT) conditions, as indicated. The stained gel was imaged using a Biorad GelDoc Easy Imager instrument and densitometry analysis was performed using Biorad Image Lab software. The results of that experiment are shown in FIG. 17. F/T 1 refers to the original sample, with increasing numbers indicating the number of additional rounds of freeze-thaw cycles. For each cycle, the A-1 antibody was frozen at −80° C. and then thawed at room temperature. An aliquot was removed for SDS-PAGE. The freeze/thaw was repeated twice more for a total of 3 freeze/thaw cycles, with aliquots being removed after each thaw step. The table (FIG. 17B) summarizes the percentage of cleavage under each condition. The experiment revealed that additional rounds of freeze-thaw had little impact on the percentage of cleavage.

Example 10

Jagged1 Blocking Activity of A-1 and A-1(S101T) In Vitro

In vitro co-culture assays of Jag1-induced Notch reporter activity were performed to measure the Jag1 blocking activity of A-1 (heavy chain and light chain variable region sequences of SEQ ID NOs: 17 and 18, respectively) and A-1(S101T) (heavy chain and light chain variable region sequences of SEQ ID NOs: 33 and 34, respectively). U87MG cells, which express high levels of Notch2, were co-transfected with a Notch-responsive TP-1 (12× CSL) Firefly (FF) luciferase reporter and a constitutively expressed Renilla luciferase reporter (pRL-CMV, Promega) to control for transfection efficiency. See Wu et al., 2010, Nature 464: 1052-1057. Anti-Jagged1 antibody A-1 or A-1 (S101T), isotype control antibody, 5 μM DAPT (Calbiochem), or DMSO vehicle control was added with ligand-expressing cells (NIH-3T3 cells stably transfected with human Jag1 or a no ligand control) 6 hours after transfection. Luciferase activities were measured after 20 hours of co-culture (Promega, Dual Glo Luciferase). Typically, four replicates were analyzed for each condition, and values were expressed as relative luciferase units (Firefly signal divided by the Renilla signal) and graphed as a percentage of Jag1-induced activity per anti-Ragweed control.

Figure 18A:
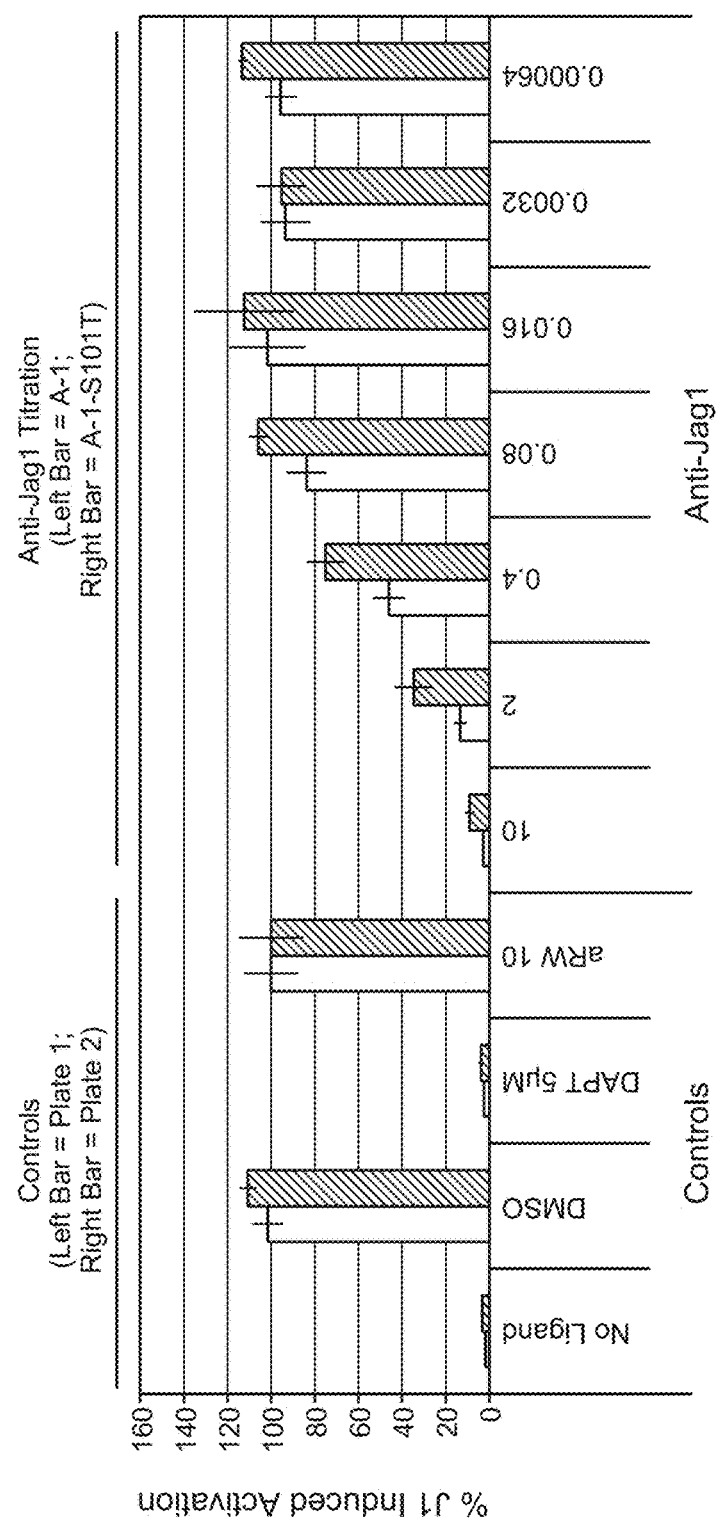
FIGS. 18A-C show (A) inhibition of Jagged1-induced activation by anti-Jagged1 antibodies A-1 (left bars) and A-1(S101T) (right bars) at various concentrations. Panels (B) and (C) shows average firefly luciferase values and average Renilla luciferase values, respectively, which were used to calculate the data in (A), as described in Example 10.
Figure 18B:
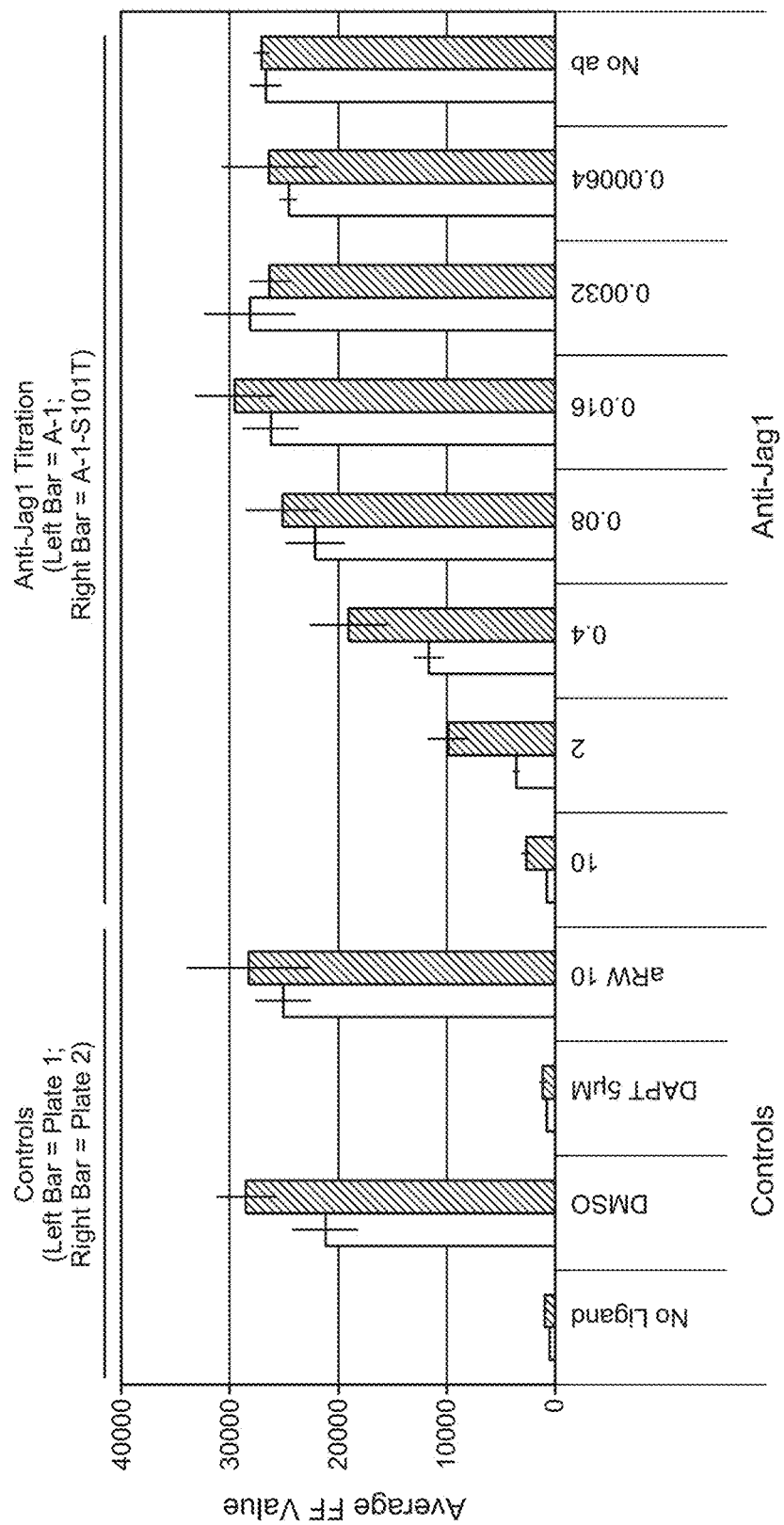
Figure 18C:
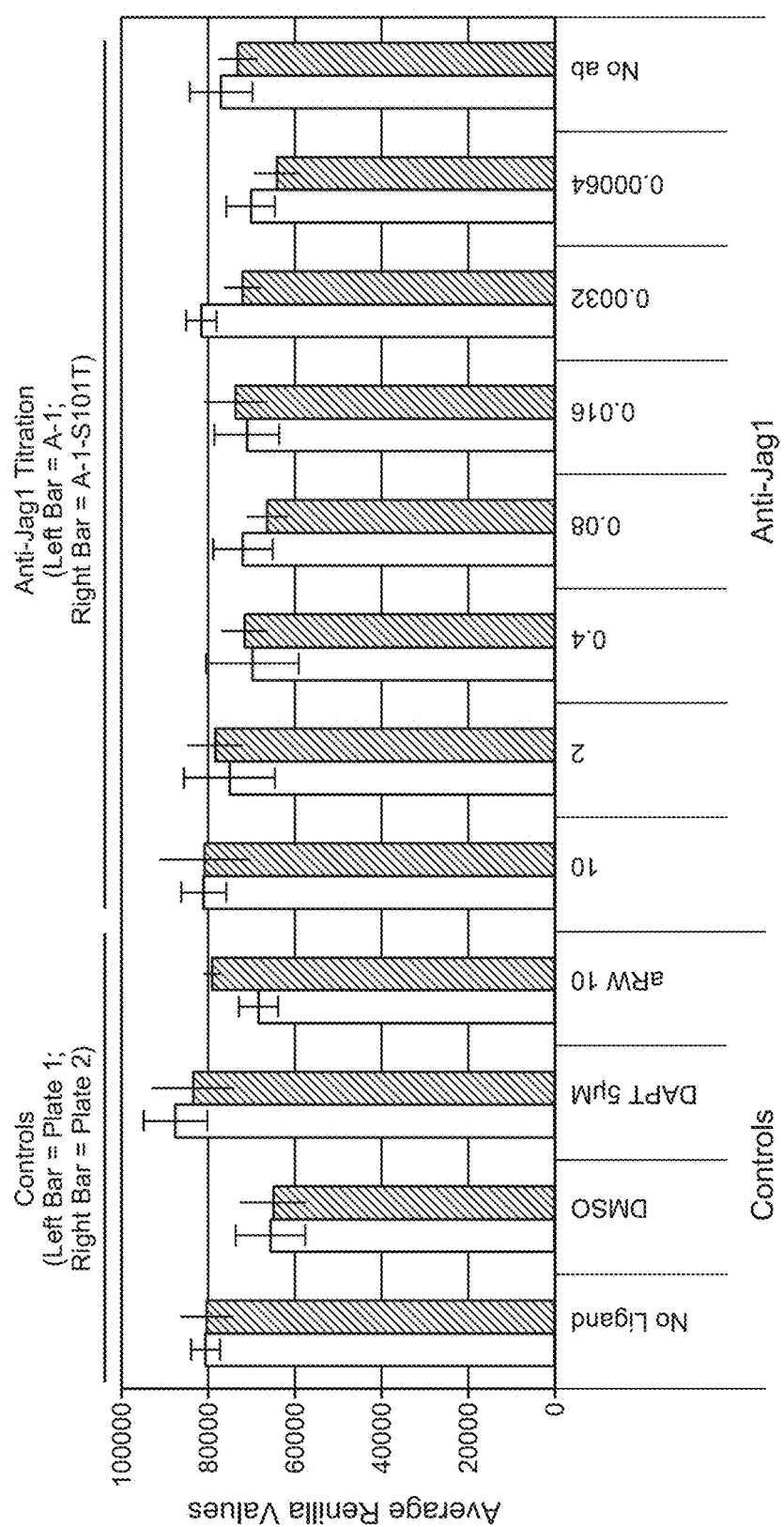

The results of that experiment are shown in FIG. 18. FF and Renilla luciferase measurements were taken (FIGS. 18B and C, respectively) according to standard methods, and the FF to Renilla luciferase ratios were graphed as a normalized measurement of Jag1-induced Notch activity (FIG. 18A). The results show that A-1 and A-1(S101T) both inhibit Jag1-induced Notch signaling in a dose-dependent manner. See FIGS. 18A and B. Thus, A-1(S101T) retains the anti-Jagged1 blocking activity of parental antibody A-1.

Example 11

Jagged1 Blocking Activity of A-1 and A-1(S101T) In Vivo

To assess Jagged1 blocking activity of anti-Jagged1 antibodies in vivo, the club and ciliated cell composition of mouse lung bronchiolar epithelium was measured after dosing mice with control or anti-Jagged1 antibodies. Wild-type, eight-week old BALB/c female mice (three mice per group) were dosed on day 0 as follows (all groups contained anti-Jagged2 antibody (B-3) to sensitize the bronchiolar epithelium to reveal clearly measurable effects of anti-Jagged1 activity):

1. Control 1×—isotype control (15 mg antibody per kg mouse body weight)+anti-Jag2 B-3 (15 mg/kg; heavy chain and light chain variable region sequences of SEQ ID NOs: 41 and 42, respectively)
2. A-1 1×—anti-Jag1 A-1 (15 mg/kg; heavy chain and light chain variable region sequences of SEQ ID NOs: 17 and 18, respectively)+anti-Jag2 B-3 (15 mg/kg)
3. A-1 0.5×—anti-Jag1 A-1 (7.5 mg/kg)+anti-Jag2 B-3 (15 mg/kg)
4. A-1 0.25×—anti-Jag1 A-1 (3.75 mg/kg)+anti-Jag2 B-3 (15 mg/kg)
5. A-1-S101T 2×—anti-Jag1 A-1(S101T) (30 mg/kg; heavy chain and light chain variable region sequences of SEQ ID NOs: 33 and 34, respectively)+anti-Jag2 B-3 (15 mg/kg)
6. A-1-S101T 1×—anti-Jag1 A-1(S101T) (15 mg/kg)+anti-Jag2 B-3 (15 mg/kg)
7. A-1-S101T 0.5×—anti-Jag1 A-1(S101T) (7.5 mg/kg)+anti-Jag2 B-3 (15 mg/kg)
8. A-1-S101T 0.25×—anti-Jag1 A-1(S101T) (3.75 mg/kg)+anti-Jag2 B-3 (15 mg/kg)

On day 5, lungs were harvested, inflated, fixed and stained for immunofluorescence (IF) as follows. Lungs were inflated with 4% PFA in PBS. The entire lung was transferred to 10% neutral buffered formalin (NBF) and fixed over-night at room temperature. Fixed lungs were transferred to 70% ethanol for at least 24 hours. The lungs were paraffin embedded and sectioned at 5 μm. Immunofluorescence staining for ciliated and Clara cells was as follows. Slides were de-paraffinized and antigens were retrieved by boiling the slides in citrate buffer (Dako S1700) in a pressure cooker for 15 minutes at 125° C. Slides were briefly rinsed in 2×PBS, and then permeablized with 0.2% Triton-X100 in PBS for 45 minutes or 3×15 minutes. Sections were blocked with 5% FBS/2% BSA for 1 hour. Slides were then incubated with goat anti-CC10 (1:1000) and mouse anti-acetylated alpha tubulin (1:200) in blocking buffer for 2 to 3 hours or overnight. Slides were washed 3 times for 15 minutes with PBS. Slides were incubated with secondary antibodies for 1 hour (Invitrogen Alexa Fluor secondary antibodies diluted 1:1000), then rinsed twice for 15 minutes with PBS. Nuclei were stained with DAPI (0.5 ug/ml) for 15 minutes. Slides were then rinsed twice for 15 minutes with PBS and coverslipped.

Figure 19:
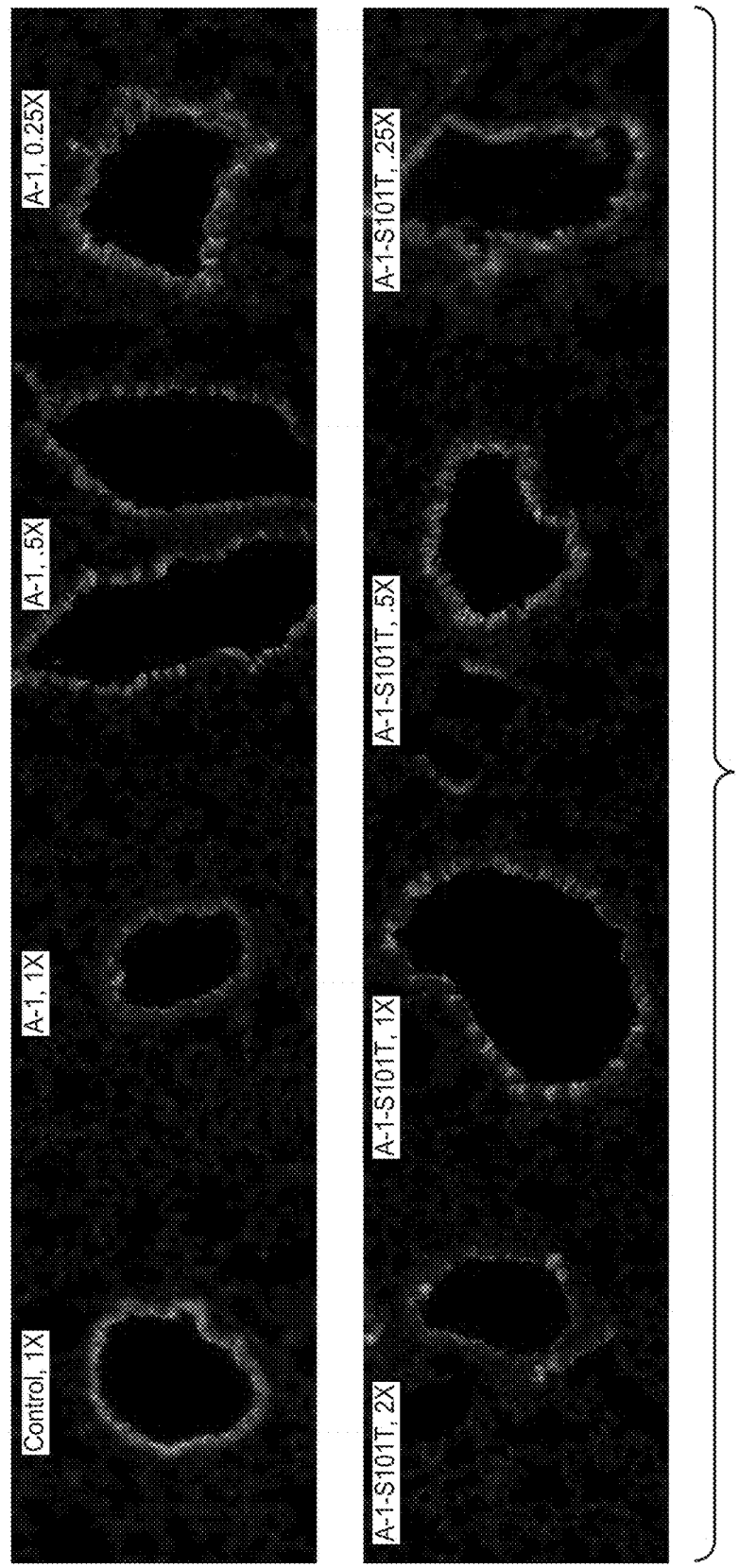
FIG. 19 shows immunofluorescent staining of ciliated cells (as marked by immunofluorescent detection of alpha-tubulin in red) and club cells (as marked by immunofluorescent detection of CC10 in green) in the bronchiolar epithelium of mice administered anti-Jagged2 antibodies in combination with anti-Jagged1 antibody A-1 or A-1(S101T), or an isotype control, as described in Example 11.

The results of that experiment are shown in FIG. 19. Blocking Jagged1 and Jagged2 signaling causes an increase in the number of ciliated cells (as marked by immunofluorescent detection of alpha-tubulin in red) and a decrease in the number of club cells (as marked by immunofluorescent detection of CC10 in green) in the mouse bronchiolar epithelium. Blocking both Jagged1 plus Jagged2 results in a near complete loss of club cells, such that the resulting epithelium consists primarily of ciliated cells (red; see "A-1, 1×" and "A-1-S101T, 2×" in FIG. 19). A-1 and A-1(S101T) both inhibited Jagged1-induced Notch signaling in vivo in a dose-dependent manner. Thus, A-1(S101T) retains the anti-Jagged1 blocking activity of parental antibody A-1 in vivo.

Example 12

Anti-Jagged1 Antibodies A-1 and A-1(S101T) Inhibit Growth of Liver Cancer Tumors In Vivo A human patient-derived liver cancer tumor, LIV#78 (Genendesign, China), was grown as a subcutaneous xenograft in BALB-c nude immunocompromised mice. When tumors grew to between 150 to 200 mm$^3$, the mice were grouped into seven treatment groups with ten mice per group and dosed once per week (except for group 5, which was dosed once every three weeks) at the indicated dose (in mg of antibody per kg of mouse body weight) of the indicated antibody (A-1(S101T) antibody has the heavy chain and light chain sequences of SEQ ID NOs: 51 and 53, respectively; "A-1-DANG(effectorless)" has the heavy and light chain sequences of SEQ ID NOs: 52 and 53, respectively; and A-1 antibody has the heavy chain and light chain sequences of SEQ ID NOs: 81 and 53, respectively). See FIG. 20B. Tumor volumes were assessed by caliper measurements (length×width×height/2).

Figures 20A, 20B:
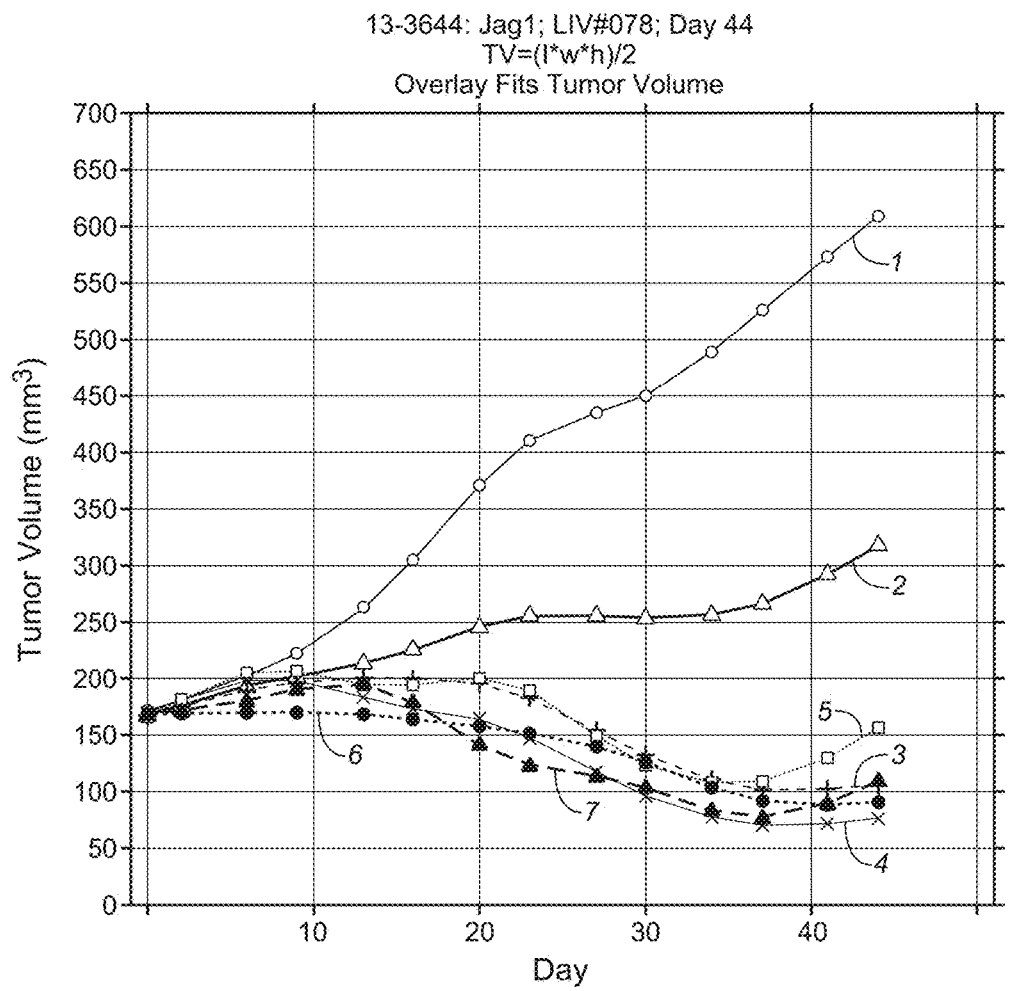
FIGS. 20A-B show (A) a LME (linear mixed effects) graph of tumor volume in a liver cancer xenograft model mice treated with anti-Jagged1 antibody A-1 or A-1(S101T), and (B) the treatment groups shown in (A) and the dose, tumor volume on the last day of the study (day 44), AUC/Day % TGI (area under the curve per day percentage tumor growth inhibition (TGI) relative to control, in which lower and upper refer to the lowest and uppermost, respectively, % TGI values for individual animals in each group), tumor doubling time in days (TTP 2×), and the number of mice showing a partial response during the experiment (PR).

FIG. 20A shows a LME (linear mixed effects) graph of tumor volume in each treatment group over the course of the study. FIG. 20B summarizes the growth statistics, group identities and dosing regimens. The anti-Jagged1 A-1 and A-1(S101T) antibodies significantly inhibited liver cancer growth in vivo; multiple PRs (partial responses) were observed with each of the anti-Jagged1 antibodies. Likewise, none of the anti-Jagged1 treated groups showed a doubling of tumor volume during the 44 days of the study, whereas the control group showed a time to progression of tumor doubling (TTP 2×) of 18.5 days. See FIG. 20B. The percentage of tumor growth inhibition (% TGI, where "lower" and "upper" refer to the lowest and uppermost % TGI measurements, respectively, for individual animals in each group) as a function of area under the curve per day (AUC/day) compared to the control group depended on the dose of anti-Jagged1 A-1-S101T, consistent with tumor growth inhibition reflecting the extent of Jagged1 inhibition. Likewise, inhibition of tumor growth was similar using A-1 or A-1(S101T). Compare, e.g., groups 3 and 7, FIG. 20B. Tumor growth inhibition did not depend on antibody effector function because a heavy chain N297G mutant form of A-1, which lacks effector function, inhibited tumor growth as effectively as A-1. Compare groups 6 and 7, FIG. 20B.

Figures 21A, 21B:
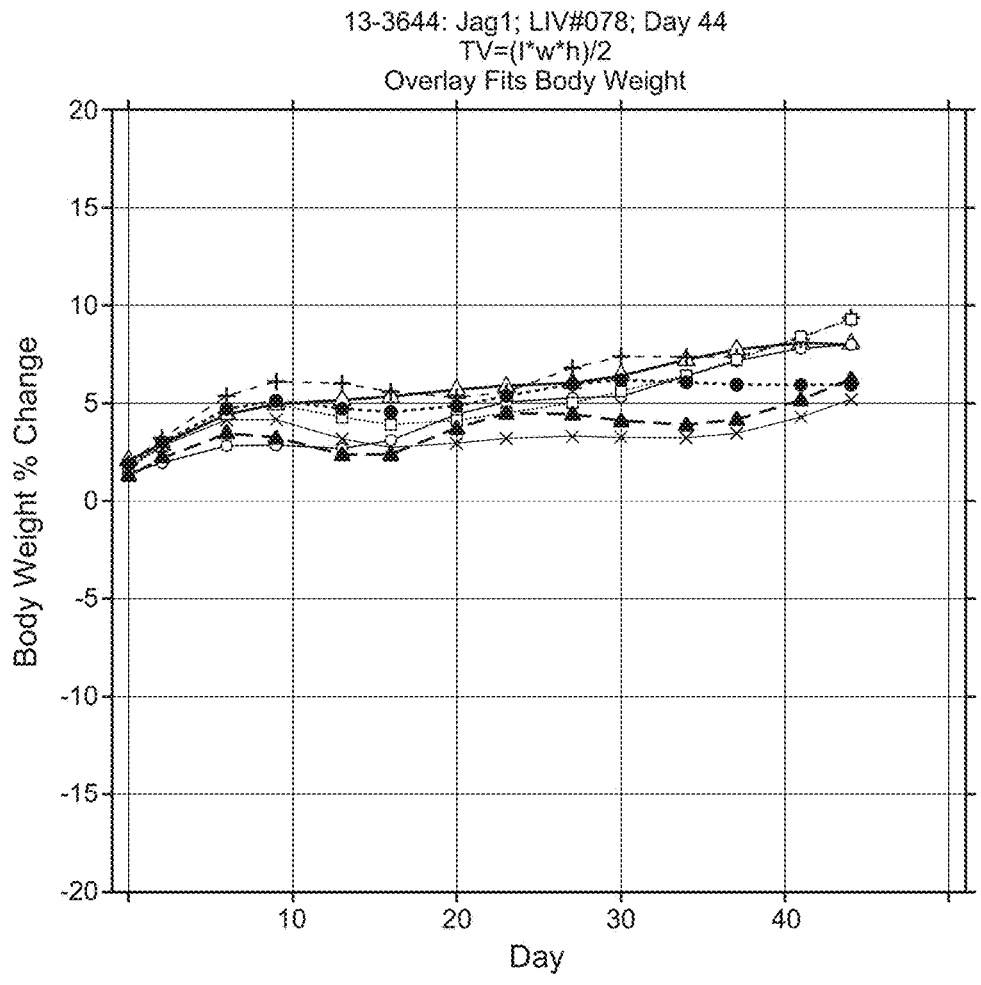
FIGS. 21A-B show (A) a LME (linear mixed effects) graph of mouse body weight over time for the mice shown in FIG. 20, and (B) the treatment groups shown in (A) and the dose, % change in body weight on the last day of the study (% BW Last Day), the maximum % change in body weight (Max % BW), and the day on which the maximum change in bodyweight occurred (Max % BW Day), and the (AUC/Day (lower,upper)).

FIG. 21A shows a LME (linear mixed effects) graph of mouse body weight over time for the mice shown in FIG. 20. FIG. 20B shows various body weight parameters for the treatment groups, including the % change in body weight on the last day of the study (% BW Last Day), the maximum % change in body weight (Max % BW), and the day on which the maximum change in bodyweight occurred (Max % BW Day), and the (AUC/Day (lower,upper)). The body weight graphs for the treatment groups, including the control group, are statistically indistinguishable, indicating that anti-Jagged1 treatment was well-tolerated.

Example 13

Blocking Jagged1 Inhibits Goblet Cell Metaplasia In Vivo

Following a 35 day period of sensitization to intraperitonealy injected ovalbumin, mice were challenged with aerosolized ovalbumin for 7 consecutive days, after which they were sacrificed and analyzed for the number of goblet cells. Mice were treated with control, anti-Jagged1 A-2 antibody (with murine IgG2a Fc), anti-Jagged2 B-3 antibody (with murine IgG2a Fc) or the combination of anti-Jagged1+anti-Jagged2 antibodies 24 hours and 96 hours after the first aerosol challenge.

Figure 23A:
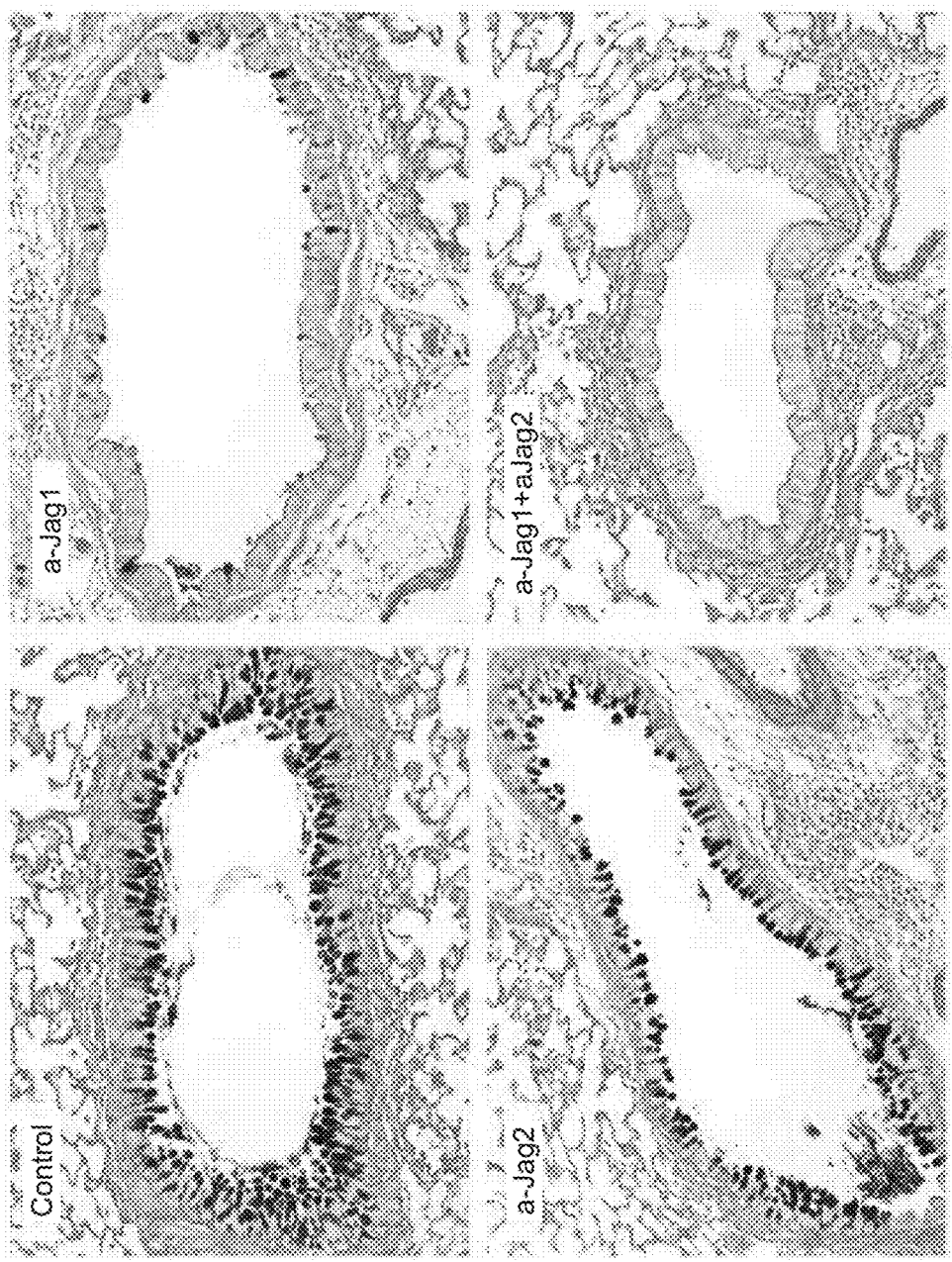
FIGS. 23A-C show (A) Periodic Acid-Schiff staining of lung airways of control, anti-Jagged1, anti-Jagged2 or the combination of anti-Jagged1+anti-Jagged2 treated mice, (B) quantification of the number of goblet cells in the airways of the different treatment groups, and (C) inflammation index as assessed be H&E staining.
Figure 23B:
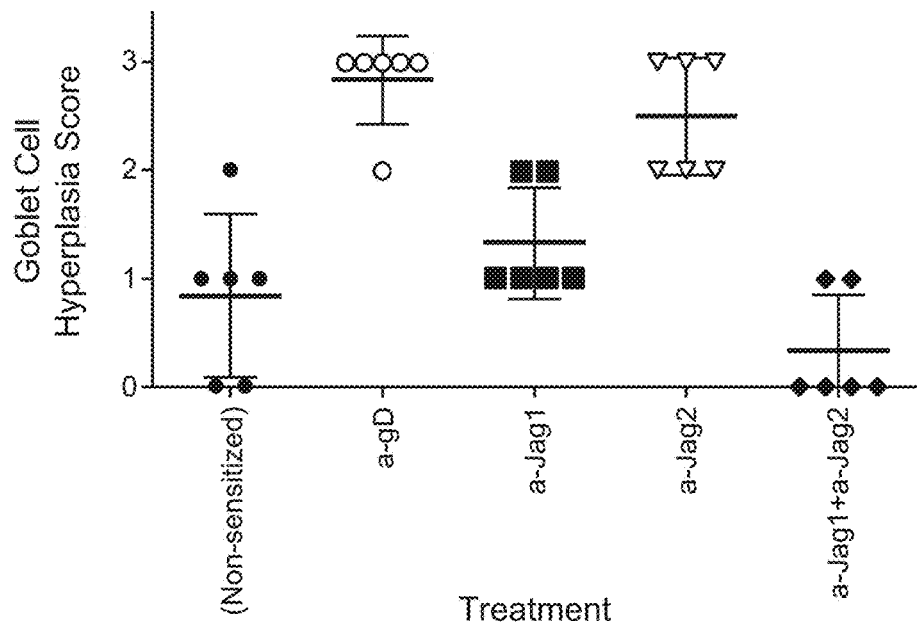
Figure 23C:
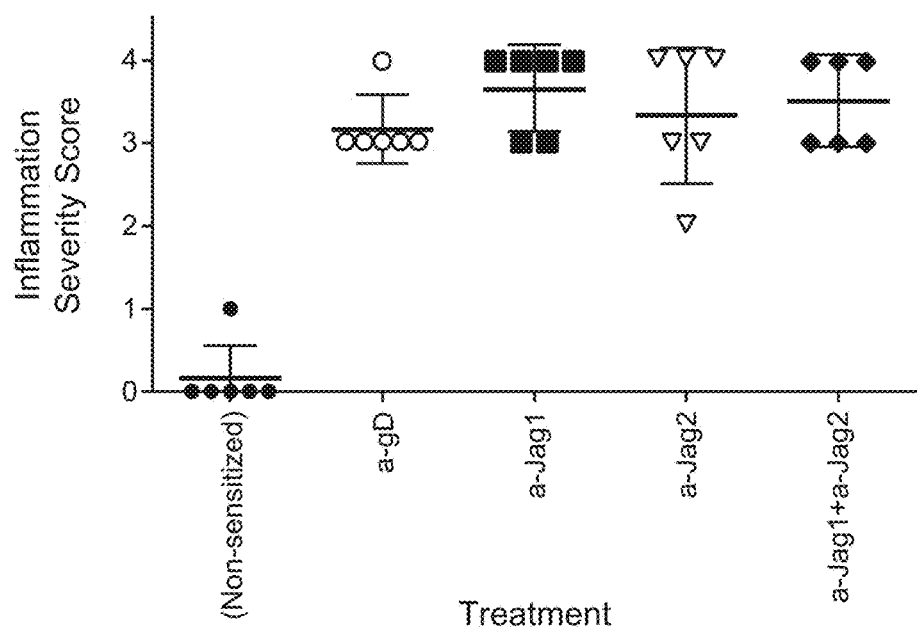

FIG. 23A shows periodic acid-Schiff staining of lung airways in the mice treated with anti-Jagged1, anti-Jagged2, anti-Jagged1+anti-Jagged2, or control antibody. FIG. 23B shows quantification of the goblet cells in the airways of the different treatment groups. An abundance of goblet cells are evident in the control and anti-Jagged2 groups. Few goblet cells were present in the anti-Jagged1 group and practically no goblet cells were detected in the anti-Jagged1+anti-Jagged2 group. FIG. 23C shows the inflammation index as assessed by Haematoxylin Eosin (H&E) staining Treatment with either Jagged1 or -2 blocking antibody does not affect inflammation in the lungs.

Jagged1-induced Notch signaling biases cell fate in the airways towards a secretory cell (including goblet cell) fate and away from a ciliated cell fate. Jagged1 signaling is important for maintaining the secretory cell fate, and inhibition of Jagged1 signaling prevented goblet cell metaplasia. We also showed that the club cell-to-ciliated cell conversion is direct and did not involve cell division (data not shown). Club cells give rise to goblet cells in the lung. This transdifferentiation of one cell type to another occurred in the adult lung and is distinct from cell fate choices that involve progenitor cell division, such as after damage or during development. Goblet cell metaplasia or excess mucus is a hallmark of several airway diseases, such as asthma, cystic fibrosis, COPD and Barrett's esophagus. These Jagged inhibition results provide the basis for therapeutic applications involving use of Jagged1 or Jagged2 inhibitors for prevention or reversal of goblet cell metaplasia and for treatment of conditions characterized by excess mucus, as in airway diseases (e.g., asthma, COPD, cystic fibrosis) and Barrett's esophagus.

Example 14

Specific Binding of Anti-Jagged1 and Anti-Jagged2 Antibodies

Figure 24:
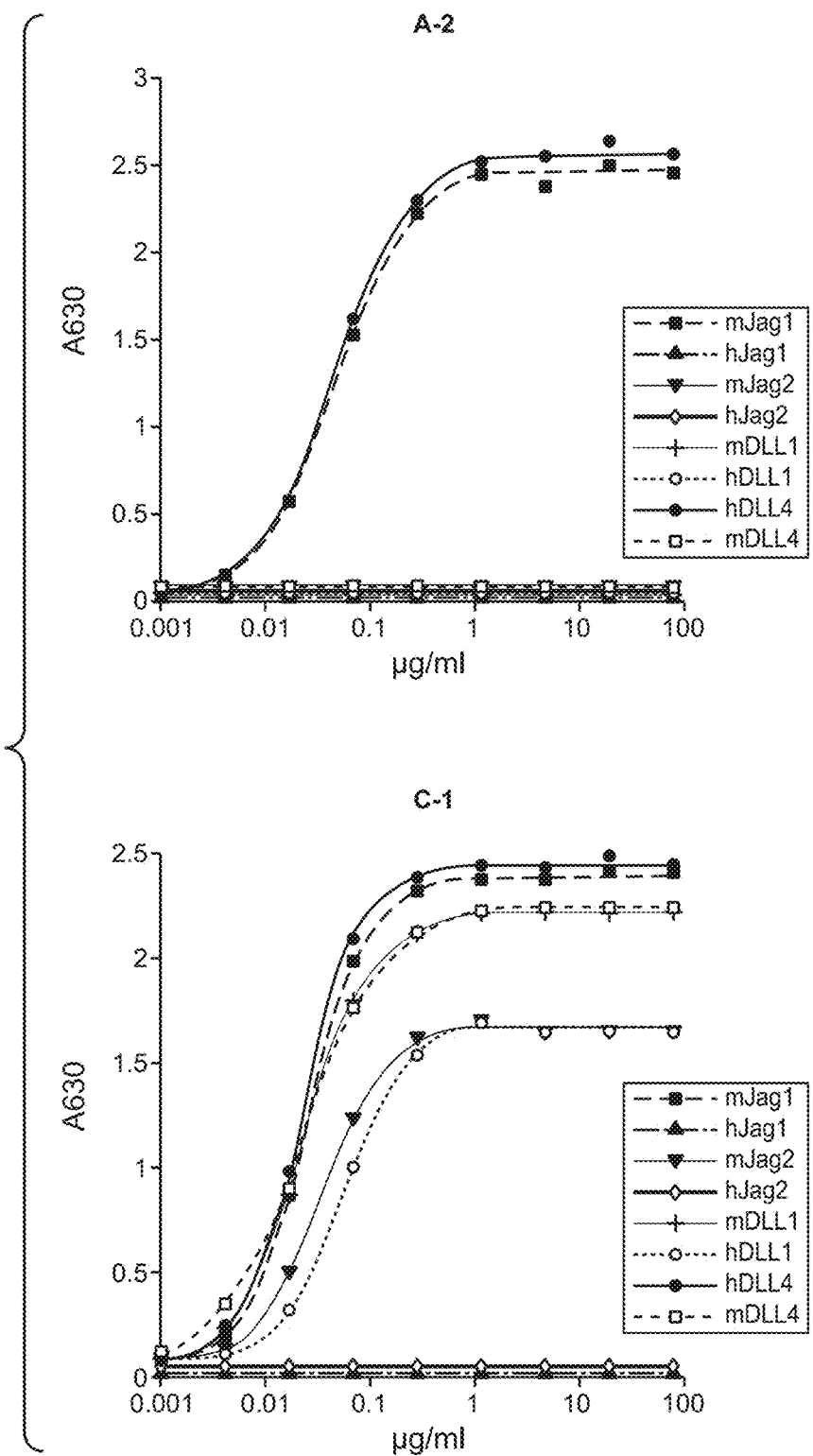
FIG. 24 shows binding of (left) anti-Jagged1 antibody A-2 and (right) anti-Jagged1/2 antibody C-1, to human Jagged1, murine Jagged1, human Jagged 2, murine Jagged2, human DLL1, murine DLL1, human DLL4 and murine DLL4.

Antibodies A-2 (FIG. 24, left panel) and C-1 (FIG. 24, right panel) were tested for binding to recombinant purified Notch ligands human Jagged1 (hJag-1), human Jagged2 (hJag-2), murine Jagged2 (mJag-2), human Delta-like 1 (hDLL1), murine Delta-like 1 (mDLL1), and human Delta-like 4 (hDLL4) using a standard enzyme-linked immunosorbent assay (ELISA). 1 µg/ml of Notch ligand protein (as indicated) in PBS, pH7.4, was coated onto ELISA plates (Nunc Maxisorp) at 40° C. overnight. Plates were blocked with Casein blocker in PBS (Pierce) for one hour at room temperature. Serial 3-fold dilutions of antibody IgGs (as indicated) in PBST buffer (PBT buffer (PBS+0.05% (v/v) Tween 20) with 0.5% (w/v) BSA) were added to the plates and incubated for one hour at room temperature. The plates were then washed with PBST and bound antibodies were detected with peroxidase-conjugated goat anti-human Fab specific IgG (Sigma). TMB substrate (3,3',5,5'-tetramethylbenzidine) was used and absorbance at 630 nM was read using a standard ELISA plate reader. Absorbance was plotted against concentrations of IgGs using KaleidaGraph (Synergy Software). FIG. 24 shows the results, with $A_{630}$ on the y-axis representing the extent of binding.

Antibody A2 bound human and murine Jagged1, but did not bind human Jagged 2, murine Jagged2, human DLL1, murine DLL1, human DLL4, or murine DLL4 (FIG. 24, left panel). Antibody C1 bound human and murine Jagged1, human and murine DLL1, human and murine Jagged2, but did not bind human or murine DLL4 (FIG. 24, right panel).

Antibody binding affinities and rate constants were measured by Surface Plasmon Resonance (SPR) using a BIAcore™-T200 instrument. Human IgG1 antibodies were captured by mouse anti-human IgG coated on the CM5 sensor chip to achieve approximately 150 response units (RU). For kinetic or affinity measurements, four-fold serial dilutions of human Jagged1, murine Jagged1, human Jagged2, murine Jagged2, human DLL1, murine DLL1, human DLL4, murine DLL4, and rat Jagged1 were injected in HBS-T buffer (0.01 M HEPES pH 7.4, 0.15 M NaCl, 0.05% v/v Surfactant P20, GE Healthcare) at 25° C. with a flow rate of 30 ml/min. The ligand fragments were the DSL-EGF1-4 fragments, except for rat Jagged1, which was purchased from R&D Systems. For kinetic analysis, association rates ($k_{on}$) and dissociation rates ($k_{off}$) were calculated using a simple one-to-one Langmuir binding model (BIAcore T200 Evaluation Software version 2.0). The equilibrium dissociation constant ($k_d$) was calculated as the ratio $k_{off}/k_{on}$. For affinity analysis, $K_d$ was calculated using a Steady State Affinity model (BIAcore T200 Evaluation Software version 2.0).

Table 3 summarizes the binding constants for antibodies A-2, B-3, C-1, A-1, and A-1 S101T binding to purified human Jagged1, murine Jagged1, human Jagged2, murine Jagged2, human DLL1, murine DLL1, human DLL4, murine DLL4, and/or rat Jagged1. n.d.=not detected, n.t.=not tested. Antibodies A-2, A-1, and A-1-S101T.NG (antibody A-1S101T with N297G mutation) specifically bound to human and murine Jagged1 with high affinity. Antibodies A-1 and A-1-S101T.NG bound rat Jagged1 with high affinity also. Antibody B-3 specifically bound to human and murine Jagged2 with high affinity. Antibody C-1 specifically bound to human and murine Jagged1 and Jagged 2. Antibodies B-3 and C-1, but not antibody A-2, showed some binding to human and mouse DLL1. None of the antibodies tested bound human or mouse DLL4.

Example 15

Pharmacokinetics of Anti-Jagged1 A-1-S101T Antibody

The pharmacokinetic profile of anti-Jagged1 A-1-S101T antibody following a single intravenous injection at 1, 10, and 100 mg/kg were evaluated in female Balb/c nude mice (Charles River Laboratories, Hollister, Calif.). The mice were 5-8 weeks old and weighed approximately 17.3-21.8 g. Serum samples were collected and antibody concentrations were analyzed by specific enzyme linked immunosorbent assays (ELISA). The specific ELISA was coated with JAG1 extracellular domain-Histidine and detected with goat anti-human Fc. The assay sensitivity has a less than standard value of 6.25 ng/mL. Pharmacokinetic parameters were estimated using a non-compartmental model with Phoenix™ WinNonlin® (v.6.3; Pharsight Corporation; Mountain View, Calif.). All PK analysis was based on naïve pool of individual animal data.

Figure 25:
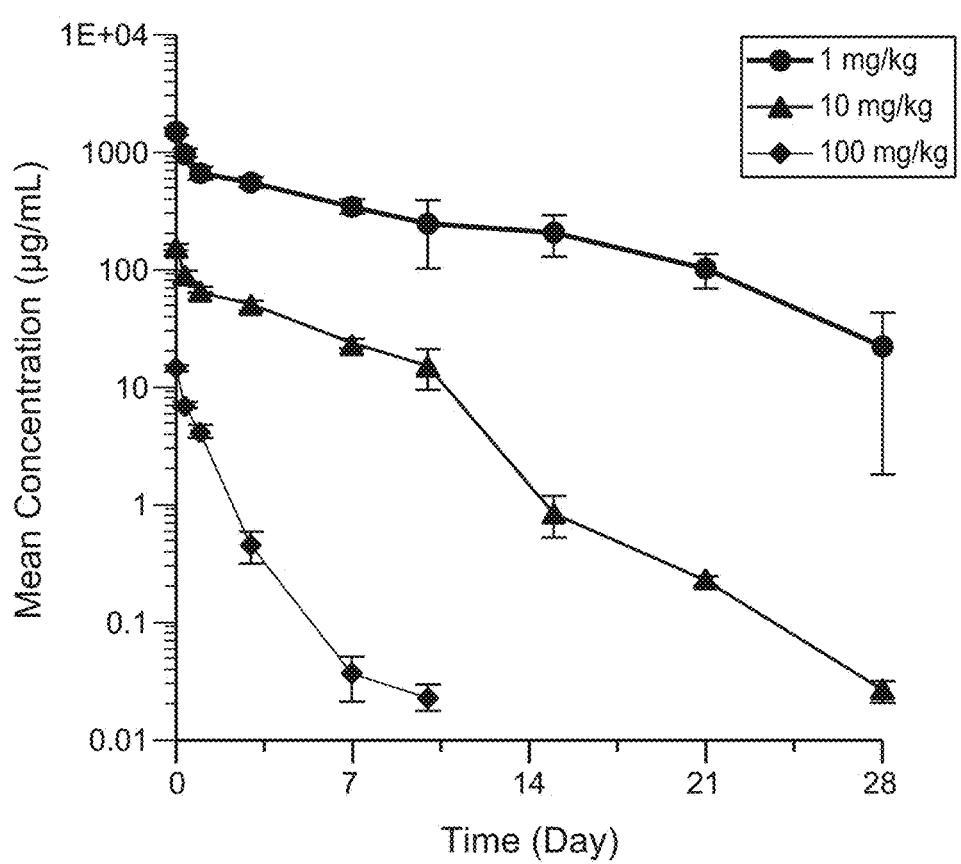
FIG. 25 shows clearance of anti-Jagged1 A-1-S101T antibody following a single intravenous administration of three different doses of the antibody in mice.

A greater than dose proportional increase in exposure was observed following IV administration of anti-Jagged1 A-1-S101T antibody within the dose range of 1 and 100 mg/kg, suggesting a target-mediated clearance mechanism of the antibody (FIG. 25 and Table 4). The clearance values ranged from approximately 13 to 75 mL/day/kg.

TABLE 3

Binding constants for anti-Jagged antibodies

| | A-2 | | | B-3 | | | C-1 | | |
|---|---|---|---|---|---|---|---|---|---|
| | $k_{on}$ (1/Ms) | $k_{off}$ (1/s) | $K_d$ (M) | $k_{on}$ (1/Ms) | $k_{off}$ (1/s) | $K_d$ (M) | $k_{on}$ (1/Ms) | $k_{off}$ (1/s) | $K_d$ (M) |
| hJag1 | 2.42E+05 | 9.23E−05 | 3.82E−10 | n.d. | n.d. | >1.00E−06* | 2.90E+05 | 9.00E−05 | 3.10E−10 |
| mJag1 | 3.85E+05 | 5.77E−05 | 1.50E−10 | n.d. | n.d. | >1.00E−06* | 8.69E+05 | 1.54E−04 | 1.77E−10 |
| hJag2 | n.d. | n.d. | n.d. | 4.58E+06 | 1.88E−04 | 4.10E−11 | 7.64E+06 | 5.56E−04 | 7.28E−11 |
| mJag2 | n.d. | n.d. | n.d. | 7.71E+05 | 4.40E−05 | 5.71E−11 | 1.16E+06 | 8.03E−05 | 6.92E−11 |
| hDLL1 | n.d. | n.d. | n.d. | n.d. | n.d. | 3.49E−07* | n.d. | n.d. | 7.83E−08* |
| mDLL1 | n.d. | n.d. | n.d. | n.d. | n.d. | 7.23E−08* | n.d. | n.d. | 5.55E−08* |
| hDLL4 | n.d. | n.d. | n.d. | n.d. | n.d. | n.d. | n.d. | n.d. | n.d. |
| mDLL4 | n.d. | n.d. | n.d. | n.d. | n.d. | n.d. | n.d. | n.d. | n.d. |
| rJag1 | n.t. | n.t. | n.t. | n.t. | n.t. | n.t. | n.t. | n.t. | n.t. |

| | A-1 | | | A-1.S101T.NG | | |
|---|---|---|---|---|---|---|
| | $k_{on}$ (1/Ms) | $k_{off}$ (1/s) | $K_d$ (M) | $k_{on}$ (1/Ms) | $k_{off}$ (1/s) | $K_d$ (M) |
| hJag1 | 2.91E+04 | 2.25E−04 | 7.75E−09 | 2.09E+04 | 5.88E−04 | 2.82E−08 |
| mJag1 | 1.59E+05 | 7.42E−05 | 4.57E−10 | 9.51E+04 | 6.22E−04 | 6.54E−09 |
| hJag2 | n.d. | n.d. | n.d. | n.d. | n.d. | n.d. |
| mJag2 | n.d. | n.d. | n.d. | n.d. | n.d. | n.d. |
| hDLL1 | n.t. | n.t. | n.t. | n.t. | n.t. | n.t. |
| mDLL1 | n.t. | n.t. | n.t. | n.t. | n.t. | n.t. |
| hDLL4 | n.t. | n.t. | n.t. | n.t. | n.t. | n.t. |
| mDLL4 | n.t. | n.t. | n.t. | n.t. | n.t. | n.t. |
| rJag1 | 4.34E+04 | 9.80E−07 | 2.26E−11 | 4.55E+04 | 1.97E−04 | 4.32E−09 |

TABLE 4

Pharmacokinetic properties of anti-Jagged1 A-1-S101T antibody

| Treatment | ELISA | $C_{max}$ (µg/mL) | $AUC_{last}$ (day * µg/mL) | $AUC_{inf}$ (day * µg/mL) | CL (mL/day/kg) | $V_{ss}$ (mL/kg) |
|---|---|---|---|---|---|---|
| 1 mg/kg anti-JAG1 | specific | 14.5 ± 0.497 | 13.3 ± 0.552 | 13.3 | 75.0 | 80.7 |
| 10 mg/kg anti-JAG1 | specific | 160 ± 2.00 | 458 ± 19.3 | 458 | 21.8 | 87.6 |
| 100 mg/kg anti-JAG1 | specific | 1480 ± 68.4 | 7220 ± 443 | 7410 | 13.5 | 115 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

```
                        Table of Sequences
SEQ
ID
NO  Description        Sequence 1  Human Jag1         MRSPRTRGRS GRPLSLLLAL LCALRAKVCG ASGQFELEIL SMQNVNGELQ
                       NGNCCGGARN PGDRKCTRDE CDTYFKVCLK EYQSRVTAGG PCSFGSGSTP
                       VIGGNTFNLK ASRGNDRNRI VLPFSFAWPR SYTLLVEAWD SSNDTVQPDS
                       IIEKASHSGM INPSRQWQTL KQNTGVAHFE YQIRVTCDDY YYGFGCNKFC
                       RPRDDFFGHY ACDQNGNKTC MEGWMGPECN RAICRQGCSP KHGSCKLPGD
                       CRCQYGWQGL YCDKCIPHPG CVHGICNEPW QCLCETNWGG QLCDKDLNYC
                       GTHQPCLNGG TCSNTGPDKY QCSCPEGYSG PNCEIAEHAC LSDPCHNRGS
                       CKETSLGFEC ECSPGWTGPT CSTNIDDCSP NNCSHGGTCQ DLVNGFKCVC
                       PPQWTGKTCQ LDANECEAKP CVNAKSCKNL IASYYCDCLP GWMGQNCDIN
                       INDCLGQCQN DASCRDLVNG YRCICPPGYA GDHCERDIDE CASNPCLNGG
                       HCQNEINRFQ CLCPTGFSGN LCQLDIDYCE PNPCQNGAQC YNRASDYFCK
                       CPEDYEGKNC SHLKDHCRTT PCEVIDSCTV AMASNDTPEG VRYISSNVCG
                       PHGKCKSQSG GKFTCDCNKG FTGTYCHENI NDCESNPCRN GGTCIDGVNS
                       YKCICSDGWE GAYCETNIND CSQNPCHNGG TCRDLVNDFY CDCKNGWKGK
                       TCHSRDSQCD EATCNNGGTC YDEGDAFKCM CPGGWEGTTC NIARNSSCLP
                       NPCHNGGTCV VNGESFTCVC KEGWEGPICA QNTNDCSPHP CYNSGTCVDG
                       DNWYRCECAP GFAGPDCRIN INECQSSPCA FGATCVDEIN GYRCVCPPGH
                       SGAKCQEVSG RPCITMGSVI PDGAKWDDDC NTCQCLNGRI ACSKVWCGPR
                       PCLLHKGHSE CPSGQSCIPI LDDQCFVHPC TGVGECRSSS LQPVKTKCTS
                       DSYYQDNCAN ITFTFNKEMM SPGLTTEHIC SELRNLNILK NVSAEYSIYI
                       ACEPSPSANN EIHVAISAED IRDDGNPIKE ITDKIIDLVS KRDGNSSLIA
                       AVAEVRVQRR PLKNRTDFLV PLLSSVLTVA WICCLVTAFY WCLRKRRKPG
                       SHTHSASEDN TTNNVREQLN QIKNPIEKHG ANTVPIKDYE NKNSKMSKIR
                       THNSEVEEDD MDKHQQKARF AKQPAYTLVD REEKPPNGTP TKHPNWTNKQ
                       DNRDLESAQS LNRMEYIV 2  Murine Jag1        MRSPRTRGRP GRPLSLLLAL LCALRAKVCG ASGQFELEIL SMQNVNGELQ
                       NGNCCGGVRN PGDRKCTRDE CDTYFKVCLK EYQSRVTAGG PCSFGSGSTP
                       VIGGNTFNLK ASRGNDRNRI VLPFSFAWPR SYTLLVEAWD SSNDTIQPDS
                       IIEKASHSGM INPSRQWQTL KQNTGIAHFE YQIRVTCDDH YYGFGCNKFC
                       RPRDDFFGHY ACDQNGNKTC MEGWMGPDCN KAICRQGCSP KHGSCKLPGD
                       CRCQYGWQGL YCDKCIPHPG CVHGTCNEPW QCLCETNWGG QLCDKDLNYC
                       GTHQPCLNRG TCSNTGPDKY QCSCPEGYSG PNCEIAEHAC LSDPCHNRGS
                       CKETSSGFEC ECSPGWTGPT CSTNIDDCSP NNCSHGGTCQ DLVNGFKCVC
                       PPQWTGKTCQ LDANECEAKP CVNARSCKNL IASYYCDCLP GWMGQNCDIN
                       INDCLGQCQN DASCRDLVNG YRCICPPGYA GDHCERDIDE CASNPCLNGG
                       HCQNEINRFQ CLCPTGFSGN LCQLDIDYCE PNPCQNGAQC YNRASDYFCK
                       CPEDYEGKNC SHLKDHCRTT TCEVIDSCTV AMASNDTPEG VRYISSNVCG
                       PHGKCKSQSG GKFTCDCNKG FTGTYCHENI NDCESNPCKN GGTCIDGVNS
                       YKCICSDGWE GAHCENNIND CSQNPCHYGG TCRDLVNDFY CDCKNGWKGK
                       TCHSRDSQCD EATCNNGGTC YDEVDTFKCM CPGGWEGTTC NIARNSSCLP
                       NPCHNGGTCV VNGDSFTCVC KEGWEGPICT QNTNDCSPHP CYNSGTCVDG
                       DNWYRCECAP GFAGPDCRIN INECQSSPCA FGATCVDEIN GYQCICPPGH
                       SGAKCHEVSG RSCITMGRVI LDGAKWDDDC NTCQCLNGRV ACSKVWCGPR
                       PCRLHKSHNE CPSGQSCIPV LDDQCFVRPC TGVGECRSSS LQPVKTKCTS
                       DSYYQDNCAN ITFTFNKEMM SPGLTTEHIC SELRNLNILK NVSAEYSIYI
                       ACEPSLSANN EIHVAISAED IRDDGNPVKE ITDKIIDLVS KRDGNSSLIA
                       AVAEVRVQRR PLKNRTDFLV PLLSSVLTVA WVCCLVTAFY WCVRKRRKPS
                       SHTHSAPEDN TTNNVREQLN QIKNPIEKHG ANTVPIKDYE NKNSKMSKIR
                       THNSEVEEDD MDKHQQKVRF AKQPVYTLVD REEKAPSGTP TKHPNWTNKQ
                       DNRDLESAQS LNRMEYIV
```

-continued

Table of Sequences

| SEQ ID NO | Description | Sequence |
|---|---|---|
| 3 | Human Jag2 | MRAQGRGRLP RRLLLLLALW VQAARPMGYF ELQLSALRNV NGELLSGACC DGDGRTTRAG GCGHDECDTY VRVCLKEYQA KVTPTGPCSY GHGATPVLGG NSFYLPPAGA AGDRARARAR AGGDQDPGLV VIPFQFAWPR SFTLIVEAWD WDNDTTPNEE LLIERVSHAG MINPEDRWKS LHFSGHVAHL ELQIRVRCDE NYYSATCNKF CRPRNDFFGH YTCDQYGNKA CMDGWMGKEC KEAVCKQGCN LLHGGCTVPG ECRCSYGWQG RFCDECVPYP GCVHGSCVEP WQCNCETNWG GLLCDKDLNY CGSHHPCTNG GTCINAEPDQ YRCTCPDGYS GRNCEKAEHA CTSNPCANGG SCHEVPSGFE CHCPSGWSGP TCALDIDECA SNPCAAGGTC VDQVDGFECI CPEQWVGATC QLDANECEGK PCLNAFSCKN LIGGYYCDCI PGWKGINCHI NVNDCRGQCQ HGGTCKDLVN GYQCVCPRGF GGRHCELERD ECASSPCHSG GLCEDLADGF HCHCPQGFSG PLCEVDVDLC EPSPCRNGAR CYNLEGDYYC ACPDDFGGKN CSVPREPCPG GACRVIDGCG SDAGPGMPGT AASGVCGPHG RCVSQPGGNF SCICDSGFTG TYCHENIDDC LGQPCRNGGT CIDEVDAFRC FCPSGWEGEL CDTNPNDCLP DPCHSRGRCY DLVNDFYCAC DDGWKGKTCH SREFQCDAYT CSNGGTCYDS GDTFRCACPP GWKGSTCAVA KNSSCLPNPC VNGGTCVGSG ASFSCICRDG WEGRTCTHNT NDCNPLPCYN GGICVDGVNW FRCECAPGFA GPDCRINIDE CQSSPCAYGA TCVDEINGYR CSCPPGRAGP RCQEVIGFGR SCWSRGTPFP HGSSWVEDCN SCRCLDGRRD CSKVWCGWKP CLLAGQPEAL SAQCPPGQRC LEKAPGQCLR PPCEAWGECG AEEPPSTPCL PRSGHLDNNC ARLTLHFNRD HVPQGTTVGA ICSGIRSLPA TRAVARDRLL VLLCDRASSG ASAVEVAVSF SPARDLPDSS LIQGAAHAIV AAITQRGNSS LLLAVTEVKV ETVVTGGSST GLLVPVLCGA FSVLWLACVV LCVWWTRKRR KERERSRLPR EESANNQWAP LNPIRNPIER PGGHKDVLYQ CKNFTPPPRR ADEALPGPAG HAAVREDEED EDLGRGEEDS LEAEKFLSHK FTKDPGRSPG RPAHWASGPK VDNRAVRSIN EARYAGKE |
| 4 | Murine Jag2 | MRARGWGRLP RRLLLLLVLC VQATRPMGYF ELQLSALRNV NGELLSGACC DGDGRTTRAG GCGRDECDTY VRVCLKEYQA KVTPTGPCSY GYGATPVLGG NSFYLPPAGA AGDRARARSR TGGHQDPGLV VIPFQFAWPR SFTLIVEAWD WDNDTTPDEE LLIERVSHAG MINPEDRWKS LHFSGHVAHL ELQIRVRCDE NYYSATCNKF CRPRNDFFGH YTCDQYGNKA CMDGWMGKEC KEAVCKQGCN LLHGGCTVPG ECRCSYGWQG KFCDECVPYP GCVHGSCVEP WHCDCETNWG GLLCDKDLNY CGSHHPCVNG GTCINAEPDQ YLCACPDGYL GKNCERAEHA CASNPCANGG SCHEVPSGFE CHCPSGWSGP TCALDIDECA SNPCAAGGTC VDQVDGFECI CPEQWVGATC QLDANECEGK PCLNAFSCKN LIGGYYCDCL PGWKGINCQI NINDCHGQCQ HGGTCKDLVN GYQCVCPRGF GGRHCELEYD KCASSPCRRG GICEDLVDGF RCHCPRGLSG LHCEVDMDLC EPSPCLNGAR CYNLEGDYYC ACPEDFGGKN CSVPRDTCPG GACRVIDGCG FEAGSRARGV APSGICGPHG HCVSLPGGNF SCICDSGFTG TYCHENIDDC MGQPCRNGGT CIDEVDSFRC FCPSGWEGEL CDINPNDCLP DPCHSRGRCY DLVNDFYCAC DDGWKGKTCH SREFQCDAYT CSNGGTCYDS GDTFRCACPP GWKGSTCTIA KNSSCVPNPC VNGGTCVGSG DSFSCICRDG WEGRTCTHNT NDCNPLPCYN GGICVDGVNW FRCECAPGFA GPDCRINIDE CQSSPCAYGA TCVDEINGYR CSCPPGRSGP RCQEVVIFTR PCWSRGMSFP HGSSWMEDCN SCRCLDGHRD CSKVWCGWKP CLLSGQPSDP SAQCPPGQQC QEKAVGQCLQ PPCENWGECT AEEPLPPSTP CQPRSSHLDN NCARLTLRFN RDQVPQGTTV GAICSGIRAL PATRAAAHDR LLLLLCDRAS SGASAVEVAM SFSPARDLPD SSLIQSTAHA IVAAITQRGN SSLLLAVTEV KVETVVMGGS STGLLVPVLC SVFSVLWLAC VVICVWWTRK RRKERERSRL PRDESTNNQW APLNPIRNPI ERPGGSGLGT GGHKDILYQC KNFTPPPPRA GEALPGPAGH GAGGEDEEDE ELSRGDGDSP EAEKFISHKF TKDPSCSLGR PACWAPGPKV DNRAVRSTKD VRRAGRE |
| 5 | Murine Jag1-DSL-EGF1-4 (mouse Jag1 antigen) | ADLGSQFELE ILSMQNVNGE LQNGNCCGGV RNPGDRKCTR DECDTYFKVC LKEYQSRVTA GGPCSFGSGS TPVIGGNTFN LKASRGNDRN RIVLPFSFAW PRSYTLLVEA WDSSNDTIQP DSIIEKASHS GMINPSRQWQ TLKQNTGIAH FEYQIRVTCD DHYYGFGCNK FCRPRDDFFG HYACDQNGNK TCMEGWMGPD CNKAICRQGC SPKHGSCKLP GDCRCQYGWQ GLYCDKCIPH PGCVHGTCNE PWQCLCETNW GGQLCDKDLN YCGTHQPCLN RGTCSNTGPD KYQCSCPEGY SGPNCEIAEH ACLSDPCHNR GSCKETSSGF ECECSPGWTG PTCSTNIDDE FGLVPRGSGH HHHHH |
| 6 | humanJag1-DSL-EGF1-4 (human Jag1 antigen) | QFELEILSMQ NVNGELQNGN CCGGARNPGD RKCTRDECDT YFKVCLKEYQ SRVTAGGPCS FGSGSTPVIG GNTFNLKASR GNDRNRIVLP FSFAWPRSYT LLVEAWDSSN DTVQPDSIIE KASHSGMINP SRQWQTLKQN TGVAHFEYQI RVTCDDYYYG FGCNKFCRPR DDFFGHYACD QNGNKTCMEG WMGPECNRAI CRQGCSPKHG SCKLGDCRCQ YGWQGLYCDK CIPHPGCVHG ICNEPWQCLC ETNWGGQLCD KDLNYCGTHQ PCLNGGTCSN TGPDKYQCSC PEGYSGPNCE IAEHACLSDP CHNRGSCKET SLGFECECSP GWTGPTCSTN IDD |
| 7 | murine Jag2-DSL-EGF1-4 (mouse Jag2 antigen) | ADLGSMGYFE LQLSALRNVN GELLSGACCD GDGRTTRAGG CGRDECDTYV RVCLKEYQAK VTPTGPCSYG YGATPVLGGN SFYLPPAGAA GDRARARSRT GGHQDPGLVV IPFQFAWPRS FTLIVEAWDW DNDTTPDEEL LIERVSHAGM |

-continued

Table of Sequences

| SEQ ID NO | Description | Sequence |
|---|---|---|
| | | INPEDRWKSL HFSGHVAHLE LQIRVRCDEN YYSATCNKFC RPRNDFFGHY TCDQYGNKAC MDGWMGKECK EAVCKQGCNL LHGGCTVPGE CRCSYGWQGK FCDECVPYPG CVHGSCVEPW HCDCETNWGG LLCDKDLNYC GSHHPCVNGG TCINAEPDQY LCACPDGYLG KNCERAEHAC ASNPCANGGS CHEVPSGFEC HCPSGWNGPT CALDIDEEFG LVPRGSGHHH HHH |
| 8 | human Jag2-DSL-EGF1-4 (human Jag2 antigen) | ARPMGYFELQ LSALRNVNGE LLSGACCDGD GRTTRAGGCG HDECDTYVRV CLKEYQAKVT PTGPCSYGHG ATPVLGGNSF YLPPAGAAGD RARARARAGG DQDPGLVVIP FQFAWPRSFT LIVEAWDWDN DTTPNEELLI ERVSHAGMIN PEDRWKSLHF SGHVAHLELQ IRVRCDENYY SATCNKFCRP RNDFFGHYTC DQYGNKACMD GWMGKECKEA VCKQGCNLLH GGCTVPGECR CSYGWQGRFC DECVPYPGCV HGSCVEPWQC NCETNWGGLL CDKDLNYCGS HHPCTNGGTC INAEPDQYRC TCPDGYSGRN CEKAEHACTS NPCANGGSCH EVPSGFECHC PSGWSGPTCA LDIDEEFGLV PRGSGHHHHH H |
| 9 | Antibody A heavy chain variable region | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG SWFAYWGQGT LVTVSS |
| 10 | Antibody A light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIK |
| 11 | Antibody A heavy chain hypervariable region 1 (HVR-H1) | GFTFSNYGIH |
| 12 | Antibody A HVR-H2 | WITPDGGYTDYADSVKG |
| 13 | Antibody A HVR-H3 | AGSWFAY |
| 14 | Antibody A light chain hypervariable region 1 (HVR-L1) | RASQDVSTAVA |
| 15 | Antibody A HVR-L2 | SASFLYS |
| 16 | Antibody A HVR-L3 | QQSYTTPPT |
| 17 | Antibody A-1 heavy chain variable region | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG SLFAYWGQGT LVTVSS |
| 18 | Antibody A-1 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ YYTTATTFGQ GTKVEIK |
| 19 | Antibody A-1 HVR-H1 | GFTFSNYGIH |
| 20 | Antibody A-1 HVR-H2 | WITPDGGYTDYADSVKG |
| 21 | Antibody A-1 HVR-H3 | AGSLFAY |
| 22 | Antibody A-1 HVR-L1 | RASQDVSTAVA |
| 23 | Antibody A-1 HVR-L2 | SASFLYS |
| 24 | Antibody A-1 HVR-L3 | QQYYTTATT |

Table of Sequences

| SEQ ID NO | Description | Sequence |
|---|---|---|
| 25 | Antibody A-2 heavy chain variable region | EVQLVESGGG LVQPGGSLRL SCAASGFTFS NYGIHWVRQA PGKGLEWVGW ITGNGGYSDY ADSVKGRFTI SADTSKNTAY LQMNSLRAED TAVYYCARAG SWFAYWGQGT LVTVSS |
| 26 | Antibody A-2 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIK |
| 27 | Antibody A-2 HVR-H1 | GFTFSNYGIH |
| 28 | Antibody A-2 HVR-H2 | WITGNGGYSDYADSVKG |
| 29 | Antibody A-2 HVR-H3 | AGSWFAY |
| 30 | Antibody A-2 HVR-L1 | RASQDVSTAVA |
| 31 | Antibody A-2 HVR-L2 | SASFLYS |
| 32 | Antibody A-2 HVR-L3 | QQSYTTPPT |
| 33 | Antibody A-1(S101T) heavy chain variable region | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG TLFAYWGQGT LVTVSS |
| 34 | Antibody A-1(S101T) light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ YYTTATTFGQ GTKVEIK |
| 35 | Antibody A-1(S101T) HVR-H1 | GFTFSNYGIH |
| 36 | Antibody A-1(S101T) HVR-H2 | WITPDGGYTDYADSVKG |
| 37 | Antibody A-1(S101T) HVR-H3 | AGTLFAY |
| 38 | Antibody A-1(S101T) HVR-L1 | RASQDVSTAVA |
| 39 | Antibody A-1(S101T) HVR-L2 | SASFLYS |
| 40 | Antibody A-1(S101T) HVR-L3 | QQYYTTATT |
| 41 | Antibody B-3 heavy chain variable region | EVQLVESGGG LVQPGGSLRL SCAASGFTFT SYDIHWVRQA PGKGLEWVGG ISPADGDTDY ANSVKGRFTI SADTSKNTAY LQMNSLRAED TAVYYCARND YDVRFVGSGM DYWGQGTLVT VSS |
| 42 | Antibody B-3 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SFTAPPTFGQ GTKVEIK |
| 43 | Antibody A, A-1, A-2, A-1(S101T), B-3 light chain framework 1 (LC-FR1) | DIQMTQSPSS LSASVGDRVT ITC |

| SEQ ID NO | Description | Sequence |
|---|---|---|
| 44 | Antibody A, A-1, A-2, A-1(S101T), B-3 LC-FR2 | WYQQKP GKAPKLLIY |
| 45 | Antibody A, A-1, A-2, A-1(S101T), B-3 LC-FR3 | GVPS RFSGSGSGTD FTLTISSLQP EDFATYYC |
| 46 | Antibody A, A-1, A-2, A-1(S101T), B-3 LC-FR4 | FGQ GTKVEIK |
| 47 | AntibodyA, A-1, A-2, A-1(S101T), B-3 heavy chain framework 1 (HC-FR1) | EVQLVESGGG LVQPGGSLRL SCAAS |
| 48 | Antibody A, A-1, A-2, A-1(S101T), B-3 HC-FR2 | WVRQA PGKGLEWVG |
| 49 | Antibody A, A-1, A-2, A-1(S101T), B-3 HC-FR3 | RFTI SADTSKNTAY LQMNSLRAED TAVYYCAR |
| 50 | Antibody A, A-1, A-2, A-1(S101T), B-3 HC-FR4 | WGQGT LVTVSS |
| 51 | Antibody A-1(S101T) IgG1 heavy chain | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG TLFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 52 | Antibody A-1(S101T) IgG1 heavy chain N297G | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG TLFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYGSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 53 | Antibody A-1(S101T) light chain; antibody A-1 light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ YYTTATTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 54 | Antibody A-1(S101X) heavy chain variable region | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG XLFAYWGQGT LVTVSS<br>X is any amino acid other than S. |
| 55 | Antibody A-1(S101X) HVR-H3 | AGXLFAY<br>X is any amino acid other than S. |
| 56 | Antibody A-1(S101X) IgG1 heavy chain | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG XLFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL |

Table of Sequences

| SEQ ID NO | Description | Sequence |
|---|---|---|
| | | PPSREEMTKN QVSLTCLVKG FYPSDIAVEW ESNGQPENNY KTTPPVLDSD<br>GSFFLYSKLT VDKSRWQQGN VFSCSVMHEA LHNHYTQKSL SLSPGK<br>X is any amino acid other than S. |
| 57 | Antibody A-1(S101X) IgG1 heavy chain N297G | EVQLVESGGG LVQPGGSLRL SCAASGFTFS NYGIHWVRQA PGKGLEWVGW<br>ITPDGGYTDY ADSVKGRFTI SADTSKNTAY LQMNSLRAED TAVYYCARAG<br>XLFAYWGQGT LVTVSSASTK GPSVFPLAPS SKSTSGGTAA LGCLVKDYFP<br>EPVTVSWNSG ALTSGVHTFP AVLQSSGLYS LSSVVTVPSS SLGTQTYICN<br>VNHKPSNTKV DKKVEPKSCD KTHTCPPCPA PELLGGPSVF LFPPKPKDTL<br>MISRTPEVTC VVVDVSHEDP EVKFNWYVDG VEVHNAKTKP REEQYGSTYR<br>VVSVLTVLHQ DWLNGKEYKC KVSNKALPAP IEKTISKAKG QPREPQVYTL<br>PPSREEMTKN QVSLTCLVKG FYPSDIAVEW ESNGQPENNY KTTPPVLDSD<br>GSFFLYSKLT VDKSRWQQGN VFSCSVMHEA LHNHYTQKSL SLSPGK<br>X is any amino acid other than S. |
| 58 | Antibody A(S101X) heavy chain variable region | EVQLVESGGG LVQPGGSLRL SCAASGFTFS NYGIHWVRQA PGKGLEWVGW<br>ITPDGGYTDY ADSVKGRFTI SADTSKNTAY LQMNSLRAED TAVYYCARAG<br>XWFAYWGQGT LVTVSS<br>X is any amino acid other than S. |
| 59 | Antibody A(S101X) HVR-H3; Antibody A-2(S101X) HVR-H3 | AGXWFAY<br>X is any amino acid other than S. |
| 62 | Antibody A-2(S101X) heavy chain variable region | EVQLVESGGG LVQPGGSLRL SCAASGFTFS NYGIHWVRQA PGKGLEWVGW<br>ITGNGGYSDY ADSVKGRFTI SADTSKNTAY LQMNSLRAED TAVYYCARAG<br>XWFAYWGQGT LVTVSS<br>X is any amino acid other than S. |
| 63 | Antibody A-1 IgG1 heavy chain N297G | EVQLVESGGG LVQPGGSLRL SCAASGFTFS NYGIHWVRQA PGKGLEWVGW<br>ITPDGGYTDY ADSVKGRFTI SADTSKNTAY LQMNSLRAED TAVYYCARAG<br>SLFAYWGQGT LVTVSSASTK GPSVFPLAPS SKSTSGGTAA LGCLVKDYFP<br>EPVTVSWNSG ALTSGVHTFP AVLQSSGLYS LSSVVTVPSS SLGTQTYICN<br>VNHKPSNTKV DKKVEPKSCD KTHTCPPCPA PELLGGPSVF LFPPKPKDTL<br>MISRTPEVTC VVVDVSHEDP EVKFNWYVDG VEVHNAKTKP REEQYGSTYR<br>VVSVLTVLHQ DWLNGKEYKC KVSNKALPAP IEKTISKAKG QPREPQVYTL<br>PPSREEMTKN QVSLTCLVKG FYPSDIAVEW ESNGQPENNY KTTPPVLDSD<br>GSFFLYSKLT VDKSRWQQGN VFSCSVMHEA LHNHYTQKSL SLSPGK |
| 64 | Antibody A(S101T) HVR-H3; Antibody A-2(S101T) HVR-H3 | AGTWFAY |
| 65 | Antibody A(S101T) heavy chain variable region | EVQLVESGGG LVQPGGSLRL SCAASGFTFS NYGIHWVRQA PGKGLEWVGW<br>ITPDGGYTDY ADSVKGRFTI SADTSKNTAY LQMNSLRAED TAVYYCARAG<br>TWFAYWGQGT LVTVSS |
| 66 | Antibody A-2(S101T) heavy chain variable region | EVQLVESGGG LVQPGGSLRL SCAASGFTFS NYGIHWVRQA PGKGLEWVGW<br>ITGNGGYSDY ADSVKGRFTI SADTSKNTAY LQMNSLRAED TAVYYCARAG<br>TWFAYWGQGT LVTVSS |
| 67 | Antibody A(S101X) IgG1 heavy chain N297G | EVQLVESGGG LVQPGGSLRL SCAASGFTFS NYGIHWVRQA PGKGLEWVGW<br>ITPDGGYTDY ADSVKGRFTI SADTSKNTAY LQMNSLRAED TAVYYCARAG<br>XWFAYWGQGT LVTVSSASTK GPSVFPLAPS SKSTSGGTAA LGCLVKDYFP<br>EPVTVSWNSG ALTSGVHTFP AVLQSSGLYS LSSVVTVPSS SLGTQTYICN<br>VNHKPSNTKV DKKVEPKSCD KTHTCPPCPA PELLGGPSVF LFPPKPKDTL<br>MISRTPEVTC VVVDVSHEDP EVKFNWYVDG VEVHNAKTKP REEQYGSTYR<br>VVSVLTVLHQ DWLNGKEYKC KVSNKALPAP IEKTISKAKG QPREPQVYTL<br>PPSREEMTKN QVSLTCLVKG FYPSDIAVEW ESNGQPENNY KTTPPVLDSD<br>GSFFLYSKLT VDKSRWQQGN VFSCSVMHEA LHNHYTQKSL SLSPGK<br>X is any amino acid other than S. |
| 68 | Antibody A-2(S101X) IgG1 heavy chain N297G | EVQLVESGGG LVQPGGSLRL SCAASGFTFS NYGIHWVRQA PGKGLEWVGW<br>ITGNGGYSDY ADSVKGRFTI SADTSKNTAY LQMNSLRAED TAVYYCARAG<br>XWFAYWGQGT LVTVSSASTK GPSVFPLAPS SKSTSGGTAA LGCLVKDYFP<br>EPVTVSWNSG ALTSGVHTFP AVLQSSGLYS LSSVVTVPSS SLGTQTYICN<br>VNHKPSNTKV DKKVEPKSCD KTHTCPPCPA PELLGGPSVF LFPPKPKDTL |

| SEQ ID NO | Description | Sequence |
|---|---|---|
| | | MISRTPEVTC VVVDVSHEDP EVKFNWYVDG VEVHNAKTKP REEQYGSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK<br>X is any amino acid other than S. |
| 69 | Antibody A(S101T) IgG1 heavy chain N297G | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG TWFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYGSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 70 | Antibody A-2(S101T) IgG1 heavy chain N297G | EVQLVESGGG LVQPGGSLRL SCAASGFTFS NYGIHWVRQA PGKGLEWVGW ITGNGGYSDY ADSVKGRFTI SADTSKNTAY LQMNSLRAED TAVYYCARAG TWFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYGSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 71 | HVR-H2 consensus | WIT(X1)(X2)GGY(X3)DYADSVKG<br>X1 is P or G; X2 is D or N; X3 is T or S |
| 77 | HVR-H3 consensus | AG(X1)(X2)FAY<br>X1 is S or T; X2 is W or L |
| 72 | HVR-H3 consensus (101X) | AG(X1)(X2)FAY<br>X1 is any amino acid other than S; X2 is W or L |
| 73 | HVR-H3 consensus (101T) | AGT(X1)FAY<br>X1 is W or L |
| 74 | HVR-L3 consensus | QQ(X1)YTT(X2)(X3)T<br>X1 is S or Y; X2 is P or A; X3 is P or T |
| 75 | Antibody A light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 76 | Antibody A-2 light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 78 | Antibody A, A-1, A-1(S101T), A-2 alternative HVR-H1 | NYGIH |
| 79 | Antibody A(S101T) IgG1 heavy chain | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG TWFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 80 | Antibody A-2(S101T) IgG1 heavy chain | EVQLVESGGG LVQPGGSLRL SCAASGFTFS NYGIHWVRQA PGKGLEWVGW ITGNGGYSDY ADSVKGRFTI SADTSKNTAY LQMNSLRAED TAVYYCARAG TWFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL |

Table of Sequences

| SEQ ID NO | Description | Sequence |
|---|---|---|
| | | MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 81 | Antibody A-1 IgG1 heavy chain | EVQLVESGGG LVQPGGSLRL SCAASGFTFS NYGIHWVRQA PGKGLEWVGW ITPDGGYTDY ADSVKGRFTI SADTSKNTAY LQMNSLRAED TAVYYCARAG SLFAYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |

What is claimed is:

1. An isolated antibody that binds to human Jagged 1, wherein the antibody comprises an HVR-H1 comprising the amino acid sequence of SEQ ID NO: 35 or 78; an HVR-H2 comprising the amino acid sequence of SEQ ID NO: 28 or 36; an HVR-H3 comprising the amino acid sequence of SEQ ID NO: 55 or 59, wherein X is any amino acid other than S; an HVR-L1 comprising the amino acid sequence of SEQ ID NO: 38; an HVR-L2 comprising the amino acid sequence of SEQ ID NO: 39; and an HVR-L3 comprising the amino acid sequence of SEQ ID NO: 16 or 40.

2. The isolated antibody of claim 1, wherein the antibody comprises:
   a) HVR-H1 comprising the amino acid sequence of SEQ ID NO: 78; HVR-H2 comprising the amino acid sequence of SEQ ID NO: 36; and HVR-H3 comprising the amino acid sequence of SEQ ID NO: 55; or
   b) HVR-H1 comprising the amino acid sequence of SEQ ID NO: 78; HVR-H2 comprising the amino acid sequence of SEQ ID NO: 36; and HVR-H3 comprising the amino acid sequence of SEQ ID NO: 59; or
   c) HVR-H1 comprising the amino acid sequence of SEQ ID NO: 78; HVR-H2 comprising the amino acid sequence of SEQ ID NO: 28; and HVR-H3 comprising the amino acid sequence of SEQ ID NO: 59.

3. The isolated antibody of claim 1, wherein the antibody comprises:
   a) HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40; or
   b) HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

4. The isolated antibody of claim 1, wherein the antibody comprises:
   a) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 55; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40; or
   b) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 59; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16; or
   c) HVR-H1 comprising the amino acid sequence of SEQ ID NO: 78; HVR-H2 comprising the amino acid sequence of SEQ ID NO: 28; HVR-H3 comprising the amino acid sequence of SEQ ID NO: 59; HVR-L1 comprising the amino acid sequence of SEQ ID NO:

38; HVR-L2 comprising the amino acid sequence of SEQ ID NO: 39; and HVR-L3 comprising the amino acid sequence of SEQ ID NO: 16.

5. The isolated antibody of claim 1, wherein the antibody comprises a VH sequence having at least 95% identity to the amino acid sequence of SEQ ID NO: 54, 58, or 62.

6. The isolated antibody of claim 1, wherein the antibody comprises a VL sequence having at least 95% identity to the amino acid sequence of SEQ ID NO: 10, 26, or 34.

7. The isolated antibody of claim 1, wherein the antibody comprises:
   a) a VH sequence having at least 95% identity to the amino acid sequence of SEQ ID NO: 54 and a VL sequence having at least 95% identity to the amino acid sequence of SEQ ID NO: 34; or
   b) a VH sequence having at least 95% identity to the amino acid sequence of SEQ ID NO: 58 and a VL sequence having at least 95% identity to the amino acid sequence of SEQ ID NO: 10; or
   c) a VH sequence having at least 95% identity to the amino acid sequence of SEQ ID NO: 62 and a VL sequence having at least 95% identity to the amino acid sequence of SEQ ID NO: 26.

8. An isolated antibody that binds human Jagged1, comprising:
   a) a VH sequence of SEQ ID NO: 54, wherein X is any amino acid other than S, and a VL sequence of SEQ ID NO: 34; or
   b) a VH sequence of SEQ ID NO: 58, wherein X is any amino acid other than S, and a VL sequence of SEQ ID NO: 10; or
   c) a VH sequence of SEQ ID NO: 62, wherein X is any amino acid other than S, and a VL sequence of SEQ ID NO: 26.

9. The isolated antibody of claim 8, wherein the antibody comprises a VH sequence of SEQ ID NO: 54 and a VL sequence of SEQ ID NO: 34.

10. The isolated antibody of claim 9, wherein the heavy chain comprises the amino acid sequence of SEQ ID NO: 56 and the light chain comprises the amino acid sequence of SEQ ID NO: 53.

11. The isolated antibody of claim 9, wherein the heavy chain comprises the amino acid sequence of SEQ ID NO: 57 and the light chain comprises the amino acid sequence of SEQ ID NO: 53.

12. The isolated antibody of claim 1, wherein X is any amino acid other than S or H.

13. The isolated antibody of claim 1, wherein X is selected from A, D, E, G, I, K, L, N, Q, R T, and V.

14. The isolated antibody of claim 1, wherein X is T.

15. An isolated antibody that binds human Jagged1, comprising:
   a) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 37; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40; or
   b) HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 64; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16; or
   c) HVR-H1 comprising the amino acid sequence of SEQ ID NO: 78; HVR-H2 comprising the amino acid sequence of SEQ ID NO: 28; HVR-H3 comprising the amino acid sequence of SEQ ID NO: 64; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

16. The isolated antibody of claim 15, wherein the antibody comprises:
   a) a VH sequence of SEQ ID NO: 33 and a VL sequence of SEQ ID NO: 34; or
   b) a VH sequence of SEQ ID NO: 65 and a VL sequence of SEQ ID NO: 10; or
   c) a VH sequence of SEQ ID NO: 66 and a VL sequence of SEQ ID NO: 26.

17. An isolated antibody that binds human Jagged1, wherein the antibody comprises a VH sequence of SEQ ID NO: 33 and a VL sequence of SEQ ID NO: 34.

18. The isolated antibody of claim 1, which is a full length IgG1 antibody.

19. The isolated antibody of claim 18, wherein the antibody substantially lacks effector function.

20. The isolated antibody of claim 18, wherein the heavy chain comprises a N297G or N297A mutation.

21. An isolated antibody that binds human Jagged1, wherein the heavy chain comprises the amino acid sequence of SEQ ID NO: 51 and the light chain comprises the amino acid sequence of SEQ ID NO: 53.

22. An isolated antibody that binds human Jagged1, wherein the heavy chain comprises the amino acid sequence of SEQ ID NO: 52 and the light chain comprises the amino acid sequence of SEQ ID NO: 53.

23. The isolated antibody of claim 16, wherein the antibody comprises:
   a) a heavy chain comprising the amino acid sequence of SEQ ID NO: 69 and a light chain comprising the amino acid sequence of SEQ ID NO: 75; or
   b) a heavy chain comprising the amino acid sequence of SEQ ID NO: 70 and a light chain comprising the amino acid sequence of SEQ ID NO: 76; or
   c) a heavy chain comprising the amino acid sequence of SEQ ID NO: 79 and a light chain comprising the amino acid sequence of SEQ ID NO: 75; or
   d) a heavy chain comprising the amino acid sequence of SEQ ID NO: 80 and a light chain comprising the amino acid sequence of SEQ ID NO: 76.

24. The isolated antibody of claim 1, wherein the antibody is an antagonist of Jagged1-mediated signaling.

25. The isolated antibody of claim 1, wherein the antibody does not bind human Jagged2.

26. The isolated antibody of claim 1, wherein the antibody does not bind human DLL4.

27. The isolated antibody of claim 1, wherein the antibody does not bind human DLL1.

28. The isolated antibody of claim 1, wherein the antibody does not bind murine Jagged2, murine DLL4, and/or murine DLL1.

29. The isolated antibody of claim 1, wherein the antibody reduces tumor growth in a mouse xenograft model without causing weight loss.

30. The isolated antibody of claim 29, wherein the mouse xenograft model is a liver cancer xenograft model.

31. The isolated antibody of claim 30, wherein tumor growth is reduced by at least 50, at least 60, at least 70, at least 80, or at least 90 AUC/day TGI %.

32. An immunoconjugate comprising an antibody, wherein the antibody comprises an HVR-H1 comprising the amino acid sequence of SEQ ID NO: 35 or 78; an HVR-H2 comprising the amino acid sequence of SEQ ID NO: 28 or 36; an HVR-H3 comprising the amino acid sequence of SEQ ID NO: 55 or 59, wherein X is any amino acid other than S; an HVR-L1 comprising the amino acid sequence of SEQ ID NO: 38; an HVR-L2 comprising the amino acid sequence of SEQ ID NO: 39; and an HVR-L3 comprising the amino acid sequence of SEQ ID NO: 16 or 40, and a cytotoxic agent.

33. A pharmaceutical formulation comprising an antibody, wherein the antibody comprises an HVR-H1 comprising the amino acid sequence of SEQ ID NO: 35 or 78; an HVR-H2 comprising the amino acid sequence of SEQ ID NO: 28 or 36; an HVR-H3 comprising the amino acid sequence of SEQ ID NO: 55 or 59, wherein X is any amino acid other than S; an HVR-L1 comprising the amino acid sequence of SEQ ID NO: 38; an HVR-L2 comprising the amino acid sequence of SEQ ID NO: 39; and an HVR-L3 comprising the amino acid sequence of SEQ ID NO: 16 or 40, and a pharmaceutically acceptable carrier.

34. A pharmaceutical formulation comprising the immunoconjugate of claim 32 and a pharmaceutically acceptable carrier.

35. The isolated antibody of claim 1 conjugated to a label.

36. An isolated antibody that binds human Jagged1, comprising: HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 37; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 40.

37. An isolated antibody that binds human Jagged1, comprising: HVR-H1 comprising the amino acid sequence of SEQ ID NO: 78; HVR-H2 comprising the amino acid sequence of SEQ ID NO: 36; HVR-H3 comprising the amino acid sequence of SEQ ID NO: 64; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

38. An isolated antibody that binds human Jagged1, comprising: HVR-H1 comprising the amino acid sequence of SEQ ID NO: 78; HVR-H2 comprising the amino acid sequence of SEQ ID NO: 28; HVR-H3 comprising the amino acid sequence of SEQ ID NO: 64; HVR-L1 comprising the amino acid sequence of SEQ ID NO: 38; HVR-L2 comprising the amino acid sequence of SEQ ID NO: 39; and HVR-L3 comprising the amino acid sequence of SEQ ID NO: 16.

* * * * *

UNITED STATES PATENT AND TRADEMARK OFFICE
CERTIFICATE OF CORRECTION

| | |
|---|---|
| PATENT NO. | : 9,518,121 B2 |
| APPLICATION NO. | : 14/619930 |
| DATED | : December 13, 2016 |
| INVENTOR(S) | : Yvonne Chinn et al. |

It is certified that error appears in the above-identified patent and that said Letters Patent is hereby corrected as shown below:

Please replace Figure 16A as issued with the attached corrected Figure 16A.
Please replace Figure 20B as issued with the attached corrected Figure 20B.
Please replace Figure 21B as issued with the attached corrected Figure 21B.
Please replace Figure 24 as issued with the attached corrected Figure 24.

Signed and Sealed this
Eighteenth Day of April, 2017

Michelle K. Lee
*Director of the United States Patent and Trademark Office*

| # | Group Name | Dose (mg/kg) | Vol Last Day | AUC/Day % TGI (Lower, Upper) | TTP 2X | PR |
|---|---|---|---|---|---|---|
| 1 | Anti-Ragweed (Isotype Control) | 10 | 610 | 0 (0, 0) | 18.5 | 0 |
| 2 | Anti-Jag1 A-1-S101T | 3 | 318 | 65 (3, 93) | NA | 0 |
| 3 | Anti-Jag1 A-1-S101T | 10 | 106 | 103 (80, 129) | NA | 7 |
| 4 | Anti-Jag1 A-1-S101T | 30 | 76 | 114 (95, 142) | NA | 7 |
| 5 | Anti-Jag1 A-1-S101T (1x Every 3 Weeks) | 30 | 156 | 100 (73, 124) | NA | 5 |
| 6 | Anti-Jag1 A-1-DANG (Effectorless) | 10 | 88 | 114 (94, 144) | NA | 6 |
| 7 | Anti-Jag1 A-1 | 10 | 109 | 115 (92, 146) | NA | 6 |

*FIG. 20B*

| # | Group Name | Dose (mg/kg) | % BW Last Day | Max % BW | Max % BW Day | AUC/Day (Lower, Upper) |
|---|---|---|---|---|---|---|
| 1 | Anti-Ragweed (Isotype Control) | 10 | 7.48 | 8.69 | 41 | 213 (129,338) |
| 2 | Anti-Jag1 A-1-S101T | 3 | 7.84 | 8.71 | 37 | 77 (26, 137) |
| 3 | Anti-Jag1 A-1-S101T | 10 | 9.53 | 9.53 | 44 | 15 (-24, 64) |
| 4 | Anti-Jag1 A-1-S101T | 30 | 5.08 | 5.5 | 2 | -11 (-47, 24) |
| 5 | Anti-Jag1 A-1-S101T (1x Every 3 Weeks) | 30 | 8.72 | 9.13 | 41 | 33 (-9, 87) |
| 6 | Anti-Jag1 A-1-DANG (Effectorless) | 10 | 5.94 | 7.45 | 37 | -10 (-52, 36) |
| 7 | Anti-Jag1 A-1 | 10 | 6.29 | 6.29 | 44 | -13 (52, 25) |

*FIG. 21B*

SEQUENCE LISTING

<160> NUMBER OF SEQ ID NOS: 111

<210> SEQ ID NO 1
<211> LENGTH: 1218
<212> TYPE: PRT
<213> ORGANISM: Homo sapiens
<220> FEATURE:
<221> NAME/KEY: misc_feature
<223> OTHER INFORMATION: Human Jag1

<400> SEQUENCE: 1

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp

-continued

```
            210                 215                 220
Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                    245                 250                 255

Trp Gln Gly Leu Tyr Cys Asp Lys Cys Ile Pro His Pro Gly Cys Val
                260                 265                 270

His Gly Ile Cys Asn Glu Pro Trp Gln Cys Leu Cys Glu Thr Asn Trp
            275                 280                 285

Gly Gly Gln Leu Cys Asp Lys Asp Leu Asn Tyr Cys Gly Thr His Gln
        290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
                340                 345                 350

Glu Thr Ser Leu Gly Phe Glu Cys Glu Cys Ser Pro Gly Trp Thr Gly
            355                 360                 365

Pro Thr Cys Ser Thr Asn Ile Asp Asp Cys Ser Pro Asn Asn Cys Ser
        370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
                420                 425                 430

Ser Tyr Tyr Cys Asp Cys Leu Pro Gly Trp Met Gly Gln Asn Cys Asp
            435                 440                 445

Ile Asn Ile Asn Asp Cys Leu Gly Gln Cys Gln Asn Asp Ala Ser Cys
        450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
                500                 505                 510

Cys Pro Thr Gly Phe Ser Gly Asn Leu Cys Gln Leu Asp Ile Asp Tyr
            515                 520                 525

Cys Glu Pro Asn Pro Cys Gln Asn Gly Ala Gln Cys Tyr Asn Arg Ala
        530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
                580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
        610                 615                 620

Tyr Cys His Glu Asn Ile Asn Asp Cys Glu Ser Asn Pro Cys Arg Asn
625                 630                 635                 640
```

```
Gly Gly Thr Cys Ile Asp Gly Val Asn Ser Tyr Lys Cys Ile Cys Ser
            645                 650                 655
Asp Gly Trp Glu Gly Ala Tyr Cys Glu Thr Asn Ile Asn Asp Cys Ser
                660                 665                 670
Gln Asn Pro Cys His Asn Gly Thr Cys Arg Asp Leu Val Asn Asp
            675                 680                 685
Phe Tyr Cys Asp Cys Lys Asn Gly Trp Lys Gly Lys Thr Cys His Ser
690                 695                 700
Arg Asp Ser Gln Cys Asp Glu Ala Thr Cys Asn Asn Gly Gly Thr Cys
705                 710                 715                 720
Tyr Asp Glu Gly Asp Ala Phe Lys Cys Met Cys Pro Gly Gly Trp Glu
                725                 730                 735
Gly Thr Thr Cys Asn Ile Ala Arg Asn Ser Ser Cys Leu Pro Asn Pro
            740                 745                 750
Cys His Asn Gly Gly Thr Cys Val Val Asn Gly Glu Ser Phe Thr Cys
            755                 760                 765
Val Cys Lys Glu Gly Trp Glu Gly Pro Ile Cys Ala Gln Asn Thr Asn
770                 775                 780
Asp Cys Ser Pro His Pro Cys Tyr Asn Ser Gly Thr Cys Val Asp Gly
785                 790                 795                 800
Asp Asn Trp Tyr Arg Cys Glu Cys Ala Pro Gly Phe Ala Gly Pro Asp
                805                 810                 815
Cys Arg Ile Asn Ile Asn Glu Cys Gln Ser Ser Pro Cys Ala Phe Gly
                820                 825                 830
Ala Thr Cys Val Asp Glu Ile Asn Gly Tyr Arg Cys Val Cys Pro Pro
            835                 840                 845
Gly His Ser Gly Ala Lys Cys Gln Glu Val Ser Gly Arg Pro Cys Ile
    850                 855                 860
Thr Met Gly Ser Val Ile Pro Asp Gly Ala Lys Trp Asp Asp Asp Cys
865                 870                 875                 880
Asn Thr Cys Gln Cys Leu Asn Gly Arg Ile Ala Cys Ser Lys Val Trp
                885                 890                 895
Cys Gly Pro Arg Pro Cys Leu Leu His Lys Gly His Ser Glu Cys Pro
            900                 905                 910
Ser Gly Gln Ser Cys Ile Pro Ile Leu Asp Asp Gln Cys Phe Val His
            915                 920                 925
Pro Cys Thr Gly Val Gly Glu Cys Arg Ser Ser Ser Leu Gln Pro Val
    930                 935                 940
Lys Thr Lys Cys Thr Ser Asp Ser Tyr Tyr Gln Asp Asn Cys Ala Asn
945                 950                 955                 960
Ile Thr Phe Thr Phe Asn Lys Glu Met Met Ser Pro Gly Leu Thr Thr
                965                 970                 975
Glu His Ile Cys Ser Glu Leu Arg Asn Leu Asn Ile Leu Lys Asn Val
            980                 985                 990
Ser Ala Glu Tyr Ser Ile Tyr Ile Ala Cys Glu Pro Ser Pro Ser Ala
            995                 1000                1005
Asn Asn Glu Ile His Val Ala Ile Ser Ala Glu Asp Ile Arg Asp
        1010                1015                1020
Asp Gly Asn Pro Ile Lys Glu Ile Thr Asp Lys Ile Ile Asp Leu
        1025                1030                1035
Val Ser Lys Arg Asp Gly Asn Ser Ser Leu Ile Ala Ala Val Ala
        1040                1045                1050
```

```
Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Ala Arg Phe Ala Lys Gln
    1160                1165                1170

Pro Ala Tyr Thr Leu Val Asp Arg Glu Glu Lys Pro Pro Asn Gly
    1175                1180                1185

Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 2
<211> LENGTH: 1218
<212> TYPE: PRT
<213> ORGANISM: Mouse sp.
<220> FEATURE:
<221> NAME/KEY: misc_feature
<223> OTHER INFORMATION: Murine Jag1

<400> SEQUENCE: 2

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Val Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190
```

-continued

```
Gly Phe Gly Cys Asn Lys Phe Cys Arg Pro Arg Asp Phe Phe Gly
            195                 200                 205
His Tyr Ala Cys Asp Gln Asn Gly Asn Lys Thr Cys Met Glu Gly Trp
210                 215                 220
Met Gly Pro Asp Cys Asn Lys Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Thr Cys Asn Glu Pro Trp Gln Cys Leu Cys Glu Thr Asn Trp
            275                 280                 285
Gly Gly Gln Leu Cys Asp Lys Asp Leu Asn Tyr Cys Gly Thr His Gln
290                 295                 300
Pro Cys Leu Asn Arg Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
            340                 345                 350
Glu Thr Ser Ser Gly Phe Glu Cys Glu Cys Ser Pro Gly Trp Thr Gly
            355                 360                 365
Pro Thr Cys Ser Thr Asn Ile Asp Asp Cys Ser Pro Asn Asn Cys Ser
370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Arg Ser Cys Lys Asn Leu Ile Ala
            420                 425                 430
Ser Tyr Tyr Cys Asp Cys Leu Pro Gly Trp Met Gly Gln Asn Cys Asp
            435                 440                 445
Ile Asn Ile Asn Asp Cys Leu Gly Gln Cys Gln Asn Asp Ala Ser Cys
450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
            515                 520                 525
Cys Glu Pro Asn Pro Cys Gln Asn Gly Ala Gln Cys Tyr Asn Arg Ala
530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Thr Cys Glu Val Ile Asp
                565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
            595                 600                 605
```

```
Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
    755                 760                 765

Val Cys Lys Glu Gly Trp Glu Gly Pro Ile Cys Thr Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
        820                 825                 830

Ala Thr Cys Val Asp Glu Ile Asn Gly Tyr Gln Cys Ile Cys Pro Pro
        835                 840                 845

Gly His Ser Gly Ala Lys Cys His Glu Val Ser Gly Arg Ser Cys Ile
    850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Leu Ser Ala
        995                 1000                1005

Asn Asn Glu Ile His Val Ala Ile Ser Ala Glu Asp Ile Arg Asp
        1010                1015                1020

Asp Gly Asn Pro Val Lys Glu Ile Thr Asp Lys Ile Ile Asp Leu
```

```
                1025                1030                1035
Val Ser Lys Arg Asp Gly Asn Ser Ser Leu Ile Ala Ala Val Ala
            1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Val Cys
    1070                1075                1080

Cys Leu Val Thr Ala Phe Tyr Trp Cys Val Arg Lys Arg Arg Lys
    1085                1090                1095

Pro Ser Ser His Thr His Ser Ala Pro Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Val Arg Phe Ala Lys Gln
    1160                1165                1170

Pro Val Tyr Thr Leu Val Asp Arg Glu Glu Lys Ala Pro Ser Gly
    1175                1180                1185

Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 3
<211> LENGTH: 1238
<212> TYPE: PRT
<213> ORGANISM: Homo sapiens
<220> FEATURE:
<221> NAME/KEY: misc_feature
<223> OTHER INFORMATION: Human Jag2

<400> SEQUENCE: 3

Met Arg Ala Gln Gly Arg Gly Arg Leu Pro Arg Leu Leu Leu Leu
1               5                   10                  15

Leu Ala Leu Trp Val Gln Ala Arg Pro Met Gly Tyr Phe Glu Leu
                20                  25                  30

Gln Leu Ser Ala Leu Arg Asn Val Asn Gly Glu Leu Leu Ser Gly Ala
            35                  40                  45

Cys Cys Asp Gly Asp Gly Arg Thr Thr Arg Ala Gly Gly Cys Gly His
        50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Arg Ala Gly Gly Asp Gln Asp Pro Gly
        115                 120                 125

Leu Val Val Ile Pro Phe Gln Phe Ala Trp Pro Arg Ser Phe Thr Leu
    130                 135                 140

Ile Val Glu Ala Trp Asp Trp Asp Asn Asp Thr Thr Pro Asn Glu Glu
145                 150                 155                 160
```

-continued

```
Leu Leu Ile Glu Arg Val Ser His Ala Gly Met Ile Asn Pro Glu Asp
            165                 170                 175
Arg Trp Lys Ser Leu His Phe Ser Gly His Val Ala His Leu Glu Leu
        180                 185                 190
Gln Ile Arg Val Arg Cys Asp Glu Asn Tyr Tyr Ser Ala Thr Cys Asn
            195                 200                 205
Lys Phe Cys Arg Pro Arg Asn Asp Phe Phe Gly His Tyr Thr Cys Asp
210                 215                 220
Gln Tyr Gly Asn Lys Ala Cys Met Asp Gly Trp Met Gly Lys Glu Cys
225                 230                 235                 240
Lys Glu Ala Val Cys Lys Gln Gly Cys Asn Leu Leu His Gly Gly Cys
                245                 250                 255
Thr Val Pro Gly Glu Cys Arg Cys Ser Tyr Gly Trp Gln Gly Arg Phe
            260                 265                 270
Cys Asp Glu Cys Val Pro Tyr Pro Gly Cys Val His Gly Ser Cys Val
        275                 280                 285
Glu Pro Trp Gln Cys Asn Cys Glu Thr Asn Trp Gly Gly Leu Leu Cys
    290                 295                 300
Asp Lys Asp Leu Asn Tyr Cys Gly Ser His His Pro Cys Thr Asn Gly
305                 310                 315                 320
Gly Thr Cys Ile Asn Ala Glu Pro Asp Gln Tyr Arg Cys Thr Cys Pro
                325                 330                 335
Asp Gly Tyr Ser Gly Arg Asn Cys Glu Lys Ala Glu His Ala Cys Thr
            340                 345                 350
Ser Asn Pro Cys Ala Asn Gly Gly Ser Cys His Glu Val Pro Ser Gly
        355                 360                 365
Phe Glu Cys His Cys Pro Ser Gly Trp Ser Gly Pro Thr Cys Ala Leu
    370                 375                 380
Asp Ile Asp Glu Cys Ala Ser Asn Pro Cys Ala Ala Gly Gly Thr Cys
385                 390                 395                 400
Val Asp Gln Val Asp Gly Phe Glu Cys Ile Cys Pro Glu Gln Trp Val
                405                 410                 415
Gly Ala Thr Cys Gln Leu Asp Ala Asn Glu Cys Glu Gly Lys Pro Cys
            420                 425                 430
Leu Asn Ala Phe Ser Cys Lys Asn Leu Ile Gly Gly Tyr Tyr Cys Asp
        435                 440                 445
Cys Ile Pro Gly Trp Lys Gly Ile Asn Cys His Ile Asn Val Asn Asp
    450                 455                 460
Cys Arg Gly Gln Cys Gln His Gly Gly Thr Cys Lys Asp Leu Val Asn
465                 470                 475                 480
Gly Tyr Gln Cys Val Cys Pro Arg Gly Phe Gly Gly Arg His Cys Glu
                485                 490                 495
Leu Glu Arg Asp Glu Cys Ala Ser Ser Pro Cys His Ser Gly Gly Leu
            500                 505                 510
Cys Glu Asp Leu Ala Asp Gly Phe His Cys His Cys Pro Gln Gly Phe
        515                 520                 525
Ser Gly Pro Leu Cys Glu Val Asp Val Asp Leu Cys Glu Pro Ser Pro
    530                 535                 540
Cys Arg Asn Gly Ala Arg Cys Tyr Asn Leu Glu Gly Asp Tyr Tyr Cys
545                 550                 555                 560
Ala Cys Pro Asp Asp Phe Gly Gly Lys Asn Cys Ser Val Pro Arg Glu
                565                 570                 575
Pro Cys Pro Gly Gly Ala Cys Arg Val Ile Asp Gly Cys Gly Ser Asp
```

```
            580              585              590
Ala Gly Pro Gly Met Pro Gly Thr Ala Ala Ser Gly Val Cys Gly Pro
            595              600              605

His Gly Arg Cys Val Ser Gln Pro Gly Gly Asn Phe Ser Cys Ile Cys
            610              615              620

Asp Ser Gly Phe Thr Gly Thr Tyr Cys His Glu Asn Ile Asp Asp Cys
625              630              635              640

Leu Gly Gln Pro Cys Arg Asn Gly Gly Thr Cys Ile Asp Glu Val Asp
                645              650              655

Ala Phe Arg Cys Phe Cys Pro Ser Gly Trp Glu Gly Glu Leu Cys Asp
                660              665              670

Thr Asn Pro Asn Asp Cys Leu Pro Asp Pro Cys His Ser Arg Gly Arg
            675              680              685

Cys Tyr Asp Leu Val Asn Asp Phe Tyr Cys Ala Cys Asp Asp Gly Trp
            690              695              700

Lys Gly Lys Thr Cys His Ser Arg Glu Phe Gln Cys Asp Ala Tyr Thr
705              710              715              720

Cys Ser Asn Gly Gly Thr Cys Tyr Asp Ser Gly Asp Thr Phe Arg Cys
                725              730              735

Ala Cys Pro Pro Gly Trp Lys Gly Ser Thr Cys Ala Val Ala Lys Asn
                740              745              750

Ser Ser Cys Leu Pro Asn Pro Cys Val Asn Gly Gly Thr Cys Val Gly
            755              760              765

Ser Gly Ala Ser Phe Ser Cys Ile Cys Arg Asp Gly Trp Glu Gly Arg
            770              775              780

Thr Cys Thr His Asn Thr Asn Asp Cys Asn Pro Leu Pro Cys Tyr Asn
785              790              795              800

Gly Gly Ile Cys Val Asp Gly Val Asn Trp Phe Arg Cys Glu Cys Ala
                805              810              815

Pro Gly Phe Ala Gly Pro Asp Cys Arg Ile Asn Ile Asp Glu Cys Gln
                820              825              830

Ser Ser Pro Cys Ala Tyr Gly Ala Thr Cys Val Asp Glu Ile Asn Gly
            835              840              845

Tyr Arg Cys Ser Cys Pro Pro Gly Arg Ala Gly Pro Arg Cys Gln Glu
            850              855              860

Val Ile Gly Phe Gly Arg Ser Cys Trp Ser Arg Gly Thr Pro Phe Pro
865              870              875              880

His Gly Ser Ser Trp Val Glu Asp Cys Asn Ser Cys Arg Cys Leu Asp
                885              890              895

Gly Arg Arg Asp Cys Ser Lys Val Trp Cys Gly Trp Lys Pro Cys Leu
                900              905              910

Leu Ala Gly Gln Pro Glu Ala Leu Ser Ala Gln Cys Pro Leu Gly Gln
            915              920              925

Arg Cys Leu Glu Lys Ala Pro Gly Gln Cys Leu Arg Pro Cys Glu
            930              935              940

Ala Trp Gly Glu Cys Gly Ala Glu Glu Pro Pro Ser Thr Pro Cys Leu
945              950              955              960

Pro Arg Ser Gly His Leu Asp Asn Asn Cys Ala Arg Leu Thr Leu His
                965              970              975

Phe Asn Arg Asp His Val Pro Gln Gly Thr Thr Val Gly Ala Ile Cys
                980              985              990

Ser Gly Ile Arg Ser Leu Pro Ala  Thr Arg Ala Val Ala  Arg Asp Arg
            995              1000             1005
```

```
Leu Leu Val Leu Cys Asp Arg Ala Ser Gly Ala Ser Ala
    1010                1015            1020

Val Glu Val Ala Val Ser Phe Ser Pro Ala Arg Asp Leu Pro Asp
    1025                1030            1035

Ser Ser Leu Ile Gln Gly Ala Ala His Ala Ile Val Ala Ala Ile
    1040                1045            1050

Thr Gln Arg Gly Asn Ser Ser Leu Leu Leu Ala Val Thr Glu Val
    1055                1060            1065

Lys Val Glu Thr Val Val Thr Gly Gly Ser Ser Thr Gly Leu Leu
    1070                1075            1080

Val Pro Val Leu Cys Gly Ala Phe Ser Val Leu Trp Leu Ala Cys
    1085                1090            1095

Val Val Leu Cys Val Trp Trp Thr Arg Lys Arg Arg Lys Glu Arg
    1100                1105            1110

Glu Arg Ser Arg Leu Pro Arg Glu Glu Ser Ala Asn Asn Gln Trp
    1115                1120            1125

Ala Pro Leu Asn Pro Ile Arg Asn Pro Ile Glu Arg Pro Gly Gly
    1130                1135            1140

His Lys Asp Val Leu Tyr Gln Cys Lys Asn Phe Thr Pro Pro Pro
    1145                1150            1155

Arg Arg Ala Asp Glu Ala Leu Pro Gly Pro Ala Gly His Ala Ala
    1160                1165            1170

Val Arg Glu Asp Glu Glu Asp Glu Asp Leu Gly Arg Gly Glu Glu
    1175                1180            1185

Asp Ser Leu Glu Ala Glu Lys Phe Leu Ser His Lys Phe Thr Lys
    1190                1195            1200

Asp Pro Gly Arg Ser Pro Gly Arg Pro Ala His Trp Ala Ser Gly
    1205                1210            1215

Pro Lys Val Asp Asn Arg Ala Val Arg Ser Ile Asn Glu Ala Arg
    1220                1225            1230

Tyr Ala Gly Lys Glu
    1235

<210> SEQ ID NO 4
<211> LENGTH: 1247
<212> TYPE: PRT
<213> ORGANISM: Mouse sp.
<220> FEATURE:
<221> NAME/KEY: misc_feature
<223> OTHER INFORMATION: Murine Jag2

<400> SEQUENCE: 4

Met Arg Ala Arg Gly Trp Gly Arg Leu Pro Arg Leu Leu Leu Leu
1               5               10              15

Leu Val Leu Cys Val Gln Ala Thr Arg Pro Met Gly Tyr Phe Glu Leu
                20              25              30

Gln Leu Ser Ala Leu Arg Asn Val Asn Gly Glu Leu Leu Ser Gly Ala
            35              40              45

Cys Cys Asp Gly Asp Gly Arg Thr Thr Arg Ala Gly Gly Cys Gly Arg
        50              55              60

Asp Glu Cys Asp Thr Tyr Val Arg Val Cys Leu Lys Glu Tyr Gln Ala
65              70              75              80

Lys Val Thr Pro Thr Gly Pro Cys Ser Tyr Gly Tyr Gly Ala Thr Pro
                85              90              95

Val Leu Gly Gly Asn Ser Phe Tyr Leu Pro Pro Ala Gly Ala Ala Gly
```

```
            100                 105                 110
Asp Arg Ala Arg Ala Arg Ser Arg Thr Gly Gly His Gln Asp Pro Gly
            115                 120                 125

Leu Val Val Ile Pro Phe Gln Phe Ala Trp Pro Arg Ser Phe Thr Leu
            130                 135                 140

Ile Val Glu Ala Trp Asp Trp Asp Asn Asp Thr Thr Pro Asp Glu Glu
145                 150                 155                 160

Leu Leu Ile Glu Arg Val Ser His Ala Gly Met Ile Asn Pro Glu Asp
                    165                 170                 175

Arg Trp Lys Ser Leu His Phe Ser Gly His Val Ala His Leu Glu Leu
                    180                 185                 190

Gln Ile Arg Val Arg Cys Asp Glu Asn Tyr Tyr Ser Ala Thr Cys Asn
                    195                 200                 205

Lys Phe Cys Arg Pro Arg Asn Asp Phe Phe Gly His Tyr Thr Cys Asp
            210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                    245                 250                 255

Thr Val Pro Gly Glu Cys Arg Cys Ser Tyr Gly Trp Gln Gly Lys Phe
            260                 265                 270

Cys Asp Glu Cys Val Pro Tyr Pro Gly Cys Val His Gly Ser Cys Val
            275                 280                 285

Glu Pro Trp His Cys Asp Cys Glu Thr Asn Trp Gly Gly Leu Leu Cys
            290                 295                 300

Asp Lys Asp Leu Asn Tyr Cys Gly Ser His His Pro Cys Val Asn Gly
305                 310                 315                 320

Gly Thr Cys Ile Asn Ala Glu Pro Asp Gln Tyr Leu Cys Ala Cys Pro
                    325                 330                 335

Asp Gly Tyr Leu Gly Lys Asn Cys Glu Arg Ala Glu His Ala Cys Ala
                    340                 345                 350

Ser Asn Pro Cys Ala Asn Gly Gly Ser Cys His Glu Val Pro Ser Gly
            355                 360                 365

Phe Glu Cys His Cys Pro Ser Gly Trp Ser Gly Pro Thr Cys Ala Leu
            370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                    405                 410                 415

Gly Ala Thr Cys Gln Leu Asp Ala Asn Glu Cys Glu Gly Lys Pro Cys
                    420                 425                 430

Leu Asn Ala Phe Ser Cys Lys Asn Leu Ile Gly Gly Tyr Tyr Cys Asp
            435                 440                 445

Cys Leu Pro Gly Trp Lys Gly Ile Asn Cys Gln Ile Asn Ile Asn Asp
            450                 455                 460

Cys His Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                    485                 490                 495

Leu Glu Tyr Asp Lys Cys Ala Ser Ser Pro Cys Arg Arg Gly Gly Ile
                    500                 505                 510

Cys Glu Asp Leu Val Asp Gly Phe Arg Cys His Cys Pro Arg Gly Leu
            515                 520                 525
```

```
Ser Gly Leu His Cys Glu Val Asp Met Asp Leu Cys Glu Pro Ser Pro
        530                 535                 540

Cys Leu Asn Gly Ala Arg Cys Tyr Asn Leu Glu Gly Asp Tyr Tyr Cys
545                 550                 555                 560

Ala Cys Pro Glu Asp Phe Gly Gly Lys Asn Cys Ser Val Pro Arg Asp
                565                 570                 575

Thr Cys Pro Gly Gly Ala Cys Arg Val Ile Asp Gly Cys Gly Phe Glu
            580                 585                 590

Ala Gly Ser Arg Ala Arg Gly Val Ala Pro Ser Gly Ile Cys Gly Pro
        595                 600                 605

His Gly His Cys Val Ser Leu Pro Gly Gly Asn Phe Ser Cys Ile Cys
    610                 615                 620

Asp Ser Gly Phe Thr Gly Thr Tyr Cys His Glu Asn Ile Asp Asp Cys
625                 630                 635                 640

Met Gly Gln Pro Cys Arg Asn Gly Gly Thr Cys Ile Asp Glu Val Asp
                645                 650                 655

Ser Phe Arg Cys Phe Cys Pro Ser Gly Trp Glu Gly Glu Leu Cys Asp
            660                 665                 670

Ile Asn Pro Asn Asp Cys Leu Pro Asp Pro Cys His Ser Arg Gly Arg
        675                 680                 685

Cys Tyr Asp Leu Val Asn Asp Phe Tyr Cys Ala Cys Asp Asp Gly Trp
    690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Thr Ile Ala Lys Asn
            740                 745                 750

Ser Ser Cys Val Pro Asn Pro Cys Val Asn Gly Gly Thr Cys Val Gly
        755                 760                 765

Ser Gly Asp Ser Phe Ser Cys Ile Cys Arg Asp Gly Trp Glu Gly Arg
    770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
                805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
        835                 840                 845

Tyr Arg Cys Ser Cys Pro Pro Gly Arg Ser Gly Pro Arg Cys Gln Glu
    850                 855                 860

Val Val Ile Phe Thr Arg Pro Cys Trp Ser Arg Gly Met Ser Phe Pro
865                 870                 875                 880

His Gly Ser Ser Trp Met Glu Asp Cys Asn Ser Cys Arg Cys Leu Asp
                885                 890                 895

Gly His Arg Asp Cys Ser Lys Val Trp Cys Gly Trp Lys Pro Cys Leu
            900                 905                 910

Leu Ser Gly Gln Pro Ser Asp Pro Ser Ala Gln Cys Pro Pro Gly Gln
        915                 920                 925

Gln Cys Gln Glu Lys Ala Val Gly Gln Cys Leu Gln Pro Pro Cys Glu
    930                 935                 940
```

```
Asn Trp Gly Glu Cys Thr Ala Glu Glu Pro Leu Pro Pro Ser Thr Pro
945                 950                 955                 960

Cys Gln Pro Arg Ser Ser His Leu Asp Asn Asn Cys Ala Arg Leu Thr
            965                 970                 975

Leu Arg Phe Asn Arg Asp Gln Val Pro Gln Gly Thr Thr Val Gly Ala
        980                 985                 990

Ile Cys Ser Gly Ile Arg Ala Leu Pro Ala Thr Arg Ala Ala Ala His
    995                 1000                1005

Asp Arg Leu Leu Leu Leu Cys Asp Arg Ala Ser Ser Gly Ala
    1010                1015                1020

Ser Ala Val Glu Val Ala Met Ser Phe Ser Pro Ala Arg Asp Leu
    1025                1030                1035

Pro Asp Ser Ser Leu Ile Gln Ser Thr Ala His Ala Ile Val Ala
    1040                1045                1050

Ala Ile Thr Gln Arg Gly Asn Ser Ser Leu Leu Leu Ala Val Thr
    1055                1060                1065

Glu Val Lys Val Glu Thr Val Val Met Gly Gly Ser Ser Thr Gly
    1070                1075                1080

Leu Leu Val Pro Val Leu Cys Ser Val Phe Ser Val Leu Trp Leu
    1085                1090                1095

Ala Cys Val Val Ile Cys Val Trp Trp Thr Arg Lys Arg Arg Lys
    1100                1105                1110

Glu Arg Glu Arg Ser Arg Leu Pro Arg Asp Glu Ser Thr Asn Asn
    1115                1120                1125

Gln Trp Ala Pro Leu Asn Pro Ile Arg Asn Pro Ile Glu Arg Pro
    1130                1135                1140

Gly Gly Ser Gly Leu Gly Thr Gly Gly His Lys Asp Ile Leu Tyr
    1145                1150                1155

Gln Cys Lys Asn Phe Thr Pro Pro Pro Arg Arg Ala Gly Glu Ala
    1160                1165                1170

Leu Pro Gly Pro Ala Gly His Gly Ala Gly Gly Glu Asp Glu Glu
    1175                1180                1185

Asp Glu Glu Leu Ser Arg Gly Asp Gly Asp Ser Pro Glu Ala Glu
    1190                1195                1200

Lys Phe Ile Ser His Lys Phe Thr Lys Asp Pro Ser Cys Ser Leu
    1205                1210                1215

Gly Arg Pro Ala Cys Trp Ala Pro Gly Pro Lys Val Asp Asn Arg
    1220                1225                1230

Ala Val Arg Ser Thr Lys Asp Val Arg Arg Ala Gly Arg Glu
    1235                1240                1245

<210> SEQ ID NO 5
<211> LENGTH: 365
<212> TYPE: PRT
<213> ORGANISM: Artificial Sequence
<220> FEATURE:
<223> OTHER INFORMATION: Synthetic: Murine Jag1-DSL-EGF1-4 (mouse Jag1
      antigen)

<400> SEQUENCE: 5

Ala Asp Leu Gly Ser Gln Phe Glu Leu Glu Ile Leu Ser Met Gln Asn
1               5                   10                  15

Val Asn Gly Glu Leu Gln Asn Gly Asn Cys Cys Gly Gly Val Arg Asn
            20                  25                  30

Pro Gly Asp Arg Lys Cys Thr Arg Asp Glu Cys Asp Thr Tyr Phe Lys
        35                  40                  45
```

Val Cys Leu Lys Glu Tyr Gln Ser Arg Val Thr Ala Gly Gly Pro Cys
 50                  55                  60

Ser Phe Gly Ser Gly Ser Thr Pro Val Ile Gly Gly Asn Thr Phe Asn
 65                  70                  75                  80

Leu Lys Ala Ser Arg Gly Asn Asp Arg Asn Arg Ile Val Leu Pro Phe
                 85                  90                  95

Ser Phe Ala Trp Pro Arg Ser Tyr Thr Leu Leu Val Glu Ala Trp Asp
                100                 105                 110

Ser Ser Asn Asp Thr Ile Gln Pro Asp Ser Ile Ile Glu Lys Ala Ser
                115                 120                 125

His Ser Gly Met Ile Asn Pro Ser Arg Gln Trp Gln Thr Leu Lys Gln
            130                 135                 140

Asn Thr Gly Ile Ala His Phe Glu Tyr Gln Ile Arg Val Thr Cys Asp
145                 150                 155                 160

Asp His Tyr Tyr Gly Phe Gly Cys Asn Lys Phe Cys Arg Pro Arg Asp
                165                 170                 175

Asp Phe Phe Gly His Tyr Ala Cys Asp Gln Asn Gly Asn Lys Thr Cys
                180                 185                 190

Met Glu Gly Trp Met Gly Pro Asp Cys Asn Lys Ala Ile Cys Arg Gln
            195                 200                 205

Gly Cys Ser Pro Lys His Gly Ser Cys Lys Leu Pro Gly Asp Cys Arg
    210                 215                 220

Cys Gln Tyr Gly Trp Gln Gly Leu Tyr Cys Asp Lys Cys Ile Pro His
225                 230                 235                 240

Pro Gly Cys Val His Gly Thr Cys Asn Glu Pro Trp Gln Cys Leu Cys
                245                 250                 255

Glu Thr Asn Trp Gly Gly Gln Leu Cys Asp Lys Asp Leu Asn Tyr Cys
            260                 265                 270

Gly Thr His Gln Pro Cys Leu Asn Arg Gly Thr Cys Ser Asn Thr Gly
        275                 280                 285

Pro Asp Lys Tyr Gln Cys Ser Cys Pro Glu Gly Tyr Ser Gly Pro Asn
    290                 295                 300

Cys Glu Ile Ala Glu His Ala Cys Leu Ser Asp Pro Cys His Asn Arg
305                 310                 315                 320

Gly Ser Cys Lys Glu Thr Ser Ser Gly Phe Glu Cys Glu Cys Ser Pro
                325                 330                 335

Gly Trp Thr Gly Pro Thr Cys Ser Thr Asn Ile Asp Asp Glu Phe Gly
            340                 345                 350

Leu Val Pro Arg Gly Ser Gly His His His His His
            355                 360                 365

<210> SEQ ID NO 6
<211> LENGTH: 343
<212> TYPE: PRT
<213> ORGANISM: Artificial Sequence
<220> FEATURE:
<223> OTHER INFORMATION: Synthetic: human Jag1-DSL-EGF1-4 (human Jag1
      antigen)

<400> SEQUENCE: 6

Gln Phe Glu Leu Glu Ile Leu Ser Met Gln Asn Val Asn Gly Glu Leu
 1               5                  10                  15

Gln Asn Gly Asn Cys Cys Gly Gly Ala Arg Asn Pro Gly Asp Arg Lys
                20                  25                  30

Cys Thr Arg Asp Glu Cys Asp Thr Tyr Phe Lys Val Cys Leu Lys Glu

```
                35                  40                  45
Tyr Gln Ser Arg Val Thr Ala Gly Gly Pro Cys Ser Phe Gly Ser Gly
 50                  55                  60

Ser Thr Pro Val Ile Gly Gly Asn Thr Phe Asn Leu Lys Ala Ser Arg
 65                  70                  75                  80

Gly Asn Asp Arg Asn Arg Ile Val Leu Pro Phe Ser Phe Ala Trp Pro
                 85                  90                  95

Arg Ser Tyr Thr Leu Leu Val Glu Ala Trp Asp Ser Ser Asn Asp Thr
                100                 105                 110

Val Gln Pro Asp Ser Ile Ile Glu Lys Ala Ser His Ser Gly Met Ile
            115                 120                 125

Asn Pro Ser Arg Gln Trp Gln Thr Leu Lys Gln Asn Thr Gly Val Ala
130                 135                 140

His Phe Glu Tyr Gln Ile Arg Val Thr Cys Asp Asp Tyr Tyr Tyr Gly
145                 150                 155                 160

Phe Gly Cys Asn Lys Phe Cys Arg Pro Arg Asp Asp Phe Phe Gly His
                165                 170                 175

Tyr Ala Cys Asp Gln Asn Gly Asn Lys Thr Cys Met Glu Gly Trp Met
            180                 185                 190

Gly Pro Glu Cys Asn Arg Ala Ile Cys Arg Gln Gly Cys Ser Pro Lys
        195                 200                 205

His Gly Ser Cys Lys Leu Gly Asp Cys Arg Cys Gln Tyr Gly Trp Gln
210                 215                 220

Gly Leu Tyr Cys Asp Lys Cys Ile Pro His Pro Gly Cys Val His Gly
225                 230                 235                 240

Ile Cys Asn Glu Pro Trp Gln Cys Leu Cys Glu Thr Asn Trp Gly Gly
                245                 250                 255

Gln Leu Cys Asp Lys Asp Leu Asn Tyr Cys Gly Thr His Gln Pro Cys
            260                 265                 270

Leu Asn Gly Gly Thr Cys Ser Asn Thr Gly Pro Asp Lys Tyr Gln Cys
        275                 280                 285

Ser Cys Pro Glu Gly Tyr Ser Gly Pro Asn Cys Glu Ile Ala Glu His
    290                 295                 300

Ala Cys Leu Ser Asp Pro Cys His Asn Arg Gly Ser Cys Lys Glu Thr
305                 310                 315                 320

Ser Leu Gly Phe Glu Cys Glu Cys Ser Pro Gly Trp Thr Gly Pro Thr
                325                 330                 335

Cys Ser Thr Asn Ile Asp Asp
            340

<210> SEQ ID NO 7
<211> LENGTH: 383
<212> TYPE: PRT
<213> ORGANISM: Artificial Sequence
<220> FEATURE:
<223> OTHER INFORMATION: Synthetic: murine Jag2-DSL-EGF1-4 (mouse Jag2
      antigen)

<400> SEQUENCE: 7

Ala Asp Leu Gly Ser Met Gly Tyr Phe Glu Leu Gln Leu Ser Ala Leu
 1               5                  10                  15

Arg Asn Val Asn Gly Glu Leu Leu Ser Gly Ala Cys Cys Asp Gly Asp
                20                  25                  30

Gly Arg Thr Thr Arg Ala Gly Gly Cys Gly Arg Asp Glu Cys Asp Thr
            35                  40                  45
```

```
Tyr Val Arg Val Cys Leu Lys Glu Tyr Gln Ala Lys Val Thr Pro Thr
     50                  55                  60

Gly Pro Cys Ser Tyr Gly Tyr Gly Ala Thr Pro Val Leu Gly Gly Asn
 65                  70                  75                  80

Ser Phe Tyr Leu Pro Ala Gly Ala Ala Gly Asp Arg Ala Arg Ala
             85                  90                  95

Arg Ser Arg Thr Gly Gly His Gln Asp Pro Gly Leu Val Val Ile Pro
                100                 105                 110

Phe Gln Phe Ala Trp Pro Arg Ser Phe Thr Leu Ile Val Glu Ala Trp
                115                 120                 125

Asp Trp Asp Asn Asp Thr Thr Pro Asp Glu Glu Leu Leu Ile Glu Arg
130                 135                 140

Val Ser His Ala Gly Met Ile Asn Pro Glu Asp Arg Trp Lys Ser Leu
145                 150                 155                 160

His Phe Ser Gly His Val Ala His Leu Glu Leu Gln Ile Arg Val Arg
                165                 170                 175

Cys Asp Glu Asn Tyr Tyr Ser Ala Thr Cys Asn Lys Phe Cys Arg Pro
                180                 185                 190

Arg Asn Asp Phe Phe Gly His Tyr Thr Cys Asp Gln Tyr Gly Asn Lys
                195                 200                 205

Ala Cys Met Asp Gly Trp Met Gly Lys Glu Cys Lys Glu Ala Val Cys
210                 215                 220

Lys Gln Gly Cys Asn Leu Leu His Gly Gly Cys Thr Val Pro Gly Glu
225                 230                 235                 240

Cys Arg Cys Ser Tyr Gly Trp Gln Gly Lys Phe Cys Asp Glu Cys Val
                245                 250                 255

Pro Tyr Pro Gly Cys Val His Gly Ser Cys Val Glu Pro Trp His Cys
                260                 265                 270

Asp Cys Glu Thr Asn Trp Gly Gly Leu Leu Cys Asp Lys Asp Leu Asn
                275                 280                 285

Tyr Cys Gly Ser His His Pro Cys Val Asn Gly Gly Thr Cys Ile Asn
290                 295                 300

Ala Glu Pro Asp Gln Tyr Leu Cys Ala Cys Pro Asp Gly Tyr Leu Gly
305                 310                 315                 320

Lys Asn Cys Glu Arg Ala Glu His Ala Cys Ala Ser Asn Pro Cys Ala
                325                 330                 335

Asn Gly Gly Ser Cys His Glu Val Pro Ser Gly Phe Glu Cys His Cys
                340                 345                 350

Pro Ser Gly Trp Asn Gly Pro Thr Cys Ala Leu Asp Ile Asp Glu Glu
                355                 360                 365

Phe Gly Leu Val Pro Arg Gly Ser Gly His His His His His
    370                 375                 380

<210> SEQ ID NO 8
<211> LENGTH: 381
<212> TYPE: PRT
<213> ORGANISM: Artificial Sequence
<220> FEATURE:
<223> OTHER INFORMATION: Synthetic: human Jag2-DSL-EGF1-4 (human Jag2
      antigen)

<400> SEQUENCE: 8

Ala Arg Pro Met Gly Tyr Phe Glu Leu Gln Leu Ser Ala Leu Arg Asn
 1               5                  10                  15

Val Asn Gly Glu Leu Leu Ser Gly Ala Cys Cys Asp Gly Asp Gly Arg
                20                  25                  30
```

Thr Thr Arg Ala Gly Gly Cys Gly His Asp Glu Cys Asp Thr Tyr Val
            35                  40                  45

Arg Val Cys Leu Lys Glu Tyr Gln Ala Lys Val Thr Pro Thr Gly Pro
 50                  55                  60

Cys Ser Tyr Gly His Gly Ala Thr Pro Val Leu Gly Gly Asn Ser Phe
 65                  70                  75                  80

Tyr Leu Pro Pro Ala Gly Ala Gly Asp Arg Ala Arg Ala Arg Ala
                85                  90                  95

Arg Ala Gly Gly Asp Gln Asp Pro Gly Leu Val Val Ile Pro Phe Gln
                100                 105                 110

Phe Ala Trp Pro Arg Ser Phe Thr Leu Ile Val Glu Ala Trp Asp Trp
            115                 120                 125

Asp Asn Asp Thr Thr Pro Asn Glu Glu Leu Leu Ile Glu Arg Val Ser
130                 135                 140

His Ala Gly Met Ile Asn Pro Glu Asp Arg Trp Lys Ser Leu His Phe
145                 150                 155                 160

Ser Gly His Val Ala His Leu Glu Leu Gln Ile Arg Val Arg Cys Asp
                165                 170                 175

Glu Asn Tyr Tyr Ser Ala Thr Cys Asn Lys Phe Cys Arg Pro Arg Asn
                180                 185                 190

Asp Phe Phe Gly His Tyr Thr Cys Asp Gln Tyr Gly Asn Lys Ala Cys
            195                 200                 205

Met Asp Gly Trp Met Gly Lys Glu Cys Lys Glu Ala Val Cys Lys Gln
            210                 215                 220

Gly Cys Asn Leu Leu His Gly Gly Cys Thr Val Pro Gly Glu Cys Arg
225                 230                 235                 240

Cys Ser Tyr Gly Trp Gln Gly Arg Phe Cys Asp Glu Cys Val Pro Tyr
                245                 250                 255

Pro Gly Cys Val His Gly Ser Cys Val Glu Pro Trp Gln Cys Asn Cys
                260                 265                 270

Glu Thr Asn Trp Gly Gly Leu Leu Cys Asp Lys Asp Leu Asn Tyr Cys
            275                 280                 285

Gly Ser His His Pro Cys Thr Asn Gly Thr Cys Ile Asn Ala Glu
            290                 295                 300

Pro Asp Gln Tyr Arg Cys Thr Cys Pro Asp Gly Tyr Ser Gly Arg Asn
305                 310                 315                 320

Cys Glu Lys Ala Glu His Ala Cys Thr Ser Asn Pro Cys Ala Asn Gly
                325                 330                 335

Gly Ser Cys His Glu Val Pro Ser Gly Phe Glu Cys His Cys Pro Ser
            340                 345                 350

Gly Trp Ser Gly Pro Thr Cys Ala Leu Asp Ile Asp Glu Glu Phe Gly
            355                 360                 365

Leu Val Pro Arg Gly Ser Gly His His His His His
    370                 375                 380

<210> SEQ ID NO 9
<211> LENGTH: 116
<212> TYPE: PRT
<213> ORGANISM: Artificial Sequence
<220> FEATURE:
<223> OTHER INFORMATION: Synthetic: Antibody A heavy chain variable
      region

<400> SEQUENCE: 9

Glu Val Gln Leu Val Glu Ser Gly Gly Gly Leu Val Gln Pro Gly Gly

```
                1               5                  10                 15
Ser Leu Arg Leu Ser Cys Ala Ala Ser Gly Phe Thr Phe Ser Asn Tyr
            20                  25                 30

Gly Ile His Trp Val Arg Gln Ala Pro Gly Lys Gly Leu Glu Trp Val
            35                  40                 45

Gly Trp Ile Thr Pro Asp Gly Gly Tyr Thr Asp Tyr Ala Asp Ser Val
        50                  55                 60

Lys Gly Arg Phe Thr Ile Ser Ala Asp Thr Ser Lys Asn Thr Ala Tyr
65                      70                 75                  80

Leu Gln Met Asn Ser Leu Arg Ala Glu Asp Thr Ala Val Tyr Tyr Cys
                    85                  90                 95

Ala Arg Ala Gly Ser Trp Phe Ala Tyr Trp Gly Gln Gly Thr Leu Val
                100                 105                110

Thr Val Ser Ser
            115
```

<210> SEQ ID NO 10
<211> LENGTH: 107
<212> TYPE: PRT
<213> ORGANISM: Artificial Sequence
<220> FEATURE:
<223> OTHER INFORMATION: Synthetic: Antibody A light chain variable
      region

<400> SEQUENCE: 10

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Asp Val Ser Thr Ala
            20                  25                 30

Val Ala Trp Tyr Gln Gln Lys Pro Gly Lys Ala Pro Lys Leu Leu Ile
            35                  40                 45

Tyr Ser Ala Ser Phe Leu Tyr Ser Gly Val Pro Ser Arg Phe Ser Gly
        50                  55                 60

Ser Gly Ser Gly Thr Asp Phe Thr Leu Thr Ile Ser Ser Leu Gln Pro
65                      70                 75                  80

Glu Asp Phe Ala Thr Tyr Tyr Cys Gln Gln Ser Tyr Thr Thr Pro Pro
                    85                  90                 95

Thr Phe Gly Gln Gly Thr Lys Val Glu Ile Lys
                100                 105
```

<210> SEQ ID NO 11
<211> LENGTH: 10
<212> TYPE: PRT
<213> ORGANISM: Artificial Sequence
<220> FEATURE:
<223> OTHER INFORMATION: Synthetic: Antibody A heavy chain hypervariable
      region 1 (HVR-H1)

<400> SEQUENCE: 11

```
Gly Phe Thr Phe Ser Asn Tyr Gly Ile His
1               5                  10
```

<210> SEQ ID NO 12
<211> LENGTH: 17
<212> TYPE: PRT
<213> ORGANISM: Artificial Sequence
<220> FEATURE:
<223> OTHER INFORMATION: Synthetic: Antibody A HVR-H2

<400> SEQUENCE: 12

```
Trp Ile Thr Pro Asp Gly Gly Tyr Thr Asp Tyr Ala Asp Ser Val Lys
1               5                   10                  15

Gly

<210> SEQ ID NO 13
<211> LENGTH: 7
<212> TYPE: PRT
<213> ORGANISM: Artificial Sequence
<220> FEATURE:
<223> OTHER INFORMATION: Synthetic: Antibody A HVR-H3

<400> SEQUENCE: 13

Ala Gly Ser Trp Phe Ala Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic: Antibody A light chain hypervariable
      region 1 (HVR-L1)

<400> SEQUENCE: 14

Arg Ala Ser Gln Asp Val Ser Thr Ala Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic: Antibody A HVR-L2

<400> SEQUENCE: 15

Ser Ala Ser Phe Leu Tyr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic: Antibody A HVR-L3

<400> SEQUENCE: 16

Gln Gln Ser Tyr Thr Thr Pro Pro Thr
1               5

<210> SEQ ID NO 17
<211> LENGTH: 116
<212> TYPE: PRT
<213> ORGANISM: Artificial Sequence
<220> FEATURE:
<223> OTHER INFORMATION: Synthetic: Antibody A-1 heavy chain variable
      region

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
```

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala Gly Ser Leu Phe Ala Tyr Trp Gly Gln Gly Thr Leu Val
            100                 105                 110

Thr Val Ser Ser
            115

<210> SEQ ID NO 18
<211> LENGTH: 107
<212> TYPE: PRT
<213> ORGANISM: Artificial Sequence
<220> FEATURE:
<223> OTHER INFORMATION: Synthetic: Antibody A-1 light chain variable
      region

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Thr Thr Ala Thr
                 85                  90                  95

Thr Phe Gly Gln Gly Thr Lys Val Glu Ile Lys
            100                 105

<210> SEQ ID NO 19
<211> LENGTH: 10
<212> TYPE: PRT
<213> ORGANISM: Artificial Sequence
<220> FEATURE:
<223> OTHER INFORMATION: Synthetic: Antibody A-1 HVR-H1

<400> SEQUENCE: 19

Gly Phe Thr Phe Ser Asn Tyr Gly Ile His
 1               5                  10

<210> SEQ ID NO 20
<211> LENGTH: 17
<212> TYPE: PRT
<213> ORGANISM: Artificial Sequence
<220> FEATURE:
<223> OTHER INFORMATION: Synthetic: Antibody A-1 HVR-H2

<400> SEQUENCE: 20

Trp Ile Thr Pro Asp Gly Gly Tyr Thr Asp Tyr Ala Asp Ser Val Lys
 1               5                  10                  15

Gly

<210> SEQ ID NO 21
<211> LENGTH: 7
<212> TYPE: PRT
<213> ORGANISM: Artificial Sequence
```

```
<220> FEATURE:
<223> OTHER INFORMATION: Synthetic: Antibody A-1 HVR-H3

<400> SEQUENCE: 21

Ala Gly Ser Leu Phe Ala Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic: Antibody A-1 HVR-L1

<400> SEQUENCE: 22

Arg Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic: Antibody A-1 HVR-L2

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic: Antibody A-1 HVR-L3

<400> SEQUENCE: 24

Gln Gln Tyr Tyr Thr Thr Ala Thr Thr
1               5

<210> SEQ ID NO 25
<211> LENGTH: 116
<212> TYPE: PRT
<213> ORGANISM: Artificial Sequence
<220> FEATURE:
<223> OTHER INFORMATION: Synthetic: Antibody A-2 heavy chain variable
      region

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Trp Phe Ala Tyr Trp Gly Gln Gly Thr Leu Val
            100                 105                 110
```

```
Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Synthetic: Antibody A-2 light chain variable
      region

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 27
<211> LENGTH: 10
<212> TYPE: PRT
<213> ORGANISM: Artificial Sequence
<220> FEATURE:
<223> OTHER INFORMATION: Synthetic: Antibody A-2 HVR-H1

<400> SEQUENCE: 27

Gly Phe Thr Phe Ser Asn Tyr Gly Ile His
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic: Antibody A-2 HVR-H2

<400> SEQUENCE: 28

Trp Ile Thr Gly Asn Gly Gly Tyr Ser Asp Tyr Ala Asp Ser Val Lys
1               5                   10                  15

Gly

<210> SEQ ID NO 29
<211> LENGTH: 7
<212> TYPE: PRT
<213> ORGANISM: Artificial Sequence
<220> FEATURE:
<223> OTHER INFORMATION: Synthetic: Antibody A-2 HVR-H3

<400> SEQUENCE: 29

Ala Gly Ser Trp Phe Ala Tyr
1               5

<210> SEQ ID NO 30
<211> LENGTH: 11
```

```
<212> TYPE: PRT
<213> ORGANISM: Artificial Sequence
<220> FEATURE:
<223> OTHER INFORMATION: Synthetic: Antibody A-2 HVR-L1

<400> SEQUENCE: 30

Arg Ala Ser Gln Asp Val Ser Thr Ala Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic: Antibody A-2 HVR-L2

<400> SEQUENCE: 31

Ser Ala Ser Phe Leu Tyr Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic: Antibody A-2 HVR-L3

<400> SEQUENCE: 32

Gln Gln Ser Tyr Thr Thr Pro Pro Thr
1               5

<210> SEQ ID NO 33
<211> LENGTH: 116
<212> TYPE: PRT
<213> ORGANISM: Artificial Sequence
<220> FEATURE:
<223> OTHER INFORMATION: Synthetic: Antibody A-1(S101T) heavy chain
      variable region

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Thr Leu Phe Ala Tyr Trp Gly Gln Gly Thr Leu Val
            100                 105                 110

Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: Synthetic: Antibody A-1(S101T) light chain
      variable region
```

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Ala Thr
                85                  90                  95

Thr Phe Gly Gln Gly Thr Lys Val Glu Ile Lys
            100                 105

<210> SEQ ID NO 35
<211> LENGTH: 10
<212> TYPE: PRT
<213> ORGANISM: Artificial Sequence
<220> FEATURE:
<223> OTHER INFORMATION: Synthetic: Antibody A-1(S101T) HVR-H1

<400> SEQUENCE: 35

Gly Phe Thr Phe Ser Asn Tyr Gly Ile His
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Synthetic: Antibody A-1(S101T) HVR-H2

<400> SEQUENCE: 36

Trp Ile Thr Pro Asp Gly Gly Tyr Thr Asp Tyr Ala Asp Ser Val Lys
1               5                   10                  15

Gly

<210> SEQ ID NO 37
<211> LENGTH: 7
<212> TYPE: PRT
<213> ORGANISM: Artificial Sequence
<220> FEATURE:
<223> OTHER INFORMATION: Synthetic: Antibody A-1(S101T) HVR-H3

<400> SEQUENCE: 37

Ala Gly Thr Leu Phe Ala Tyr
1               5

<210> SEQ ID NO 38
<211> LENGTH: 11
<212> TYPE: PRT
<213> ORGANISM: Artificial Sequence
<220> FEATURE:
<223> OTHER INFORMATION: Synthetic: Antibody A-1(S101T) HVR-L1

<400> SEQUENCE: 38

Arg Ala Ser Gln Asp Val Ser Thr Ala Val Ala
1               5                   10

```
<210> SEQ ID NO 39
<211> LENGTH: 7
<212> TYPE: PRT
<213> ORGANISM: Artificial Sequence
<220> FEATURE:
<223> OTHER INFORMATION: Synthetic: Antibody A-1(S101T) HVR-L2

<400> SEQUENCE: 39

Ser Ala Ser Phe Leu Tyr Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic: Antibody A-1(S101T) HVR-L3

<400> SEQUENCE: 40

Gln Gln Tyr Tyr Thr Thr Ala Thr Thr
1               5

<210> SEQ ID NO 41
<211> LENGTH: 123
<212> TYPE: PRT
<213> ORGANISM: Artificial Sequence
<220> FEATURE:
<223> OTHER INFORMATION: Synthetic: Antibody B-3 heavy chain variable
      region

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Phe Val Gly Ser Gly Met Asp Tyr
            100                 105                 110

Trp Gly Gln Gly Thr Leu Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: Synthetic: Antibody B-3 light chain variable
      region

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Phe Thr Ala Pro Pro
                 85                  90                  95
Thr Phe Gly Gln Gly Thr Lys Val Glu Ile Lys
            100                 105
```

<210> SEQ ID NO 43
<211> LENGTH: 23
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 light chain framework 1 (LC-FR1)

<400> SEQUENCE: 43

```
Asp Ile Gln Met Thr Gln Ser Pro Ser Ser Leu Ser Ala Ser Val Gly
 1               5                  10                  15
Asp Arg Val Thr Ile Thr Cys
            20
```

<210> SEQ ID NO 44
<211> LENGTH: 15
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 LC-FR2

<400> SEQUENCE: 44

```
Trp Tyr Gln Gln Lys Pro Gly Lys Ala Pro Lys Leu Leu Ile Tyr
 1               5                  10                  15
```

<210> SEQ ID NO 45
<211> LENGTH: 32
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 LC-FR3

<400> SEQUENCE: 45

```
Gly Val Pro Ser Arg Phe Ser Gly Ser Gly Ser Gly Thr Asp Phe Thr
 1               5                  10                  15
Leu Thr Ile Ser Ser Leu Gln Pro Glu Asp Phe Ala Thr Tyr Tyr Cys
             20                  25                  30
```

<210> SEQ ID NO 46
<211> LENGTH: 10
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 LC-FR4

<400> SEQUENCE: 46

```
Phe Gly Gln Gly Thr Lys Val Glu Ile Lys
 1               5                  10
```

<210> SEQ ID NO 47
<211> LENGTH: 25
<212> TYPE: PRT

-continued

```
<213> ORGANISM: Artificial Sequence
<220> FEATURE:
<223> OTHER INFORMATION: Synthetic: Antibody A, A-1, A-2, A-1(S101T),
      B-3 heavy chain framework 1 (HC-FR1)

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 48
<211> LENGTH: 14
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 HC-FR2

<400> SEQUENCE: 48

Trp Val Arg Gln Ala Pro Gly Lys Gly Leu Glu Trp Val Gly
1               5                   10

<210> SEQ ID NO 49
<211> LENGTH: 32
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 HC-FR3

<400> SEQUENCE: 49

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 50
<211> LENGTH: 11
<212> TYPE: PRT
<213> ORGANISM: Artificial Sequence
<220> FEATURE:
<223> OTHER INFORMATION: Synthetic: Antibody A, A-1, A-2, A-1(S101T),
      B-3 HC-FR4

<400> SEQUENCE: 50

Trp Gly Gln Gly Thr Leu Val Thr Val Ser Ser
1               5                   10

<210> SEQ ID NO 51
<211> LENGTH: 446
<212> TYPE: PRT
<213> ORGANISM: Artificial Sequence
<220> FEATURE:
<223> OTHER INFORMATION: Synthetic: Antibody A-1(S101T) IgG1 heavy chain

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60
```

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Ala Gly Thr Leu Phe Ala Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 52
<211> LENGTH: 446
<212> TYPE: PRT
<213> ORGANISM: Artificial Sequence
<220> FEATURE:

<223> OTHER INFORMATION: Synthetic: Antibody A-1(S101T) IgG1 heavy chain N297G

<400> SEQUENCE: 52

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asn | Tyr |
| | | | 20 | | | | | 25 | | | | | 30 | | |
| Gly | Ile | His | Trp | Val | Arg | Gln | Ala | Pro | Gly | Lys | Gly | Leu | Glu | Trp | Val |
| | | | 35 | | | | | 40 | | | | | 45 | | |
| Gly | Trp | Ile | Thr | Pro | Asp | Gly | Gly | Tyr | Thr | Asp | Tyr | Ala | Asp | Ser | Val |
| | 50 | | | | | 55 | | | | | 60 | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Ala | Gly | Thr | Leu | Phe | Ala | Tyr | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| 130 | | | | | 135 | | | | | 140 | | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | | 195 | | | | | 200 | | | | | 205 | | |
| Lys | Val | Asp | Lys | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | | 275 | | | | | 280 | | | | | 285 | | |
| Lys | Pro | Arg | Glu | Glu | Gln | Tyr | Gly | Ser | Thr | Tyr | Arg | Val | Val | Ser | Val |
| 290 | | | | | 295 | | | | | 300 | | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Tyr | Thr | Leu | Pro | Pro |
| | | | 340 | | | | | 345 | | | | | 350 | | |
| Ser | Arg | Glu | Glu | Met | Thr | Lys | Asn | Gln | Val | Ser | Leu | Thr | Cys | Leu | Val |
| | | | 355 | | | | | 360 | | | | | 365 | | |
| Lys | Gly | Phe | Tyr | Pro | Ser | Asp | Ile | Ala | Val | Glu | Trp | Glu | Ser | Asn | Gly |
| 370 | | | | | 375 | | | | | 380 | | | | | |
| Gln | Pro | Glu | Asn | Asn | Tyr | Lys | Thr | Thr | Pro | Pro | Val | Leu | Asp | Ser | Asp |
| 385 | | | | | 390 | | | | | 395 | | | | | 400 |

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 53
<211> LENGTH: 214
<212> TYPE: PRT
<213> ORGANISM: Artificial Sequence
<220> FEATURE:
<223> OTHER INFORMATION: Synthetic: Antibody A-1(S101T) light chain;
      antibody A-1 light chain

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Ala Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 116
<212> TYPE: PRT
<213> ORGANISM: Artificial Sequence
<220> FEATURE:
<223> OTHER INFORMATION: Synthetic: Antibody A-1(S101X) heavy chain
      variable region
<220> FEATURE:
<221> NAME/KEY: misc_feature
<222> LOCATION: (101)..(101)
<223> OTHER INFORMATION: Xaa can be any amino acid other than Ser

<400> SEQUENCE: 54

Glu Val Gln Leu Val Glu Ser Gly Gly Gly Leu Val Gln Pro Gly Gly
```

```
                1               5                  10                  15
            Ser Leu Arg Leu Ser Cys Ala Ala Ser Gly Phe Thr Phe Ser Asn Tyr
                            20                  25                  30

Gly Ile His Trp Val Arg Gln Ala Pro Gly Lys Gly Leu Glu Trp Val
                        35                  40                  45

Gly Trp Ile Thr Pro Asp Gly Gly Tyr Thr Asp Tyr Ala Asp Ser Val
                    50                  55                  60

Lys Gly Arg Phe Thr Ile Ser Ala Asp Thr Ser Lys Asn Thr Ala Tyr
            65                  70                  75                  80

Leu Gln Met Asn Ser Leu Arg Ala Glu Asp Thr Ala Val Tyr Tyr Cys
                            85                  90                  95

Ala Arg Ala Gly Xaa Leu Phe Ala Tyr Trp Gly Gln Gly Thr Leu Val
                        100                 105                 110

Thr Val Ser Ser
                    115

<210> SEQ ID NO 55
<211> LENGTH: 7
<212> TYPE: PRT
<213> ORGANISM: Artificial Sequence
<220> FEATURE:
<223> OTHER INFORMATION: Synthetic: Antibody A-1(S101X) HVR-H3
<220> FEATURE:
<221> NAME/KEY: misc_feature
<222> LOCATION: (3)..(3)
<223> OTHER INFORMATION: Xaa can be any amino acid other than Ser

<400> SEQUENCE: 55

Ala Gly Xaa Leu Phe Ala Tyr
1               5

<210> SEQ ID NO 56
<211> LENGTH: 446
<212> TYPE: PRT
<213> ORGANISM: Artificial Sequence
<220> FEATURE:
<223> OTHER INFORMATION: Synthetic: Antibody A-1(S101X) IgG1 heavy chain
<220> FEATURE:
<221> NAME/KEY: misc_feature
<222> LOCATION: (101)..(101)
<223> OTHER INFORMATION: Xaa can be any amino acid other than Ser

<400> SEQUENCE: 56

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asn Tyr
                20                  25                  30

Gly Ile His Trp Val Arg Gln Ala Pro Gly Lys Gly Leu Glu Trp Val
            35                  40                  45

Gly Trp Ile Thr Pro Asp Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Xaa Leu Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
```

```
                130                 135                 140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 57
<211> LENGTH: 446
<212> TYPE: PRT
<213> ORGANISM: Artificial Sequence
<220> FEATURE:
<223> OTHER INFORMATION: Synthetic: Antibody A-1(S101X) IgG1 heavy chain
      N297G
<220> FEATURE:
<221> NAME/KEY: misc_feature
<222> LOCATION: (101)..(101)
<223> OTHER INFORMATION: Xaa can be any amino acid other than Ser

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30
```

```
Gly Ile His Trp Val Arg Gln Ala Pro Gly Lys Gly Leu Glu Trp Val
        35                  40                  45
Gly Trp Ile Thr Pro Asp Gly Gly Tyr Thr Asp Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ala Gly Xaa Leu Phe Ala Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Gly Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445
```

```
<210> SEQ ID NO 58
<211> LENGTH: 116
<212> TYPE: PRT
<213> ORGANISM: Artificial Sequence
<220> FEATURE:
<223> OTHER INFORMATION: Synthetic: Antibody A(S101X) heavy chain
      variable region
<220> FEATURE:
<221> NAME/KEY: misc_feature
<222> LOCATION: (101)..(101)
<223> OTHER INFORMATION: Xaa can be any amino acid other than Ser

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Xaa Trp Phe Ala Tyr Trp Gly Gln Gly Thr Leu Val
            100                 105                 110

Thr Val Ser Ser
        115

<210> SEQ ID NO 59
<211> LENGTH: 7
<212> TYPE: PRT
<213> ORGANISM: Artificial Sequence
<220> FEATURE:
<223> OTHER INFORMATION: Synthetic: Antibody A(S101X) HVR-H3; Antibody
      A-2(S101X) HVR-H3
<220> FEATURE:
<221> NAME/KEY: misc_feature
<222> LOCATION: (3)..(3)
<223> OTHER INFORMATION: Xaa can be any amino acid other than Ser

<400> SEQUENCE: 59

Ala Gly Xaa Trp Phe Ala Tyr
1               5

<210> SEQ ID NO 60

<400> SEQUENCE: 60

000

<210> SEQ ID NO 61

<400> SEQUENCE: 61

000

<210> SEQ ID NO 62
<211> LENGTH: 116
<212> TYPE: PRT
<213> ORGANISM: Artificial Sequence
<220> FEATURE:
<223> OTHER INFORMATION: Synthetic: Antibody A-2(S101X) heavy chain
      variable region
```

```
<220> FEATURE:
<221> NAME/KEY: misc_feature
<222> LOCATION: (101)..(101)
<223> OTHER INFORMATION: Xaa can be any amino acid other than Ser

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Xaa Trp Phe Ala Tyr Trp Gly Gln Gly Thr Leu Val
            100                 105                 110

Thr Val Ser Ser
        115

<210> SEQ ID NO 63
<211> LENGTH: 446
<212> TYPE: PRT
<213> ORGANISM: Artificial Sequence
<220> FEATURE:
<223> OTHER INFORMATION: Synthetic: Antibody A-1 IgG1 heavy chain N297G

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Leu Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

Lys Val Asp Lys Lys Val Glu Pro Lys Ser Cys Asp Lys Thr His Thr
            210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Gly Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 64
<211> LENGTH: 7
<212> TYPE: PRT
<213> ORGANISM: Artificial Sequence
<220> FEATURE:
<223> OTHER INFORMATION: Synthetic: Antibody A(S101T) HVR-H3; Antibody
      A-2(S101T) HVR-H3

<400> SEQUENCE: 64

Ala Gly Thr Trp Phe Ala Tyr
1               5

<210> SEQ ID NO 65
<211> LENGTH: 116
<212> TYPE: PRT
<213> ORGANISM: Artificial Sequence
<220> FEATURE:
<223> OTHER INFORMATION: Synthetic: Antibody A(S101T) heavy chain
      variable region

<400> SEQUENCE: 65

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Ile His Trp Val Arg Gln Ala Pro Gly Lys Gly Leu Glu Trp Val
        35                  40                  45

```
Gly Trp Ile Thr Pro Asp Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala Gly Thr Trp Phe Ala Tyr Trp Gly Gln Gly Thr Leu Val
            100                 105                 110

Thr Val Ser Ser
        115

<210> SEQ ID NO 66
<211> LENGTH: 116
<212> TYPE: PRT
<213> ORGANISM: Artificial Sequence
<220> FEATURE:
<223> OTHER INFORMATION: Synthetic: Antibody A-2(S101T) heavy chain
      variable region

<400> SEQUENCE: 66

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Tyr Ser Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala Gly Thr Trp Phe Ala Tyr Trp Gly Gln Gly Thr Leu Val
            100                 105                 110

Thr Val Ser Ser
        115

<210> SEQ ID NO 67
<211> LENGTH: 446
<212> TYPE: PRT
<213> ORGANISM: Artificial Sequence
<220> FEATURE:
<223> OTHER INFORMATION: Synthetic: Antibody A(S101X) IgG1 heavy chain
      N297G
<220> FEATURE:
<221> NAME/KEY: misc_feature
<222> LOCATION: (101)..(101)
<223> OTHER INFORMATION: Xaa can be any amino acid other than Ser

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
```

```
              65                  70                  75                  80
Leu Gln Met Asn Ser Leu Arg Ala Glu Asp Thr Ala Val Tyr Tyr Cys
                    85                  90                  95

Ala Arg Ala Gly Xaa Trp Phe Ala Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Gly Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 68
<211> LENGTH: 446
<212> TYPE: PRT
<213> ORGANISM: Artificial Sequence
<220> FEATURE:
<223> OTHER INFORMATION: Synthetic: Antibody A-2(S101X) IgG1 heavy chain
      N297G
```

<220> FEATURE:
<221> NAME/KEY: misc_feature
<222> LOCATION: (101)..(101)
<223> OTHER INFORMATION: Xaa can be any amino acid other than Ser

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Xaa Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 69
<211> LENGTH: 446
<212> TYPE: PRT
<213> ORGANISM: Artificial Sequence
<220> FEATURE:
<223> OTHER INFORMATION: Synthetic: Antibody A(S101T) IgG1 heavy chain
      N297G

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Thr Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
            435                 440                 445

<210> SEQ ID NO 70
<211> LENGTH: 446
<212> TYPE: PRT
<213> ORGANISM: Artificial Sequence
<220> FEATURE:
<223> OTHER INFORMATION: Synthetic: Antibody A-2(S101T) IgG1 heavy chain
      N297G

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Thr Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr

```
              210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Gly Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 71
<211> LENGTH: 17
<212> TYPE: PRT
<213> ORGANISM: Artificial Sequence
<220> FEATURE:
<223> OTHER INFORMATION: Synthetic: HVR-H2 consensus
<220> FEATURE:
<221> NAME/KEY: misc_feature
<222> LOCATION: (4)..(4)
<223> OTHER INFORMATION: Xaa is Pro or Gly
<220> FEATURE:
<221> NAME/KEY: misc_feature
<222> LOCATION: (5)..(5)
<223> OTHER INFORMATION: Xaa is Asp or Asn
<220> FEATURE:
<221> NAME/KEY: misc_feature
<222> LOCATION: (9)..(9)
<223> OTHER INFORMATION: Xaa is Thr or Ser

<400> SEQUENCE: 71

Trp Ile Thr Xaa Xaa Gly Gly Tyr Xaa Asp Tyr Ala Asp Ser Val Lys
1               5                   10                  15

Gly

<210> SEQ ID NO 72
<211> LENGTH: 7
<212> TYPE: PRT
<213> ORGANISM: Artificial Sequence
<220> FEATURE:
<223> OTHER INFORMATION: Synthetic: HVR-H3 consensus (101X)
<220> FEATURE:
```

```
<221> NAME/KEY: misc_feature
<222> LOCATION: (3)..(3)
<223> OTHER INFORMATION: Xaa is any amino acid other than Ser
<220> FEATURE:
<221> NAME/KEY: misc_feature
<222> LOCATION: (4)..(4)
<223> OTHER INFORMATION: Xaa is Trp or Leu

<400> SEQUENCE: 72

Ala Gly Xaa Xaa Phe Ala Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic: HVR-H3 consensus (101T)
<220> FEATURE:
<221> NAME/KEY: misc_feature
<222> LOCATION: (4)..(4)
<223> OTHER INFORMATION: Xaa is Trp or Leu

<400> SEQUENCE: 73

Ala Gly Thr Xaa Phe Ala Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic: HVR-L3 consensus
<220> FEATURE:
<221> NAME/KEY: misc_feature
<222> LOCATION: (3)..(3)
<223> OTHER INFORMATION: Xaa is Ser or Tyr
<220> FEATURE:
<221> NAME/KEY: misc_feature
<222> LOCATION: (7)..(7)
<223> OTHER INFORMATION: Xaa is Pro or Ala
<220> FEATURE:
<221> NAME/KEY: misc_feature
<222> LOCATION: (8)..(8)
<223> OTHER INFORMATION: Xaa is Pro or Thr

<400> SEQUENCE: 74

Gln Gln Xaa Tyr Thr Thr Xaa Xaa Thr
1               5

<210> SEQ ID NO 75
<211> LENGTH: 214
<212> TYPE: PRT
<213> ORGANISM: Artificial Sequence
<220> FEATURE:
<223> OTHER INFORMATION: Synthetic: Antibody A light chain

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 214
<212> TYPE: PRT
<213> ORGANISM: Artificial Sequence
<220> FEATURE:
<223> OTHER INFORMATION: Synthetic: Antibody A-2 light chain

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 77
<211> LENGTH: 7
<212> TYPE: PRT
<213> ORGANISM: Artificial Sequence
<220> FEATURE:
<223> OTHER INFORMATION: Synthetic: HVR-H3 consensus
<220> FEATURE:
<221> NAME/KEY: misc_feature
<222> LOCATION: (3)..(3)
<223> OTHER INFORMATION: Xaa is Ser or Thr
<220> FEATURE:
<221> NAME/KEY: misc_feature
<222> LOCATION: (4)..(4)
<223> OTHER INFORMATION: Xaa is Trp or Leu

<400> SEQUENCE: 77

Ala Gly Xaa Xaa Phe Ala Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic: Antibody A, A-1, A-1(S101T), A-2
      alternative HVR-H1

<400> SEQUENCE: 78

Asn Tyr Gly Ile His
1               5

<210> SEQ ID NO 79
<211> LENGTH: 446
<212> TYPE: PRT
<213> ORGANISM: Artificial Sequence
<220> FEATURE:
<223> OTHER INFORMATION: Synthetic: Antibody A(S101T) IgG1 heavy chain

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Thr Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
    435                 440                 445

<210> SEQ ID NO 80
<211> LENGTH: 446
<212> TYPE: PRT
<213> ORGANISM: Artificial Sequence
<220> FEATURE:
<223> OTHER INFORMATION: Synthetic: Antibody A-2(S101T) IgG1 heavy chain

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Ala Gly Thr Trp Phe Ala Tyr Trp Gly Gln Gly Thr Leu Val
             100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 81
<211> LENGTH: 446
<212> TYPE: PRT
<213> ORGANISM: Artificial Sequence
<220> FEATURE:
<223> OTHER INFORMATION: Synthetic: Antibody A-1 IgG1 heavy chain

<400> SEQUENCE: 81

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
         35                  40                  45

Gly Trp Ile Thr Pro Asp Gly Gly Tyr Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala Gly Ser Leu Phe Ala Tyr Trp Gly Gln Gly Thr Leu Val
            100                 105                 110

Thr Val Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
```

```
                       435                 440                 445

<210> SEQ ID NO 82
<211> LENGTH: 5
<212> TYPE: PRT
<213> ORGANISM: Artificial Sequence
<220> FEATURE:
<223> OTHER INFORMATION: Synthetic: Short linker sequence

<400> SEQUENCE: 82

Ala Asp Leu Gly Ser
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic: Thrombin cleavage site

<400> SEQUENCE: 83

Leu Val Pro Arg Gly Ser
1               5

<210> SEQ ID NO 84
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Ser
            20                  25                  30

Asp Ile His Trp Val Arg Gln Ala Pro Gly Lys Gly Leu Glu Trp Val
        35                  40                  45

Gly Gly Ile Thr Pro Ala Asp Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Trp Asn Asn Ser Pro Gly Ser Gly Phe Asp Tyr Trp
            100                 105                 110

Gly Gln Gly Thr Leu Val Thr Val Ser Ser
        115                 120

<210> SEQ ID NO 85
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Ser
            20                  25                  30

Asp Ile His Trp Val Arg Gln Ala Pro Gly Lys Gly Leu Glu Trp Val
```

```
            35                  40                  45
Gly Gly Ile Thr Pro Ala Asp Gly Tyr Thr Asp Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ser Tyr Trp Ser Ser Pro Gly Ser Ala Phe Asp Tyr Trp
            100                 105                 110
Gly Gln Gly Thr Leu Val Thr Val Ser Ser
            115                 120
```

<210> SEQ ID NO 86
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 86

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Ser Asn
            20                  25                  30
Tyr Met Ser Trp Val Arg Gln Ala Pro Gly Lys Gly Leu Glu Trp Val
            35                  40                  45
Ser Thr Ile Trp Tyr Gln Ser Gly Thr Thr Asp Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ser Ser Pro Trp Ser Gly Glu Gly Phe Gly Met Asp Val Trp
            100                 105                 110
Gly Gln Gly Thr Leu Val Thr Val Ser Ser
            115                 120
```

<210> SEQ ID NO 87
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 87

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Ser Asn
            20                  25                  30
Tyr Met Ser Trp Val Arg Gln Ala Pro Gly Lys Gly Leu Glu Trp Val
            35                  40                  45
Ser Thr Ile Trp Tyr Gln Ser Gly Thr Thr Asp Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
```

```
Ala Arg Asp Ser Pro Trp Pro Ser Lys Gly Phe Gly Met Asp Val Trp
            100                 105                 110

Gly Gln Gly Thr Leu Val Thr Val Ser Ser
        115                 120

<210> SEQ ID NO 88
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
            35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Ser Val Gly Ser Gly Met Asp Tyr
            100                 105                 110

Trp Gly Gln Gly Thr Leu Val Thr Val Ser Ser
            115                 120

<210> SEQ ID NO 89
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
            35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Thr Val Gly Ser Gly Met Asp Tyr
            100                 105                 110

Trp Gly Gln Gly Thr Leu Val Thr Val Ser Ser
            115                 120

<210> SEQ ID NO 90
<211> LENGTH: 123
<212> TYPE: PRT
<213> ORGANISM: Artificial Sequence
```

```
<220> FEATURE:
<223> OTHER INFORMATION: Synthetic polypeptide

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Ser Val Gly Ser Gly Met Asp Tyr
            100                 105                 110

Trp Gly Gln Gly Thr Leu Val Thr Val Ser Ser
        115                 120

<210> SEQ ID NO 91
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Phe Val Gly Ser Gly Met Asp Tyr
            100                 105                 110

Trp Gly Gln Gly Thr Leu Val Thr Val Ser Ser
        115                 120

<210> SEQ ID NO 92
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Val Lys Pro Met
            20                  25                  30
```

```
Tyr Met Thr Trp Val Arg Gln Ala Pro Gly Lys Gly Leu Glu Trp Val
            35                  40                  45

Ser Thr Ile Trp Tyr Gln Ser Gly Thr Thr Asp Tyr Ala Asp Ser Val
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Pro Trp Ser Gly Glu Gly Phe Gly Met Asp Val Trp
            100                 105                 110

Gly Gln Gly Thr Leu Val Thr Val Ser Ser
            115                 120
```

<210> SEQ ID NO 93
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 93

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ile Ser Asn
            20                  25                  30

Tyr Val Ser Trp Val Arg Gln Ala Pro Gly Lys Gly Leu Glu Trp Val
            35                  40                  45

Ser Thr Ile Trp Tyr Gln Ser Gly Thr Thr Asp Tyr Ala Asp Ser Val
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Pro Trp Ser Gly Glu Gly Phe Gly Met Asp Val Trp
            100                 105                 110

Gly Gln Gly Thr Leu Val Thr Val Ser Ser
            115                 120
```

<210> SEQ ID NO 94
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 94

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Thr Pro Leu
            20                  25                  30

Tyr Met Ser Trp Val Arg Gln Ala Pro Gly Lys Gly Leu Glu Trp Val
            35                  40                  45

Ser Thr Ile Trp Tyr Gln Ser Gly Thr Thr Asp Tyr Ala Asp Ser Val
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95
```

```
Ala Arg Ser Ser Pro Trp Ser Gly Glu Gly Phe Gly Met Asp Val Trp
            100                 105                 110

Gly Gln Gly Thr Leu Val Thr Val Ser Ser
        115                 120

<210> SEQ ID NO 95
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Pro Met
            20                  25                  30

Tyr Met Ser Trp Val Arg Gln Ala Pro Gly Lys Gly Leu Glu Trp Val
        35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Pro Trp Ser Gly Glu Gly Phe Gly Met Asp Val Trp
            100                 105                 110

Gly Gln Gly Thr Leu Val Thr Val Ser Ser
        115                 120

<210> SEQ ID NO 96
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 97
<211> LENGTH: 107
<212> TYPE: PRT
<213> ORGANISM: Artificial Sequence
<220> FEATURE:
<223> OTHER INFORMATION: Synthetic polypeptide
```

```
<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ser Pro Ser
                85                  90                  95

Thr Phe Gly Gln Gly Thr Lys Val Glu Ile Lys
            100                 105

<210> SEQ ID NO 98
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Leu
                85                  90                  95

Thr Phe Gly Gln Gly Thr Lys Val Glu Ile Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Leu Ser Ser Pro Ile
                85                  90                  95

Thr Phe Gly Gln Gly Thr Lys Val Glu Ile Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Ala Pro
                85                  90                  95

Thr Phe Gly Gln Gly Thr Lys Val Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Trp Thr Ala Pro Pro
                85                  90                  95

Thr Phe Gly Gln Gly Thr Lys Val Glu Ile Lys
            100                 105
```

<210> SEQ ID NO 103
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 103

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Phe Thr Ala Pro Pro
                85                  90                  95

Thr Phe Gly Gln Gly Thr Lys Val Glu Ile Lys
            100                 105
```

<210> SEQ ID NO 104
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 104

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Ser Ser Pro Leu
                85                  90                  95
```

Thr Phe Gly Gln Gly Thr Lys Val Glu Ile Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Ser Pro Leu
                85                  90                  95

Thr Phe Gly Gln Gly Thr Lys Val Glu Ile Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Leu
                85                  90                  95

Thr Phe Gly Gln Gly Thr Lys Val Glu Ile Lys
            100                 105

<210> SEQ ID NO 107
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
             20                  25                  30

Leu Ala Trp Tyr Gln Gln Lys Pro Gly Lys Ala Pro Lys Leu Leu Ile
         35                  40                  45

Tyr Gly Ala Ser Ser Arg Ala Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Leu
                 85                  90                  95

Thr Phe Gly Gln Gly Thr Lys Val Glu Ile Lys
            100                 105

<210> SEQ ID NO 108
<211> LENGTH: 445
<212> TYPE: PRT
<213> ORGANISM: Artificial Sequence
<220> FEATURE:
<223> OTHER INFORMATION: Synthetic

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
         35                  40                  45

Gly Trp Ile Thr Gly Asn Gly Gly Tyr Ser Asp Tyr Ala Asp Ser Val
 50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                 85                  90                  95

Ala Arg Ala Gly Ser Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

```
Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 109
<211> LENGTH: 13
<212> TYPE: PRT
<213> ORGANISM: Artificial Sequence
<220> FEATURE:
<223> OTHER INFORMATION: Synthetic

<400> SEQUENCE: 109

Ser Leu Phe Ala Tyr Gly Gln Gly Thr Leu Val Thr Val
1               5                   10

<210> SEQ ID NO 110
<211> LENGTH: 698
<212> TYPE: PRT
<213> ORGANISM: Artificial Sequence
<220> FEATURE:
<223> OTHER INFORMATION: Synthetic

<400> SEQUENCE: 110

Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Ile His Trp Val Arg Gln Ala Pro Gly Lys Gly Leu
    50                  55                  60

Glu Trp Val Gly Trp Ile Thr Pro Asp Gly Gly Tyr Thr Asp Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Ala Gly Ser Leu Phe Ala Tyr Trp Gly Gln Gly
        115                 120                 125
```

```
Thr Leu Val Thr Val Ser Ser Ala Ser Thr Lys Gly Pro Ser Val Tyr
    130                 135                 140
Pro Leu Ala Pro Val Cys Gly Asp Thr Thr Gly Ser Ser Val Thr Leu
145                 150                 155                 160
Gly Cys Leu Val Lys Gly Tyr Phe Pro Glu Pro Val Thr Leu Thr Trp
                165                 170                 175
Asn Ser Gly Ser Leu Ser Ser Gly Val His Thr Phe Pro Ala Val Leu
            180                 185                 190
Gln Ser Asp Leu Tyr Thr Leu Ser Ser Val Thr Val Thr Ser Ser
        195                 200                 205
Thr Trp Pro Ser Gln Ser Ile Thr Cys Asn Val Ala His Pro Ala Ser
    210                 215                 220
Ser Thr Lys Val Asp Lys Lys Ile Glu Pro Arg Gly Pro Thr Ile Lys
225                 230                 235                 240
Pro Cys Pro Pro Cys Lys Cys Pro Ala Pro Asn Leu Leu Gly Gly Pro
                245                 250                 255
Ser Val Phe Ile Phe Pro Pro Lys Ile Lys Asp Val Leu Met Ile Ser
            260                 265                 270
Leu Ser Pro Ile Val Thr Cys Val Val Val Asp Val Ser Glu Asp Asp
        275                 280                 285
Pro Asp Val Gln Ile Ser Trp Phe Val Asn Asn Val Glu Val His Thr
290                 295                 300
Ala Gln Thr Gln Thr His Arg Glu Asp Tyr Asn Ser Thr Leu Arg Val
305                 310                 315                 320
Val Ser Ala Leu Pro Ile Gln His Gln Asp Trp Met Ser Gly Lys Glu
                325                 330                 335
Phe Lys Cys Lys Val Asn Asn Lys Asp Leu Pro Ala Pro Ile Glu Arg
            340                 345                 350
Thr Ile Ser Lys Pro Lys Gly Ser Val Arg Ala Pro Gln Val Tyr Val
        355                 360                 365
Leu Pro Pro Pro Glu Glu Glu Met Thr Lys Lys Gln Val Thr Leu Thr
    370                 375                 380
Cys Met Val Thr Asp Phe Met Pro Glu Asp Ile Tyr Val Glu Trp Thr
385                 390                 395                 400
Asn Asn Gly Lys Thr Glu Leu Asn Tyr Lys Asn Thr Glu Pro Val Leu
                405                 410                 415
Asp Ser Asp Gly Ser Tyr Phe Met Tyr Ser Lys Leu Arg Val Glu Lys
            420                 425                 430
Lys Asn Trp Val Glu Arg Asn Ser Tyr Ser Cys Ser Val Val His Glu
        435                 440                 445
Gly Leu His Asn His His Thr Thr Lys Ser Phe Ser Arg Thr Pro Gly
    450                 455                 460
Lys Met Gly Trp Ser Cys Ile Ile Leu Phe Leu Val Ala Thr Ala Thr
465                 470                 475                 480
Gly Val His Ser Asp Ile Gln Met Thr Gln Ser Pro Ser Ser Leu Ser
                485                 490                 495
Ala Ser Val Gly Asp Arg Val Thr Ile Thr Cys Arg Ala Ser Gln Asp
            500                 505                 510
Val Ser Thr Ala Val Ala Trp Tyr Gln Gln Lys Pro Gly Lys Ala Pro
        515                 520                 525
Lys Leu Leu Ile Tyr Ser Ala Ser Phe Leu Tyr Ser Gly Val Pro Ser
    530                 535                 540
```

```
Arg Phe Ser Gly Ser Gly Ser Gly Thr Asp Phe Thr Leu Thr Ile Ser
545                 550                 555                 560

Ser Leu Gln Pro Glu Asp Phe Ala Thr Tyr Tyr Cys Gln Gln Tyr Tyr
                565                 570                 575

Thr Thr Ala Thr Thr Phe Gly Gln Gly Thr Lys Val Glu Ile Lys Arg
            580                 585                 590

Ala Asp Ala Ala Pro Thr Val Ser Ile Phe Pro Pro Ser Ser Glu Gln
            595                 600                 605

Leu Thr Ser Gly Gly Ala Ser Val Val Cys Phe Leu Asn Asn Phe Tyr
        610                 615                 620

Pro Lys Asp Ile Asn Val Lys Trp Lys Ile Asp Gly Ser Glu Arg Gln
625                 630                 635                 640

Asn Gly Val Leu Asn Ser Trp Thr Asp Gln Asp Ser Lys Asp Ser Thr
                645                 650                 655

Tyr Ser Met Ser Ser Thr Leu Thr Leu Thr Lys Asp Glu Tyr Glu Arg
                660                 665                 670

His Asn Ser Tyr Thr Cys Glu Ala Thr His Lys Thr Ser Thr Ser Pro
            675                 680                 685

Ile Val Lys Ser Phe Asn Arg Asn Glu Cys
        690                 695

<210> SEQ ID NO 111
<211> LENGTH: 15
<212> TYPE: PRT
<213> ORGANISM: Artificial Sequence
<220> FEATURE:
<223> OTHER INFORMATION: Synthetic

<400> SEQUENCE: 111

Glu Val Gln Leu Val Glu Ser Gly Gly Gly Leu Val Gln Pro Gly
1               5                   10                  15
```